US007700593B2

United States Patent
Zhang et al.

(10) Patent No.: US 7,700,593 B2
(45) Date of Patent: Apr. 20, 2010

(54) IMIDAZO- AND TRIAZOLO-PYRIDINE COMPOUNDS AND METHODS OF USE THEREOF

(75) Inventors: Dawei Zhang, Thousand Oaks, CA (US); Andrew Tasker, Simi Valley, CA (US); Kelvin K. C. Sham, Thousand Oaks, CA (US); Partha Pratim Chakrabarti, Nagpur (IN); James Richard Falsey, Moorpark, CA (US); Bradley J. Herberich, Newbury Park, CA (US); Liping H. Pettus, Thousand Oaks, CA (US); Robert M. Rzasa, Ventura, CA (US)

(73) Assignee: Amgen Inc., Thousand Oaks, CA (US)

( * ) Notice: Subject to any disclaimer, the term of this patent is extended or adjusted under 35 U.S.C. 154(b) by 74 days.

(21) Appl. No.: 11/973,076

(22) Filed: Oct. 5, 2007

(65) Prior Publication Data

US 2008/0161303 A1 Jul. 3, 2008

Related U.S. Application Data

(60) Provisional application No. 60/851,247, filed on Oct. 11, 2006.

(51) Int. Cl.
*A61K 31/5377* (2006.01)
*C07D 221/02* (2006.01)
*A61K 31/496* (2006.01)
*A61P 29/00* (2006.01)
*C07D 295/00* (2006.01)
*A61K 31/437* (2006.01)

(52) U.S. Cl. .............. 514/233.2; 514/303; 514/300; 514/253.04; 546/119; 546/121; 544/127; 544/362

(58) Field of Classification Search ............... 546/121, 546/119; 514/303, 233.2, 300, 253.04; 544/362
See application file for complete search history.

(56) References Cited

U.S. PATENT DOCUMENTS

| 4,242,515 | A | | 12/1980 | Trust et al. |
| 4,550,166 | A | * | 10/1985 | Moran et al. ............... 546/119 |
| 6,043,369 | A | * | 3/2000 | Schefczik ............... 546/119 |
| 6,303,625 | B1 | | 10/2001 | Hoekstra et al. |
| 6,635,644 | B2 | | 10/2003 | Salituro et al. |
| 6,794,380 | B2 | | 9/2004 | Brown |
| 7,259,171 | B2 | | 8/2007 | Dombroski et al. |
| 2004/0143119 | A1 | | 7/2004 | Kang |
| 2006/0122221 | A1 | | 6/2006 | Angell et al. |
| 2006/0154930 | A1 | | 7/2006 | Brown et al. |
| 2006/0281750 | A1 | * | 12/2006 | Li et al. ............... 514/248 |
| 2006/0287324 | A1 | | 12/2006 | Sun et al. |
| 2007/0032681 | A1 | | 2/2007 | Walsdorff et al. |
| 2007/0299103 | A1 | | 12/2007 | Abel et al. |

FOREIGN PATENT DOCUMENTS

| JP | 47047396 | * | 11/1972 |
| WO | 9716442 A1 | | 5/1997 |
| WO | 2004022535 | * | 3/2004 |
| WO | 2004081001 | * | 9/2004 |
| WO | 2006018727 A2 | | 2/2006 |

OTHER PUBLICATIONS

Yurugi et al., Yakugaku Zasshi (1973), 93(5), 642-7.*
Alexis et al., Journal of cutaneous medicine and surgery, (Dec. 2005) vol. 9, No. 6, pp. 296-302. Ref: 67Journal code: 9614685. ISSN: 1203-4754.*
El-Moybayed et al., Egyptian Journal of Pharmaceutical Sciences (1989), 30(1-4), 329-37.*
Alajarin et al., Bioquimica (1980), 76(3), 207-10.*
Moran D B et al: "Synthesis of (Pyridinyl)-1,2,4-Triazolo-4,3-Alpha-Pyridines" Journal of Heterocyclic Chemistry, Heterocorporation. Provo, US, vol. 23, Jul. 1986, pp. 1071-1077.
McClure, Kim F. et al: "Theoretical and Experimental Design of Atypical Kinase Inhibitors: Application to p38 MAP kinase" Journal of Medicinal Chemistry, vol. 48, May 8, 2005, pp. 5728-5737.

* cited by examiner

*Primary Examiner*—D. Margaret Seaman
*Assistant Examiner*—Niloofar Rahmani
(74) *Attorney, Agent, or Firm*—G. Prabhakar Reddy

(57) ABSTRACT

The present invention comprises a new class of compounds useful for the prophylaxis and treatment of protein kinase mediated diseases, including inflammation and related conditions. The compounds have a general Formula I

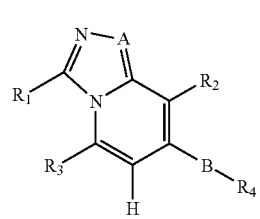

wherein A, B, $R^1$, $R^2$, $R^3$ and $R^4$ are defined herein. The invention also comprises pharmaceutical compositions including one or more compounds of Formula I, uses of such compounds and compositions for treatment of P38 map kinase mediated diseases including rheumatoid arthritis, psoriasis and other inflammation disorders, as well as intermediates and processes useful for the preparation of compounds of Formula I.

13 Claims, No Drawings

IMIDAZO- AND TRIAZOLO-PYRIDINE COMPOUNDS AND METHODS OF USE THEREOF

This application claims the benefit of U.S. Provisional Application No. 60/851,247, filed Oct. 11, 2006, which is hereby incorporated by reference.

FIELD OF THE INVENTION

The invention relates generally to the field of pharmaceutical agents and, more specifically, to pharmaceutically active compounds, pharmaceutical compositions and methods of use thereof, to treat various inflammatory disorders, including TNF-α, IL-1β, IL-6 and/or IL-8 mediated diseases and other maladies, such as pain. The invention also relates to intermediates and processes useful in the preparation of such compounds.

BACKGROUND OF THE INVENTION

Protein kinases represent a large family of enzymes, which catalyze the phosphorylation of target protein substrates. The phosphorylation is usually a transfer reaction of a phosphate group from ATP to the protein substrate. Common points of attachment for the phosphate group to the protein substrate include, for example, a tyrosine, serine or threonine residue. For example, protein tyrosine kinases (PTKs) are enzymes, which catalyze the phosphorylation of specific tyrosine residues in cellular proteins. Examples of kinases in the protein kinase family include, without limitation, abl, Akt, bcr-abl, Blk, Brk, Btk, c-kit, c-Met, c-src, c-fms, CDK1, CDK2, CDK3, CDK4, CDK5, CDK6, CDK7, CDK8, CDK9, CDK10, cRaf1, CSF1R, CSK, EGFR, ErbB2, ErbB3, ErbB4, Erk, Fak, fes, FGFR1, FGFR2, FGFR3, FGFR4, FGFR5, Fgr, flt-1, Fps, Frk, Fyn, Hck, IGF-1R, INS-R, Jak, KDR, Lck, Lyn, MEK, p38, PDGFR, PIK, PKC, PYK2, ros, tie, tie2, TRK, Yes, and Zap70. Due to their activity in numerous cellular processes, protein kinases have emerged as important therapeutic targets.

Protein kinases play a central role in the regulation and maintenance of a wide variety of cellular processes and cellular function. For example, kinase activity acts as molecular switches regulating inflammatory cytokine production via various pathways. Uncontrolled or excessive cytokine production has been observed in many disease states, and particularly in those related to inflammation.

The p38 protein kinase has been reported to be involved in the regulation of inflammatory cytokines. Interleukin-1 (IL-1) and Tumor Necrosis Factor α (TNF-α) are pro-inflammatory cytokines secreted by a variety of cells, including monocytes and macrophages, in response to many inflammatory stimuli (e.g., lipopolysaccharide—LPS) or external cellular stress (e.g., osmotic shock and peroxide).

Elevated levels of TNF-α over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

TNF-α has been reported to play a role in head trauma, stroke, and ischemia. For instance, in animal models of head trauma (rat), TNF-α levels increased in the contused hemisphere (Shohami et al., J. Cereb. Blood Flow Metab. 14:615 (1994)). In a rat model of ischemia wherein the middle cerebral artery was occluded, the levels of TNF-α mRNA of TNF-α increased (Feurstein et al., Neurosci. Lett. 164:125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, Stroke 25:1481 (1994)).

TNF-α appears to play a role in promoting certain viral life cycles and disease states associated therewith. For instance, TNF-α secreted by monocytes induced elevated levels of HIV expression in a chronically infected T cell clone (Clouse et al., J. Immunol. 142:431 (1989)). Lahdevirta et al., (Am. J. Med. 85:289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as IL-1, IL-6, and IL-8. Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

Antagonism of TNF-α has been reported to be beneficial for treating uveitis (Reiff et al, A&R 44:141-145 (2001)); Sepsis (Abraham, Lancet, 351:929 (1998)); Systemic Lupus Erythrematosis (SLE) (Aringer, A&R, 50:3161 (2004)); Graft vs Host Disease (Couriel, Curr. Opinion Oncology, 12:582 (2000)); Polymyositis and Dermatomyositis (Labiache, Rheumatology, 43:531 (2004)); Type II diabetes (Ruan, Cytokine GF Review, 14:447 (2003)); Sjogren's disease (Marriette, A&R, 50:1270 (2004)), Sarcoidosis (Roberts, Chest, 124:2028 (2003)); Wegener's granulomatosis (WGET, New England J. Med., 352:351 (2005)) and post MI cardiac dysfunction (Sugano et al, Mol. Cell Bioch., 266:127 (2004)). In addition, TNF-α has been reported to play a role in SAPHO, periodic fever, relapsing polychrondritis, multicentric reticulohistiocytosis, macrophage activation syndrome, Hyper IgD syndrome, familial Hibernian fever, Pyoderma gangrenosum, Cochleovestibular disorders, Cicatrical pemphigoid, Herniated intervertebral disc diseases, amyloidosis, CINCA syndrome, myelodisplastic syndrome, alcoholic hepatitis, and endometriosis. Finally, indications which have already been approved for an agent which modulates TNF-α levels in the plasma, and/or other pro-inflammatory cytokines, include without limitation, inflammatory bowel disease (IBD), psoriatis arthritis, ankylosing spondylitis and juvenile RA.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes.

Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., Clinical Immunol Immunopathol., 55:382 (1990)). In studies using cultured rheumatoid synovial cells, IL-1 is a more potent inducer of stromelysin than is TNF-α (Firestein, Am. J. Pathol., 140: 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, Eur. Cytokine Netw., 5:517-531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., J. Immunol., 136:40 (1986)). Beutler et al. (J. Immunol., 135:3969 (1985)) discussed the role of IL-1 in cachexia. Baracos et al. (New Eng. J. Med., 308:553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., Lymphokine Cytokine Res. 11:253 (1992); and Cooper, Clin. Exp. Immunol., 898:244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195-223 (1995)). These approaches block the effects of TNF-α and IL-1 by either protein sequestration or receptor antagonism.

Yet another approach to block the effect of TNF-α has been to modulate the activity of the p38 kinase enzyme. For example, the PCT publication, WO 04/010995, published on Feb. 5, 2004, describes fused heteroaryl derivatives for use as P38 kinase inhibitors in the treatment of I.A. rheumatoid arthritis; PCT publication, WO 2005/009937, published on Feb. 3, 2005, describes 5-membered heterocycle-based P38 kinase inhibitors; U.S. Pat. No. 6,635,644, issued Oct. 21, 2003, describes fused nitrogen-containing bicyclic ring systems as P38 inhibitors; and U.S. Pat. No. 6,794,380, issued Sep. 21, 2004, describes amide derivatives as P38 inhibitors. Inspite of the current attempts at finding a suitable therapeutic agent to treat inflammatory conditions, there remains a need to find new and/or more effective therapeutic agents for these conditions.

BRIEF DESCRIPTION OF THE INVENTION

The present invention provides a new class of compounds useful in the prophylaxis and treatment of inflammatory conditions, including TNF-α, IL-1β, IL-6 and/or IL-8 mediated diseases and other maladies, such as pain and diabetes. In particular, the compounds of the invention are useful for the prophylaxis and treatment of diseases or conditions related to the activity of p38 map kinase. The invention further comprises pharmaceutical compositions comprising the compounds, methods for the prophylaxis and treatment of TNF-α, IL-1β, IL-6 and/or IL-8 mediated diseases, such as inflammation, pain and diabetes using the compounds and compositions of the invention.

The compounds provided by the invention, including stereoisomers, tautomers, solvates, pharmaceutically acceptable salts, derivatives or prodrugs thereof, are defined by general Formula I

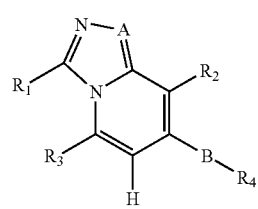

wherein A, B, $R^1$, $R^2$, $R^3$ and $R^4$ are as described below. The present invention also provides methods for making compounds of Formula I, and intermediates useful in such procedures.

The compounds provided by the invention are capable of modulating the p38 kinase enzyme. To this end, the compounds of the invention may be used to attenuate, alleviate or therapeutically or prophylactically treat acute and/or chronic treatment of p38 kinase mediated diseases, such as those described herein. The invention further provides pharmaceutical compositions, also commonly referred to as "medicaments", comprising one or more of the compounds of the invention in combination with one or more pharmaceutically acceptable carrier(s) or excipient(s).

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In one embodiment of the invention, the compounds, including stereoisomers, tautomers, solvates, pharmaceutically acceptable salts, derivatives or prodrugs thereof, are defined by general Formula I:

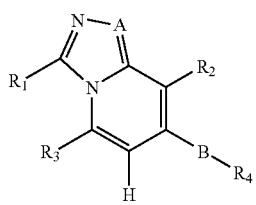

I wherein

A is $CR^5$ or N;

B is a direct bond, —$(CR^5R^6)_m$—, —C(=O)—, —O—, or —S(=O)$_m$—, wherein m is 0, 1 or 2;

$R^1$ is —$(CR^7R^7)_nX$ or —$(CR^7R^8)_nX$, wherein n is 0, 1 or 2 and X is $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$, or X is $C_{1-10}$alkyl optionally substituted with one or more substituents of $R^9$, or X is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^5$, $R^8$ or $R^9$;

each of $R^2$ and $R^3$, independently, is H, halo, haloalkyl, $NO_2$, CN, $OR^7$, $SR^7$, $NR^7R^7$, $NR^7R^8$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;

$R^4$ is a partially or fully saturated or unsaturated 3-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein said ring system is substituted independently with one or more substituents of $R^{10}$, $R^{11}$, $R^{16}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{10}$, $NR^{10}C(S)R^{10}$, $NR^{10}C(S)R^{11}$, $NR^{10}C(O)NR^{10}R^{10}$, $NR^{10}C(S)R^{11}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

each of $R^5$ and $R^6$, independently, is H, halo, haloalkyl, $NO_2$, CN, $OR^7$, $NR^7R^7$ or $C_{1-10}$-alkyl, the $C_{1-10}$-alkyl optionally substituted with one or more substituents of $R^8$ or $R^9$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-5 substituents of $R^9$;

$R^9$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, NR$^{12}$(COOR$^{12}$), OC(O)NR$^{12}$, OC(O)NR$^{12}$R$^{12}$, S(O)$_2$R$^{11}$, S(O)$_2$R$^{12}$, S(O)$_2$NR$^{11}$R$^{12}$, S(O)$_2$NR$^{12}$R$^{12}$, NR$^{12}$S(O)$_2$ NR$^{11}$R$^{12}$, NR$^{12}$S(O)$_2$NR$^{12}$R$^{12}$, NR$^{12}$S(O)$_2$R$^{11}$, NR$^{12}$S(O)$_2$ R$^{12}$, NR$^{12}$S(O)$_2$R$^{11}$ or NR$^{12}$S(O)$_2$R$^{12}$;

R$^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^{12}$, R$^{13}$, R$^{14}$ or R$^{16}$;

alternatively, R$^{10}$ and R$^{11}$ taken together with the atom to which they are attached form a partially or fully saturated or unsaturated 5-6 membered ring of carbon atoms optionally including 1-3 heteroatoms selected from O, N, or S, and the ring optionally substituted independently with 1-5 substituents of R$^{12}$, R$^{13}$, R$^{14}$ or R$^{16}$;

R$^{12}$ is H, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkyl, each of which is optionally substituted independently with 1-5 substituents of R$^{13}$, R$^{14}$, R$^{15}$ or R$^{16}$;

R$^{13}$ is NR$^{14}$R$^{15}$, NR$^{15}$R$^{15}$, OR$^{14}$, SR$^{14}$, OR$^{15}$; SR$^{15}$, C(O) R$^{14}$, OC(O)R$^{14}$, COR$^{14}$, C(O)R$^{15}$, OC(O)R$^{15}$, COOR$^{15}$, C(O)NR$^{14}$R$^{15}$, C(O)NR$^{15}$R$^{15}$, NR$^{14}$C(O)R$^{14}$, NR$^{15}$C(O) R$^{14}$, NR$^{14}$C(O)R$^{15}$, NR$^{15}$C(O)R$^{15}$, NR$^{15}$C(O)NR$^{14}$R$^{15}$, NR$^{15}$C(O)NR$^{15}$R$^{15}$, NR$^{15}$(COR$^{14}$), NR$^{15}$(COOR$^{15}$), OC(O) NR$^{14}$R$^{15}$, OC(O)NR$^{15}$R$^{15}$, S(O)$_2$R$^{14}$, S(O)$_2$R$^{15}$, S(O)$_2$ NR$^{14}$R$^{15}$, S(O)$_2$NR$^{15}$R$^{15}$, NR$^{14}$S(O)$_2$NR$^{14}$R$^{15}$, NR$^{15}$S(O)$_2$ NR$^{15}$R$^{15}$, NR$^{14}$S(O)$_2$R$^{14}$ or NR$^{15}$S(O)$_2$R$^{15}$;

R$^{14}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^{15}$ or R$^{16}$;

R$^{15}$ is H or C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkoxyl, each of which is optionally substituted independently with 1-5 substituents of R$^{16}$; and R$^{16}$ is H, halo, haloalkyl, CN, OH, NO$_2$, NH$_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment of the invention, the compounds, including stereoisomers, tautomers, solvates and pharmaceutically acceptable salts thereof, are defined by general Formula IA:

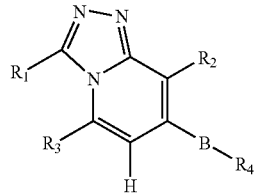

wherein B, R$^1$, R$^2$, R$^3$ and R$^4$ are as defined in the embodiment above.

In another embodiment, the compounds provided herewith, or stereoisomers, tautomers, solvates, pharmaceutically acceptable salts, derivatives or prodrugs thereof, are generally defined by Formula II

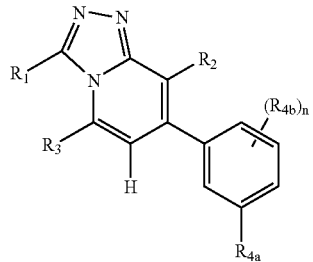

wherein

R$^1$ is —(CR$^7$R$^7$)$_n$X or —(CR$^7$R$^8$)$_n$X, wherein n is 0, 1 or 2 and X is NR$^7$R$^7$, NR$^7$R$^8$, OR$^7$, SR$^7$, OR$^8$, SR$^8$, C(O)R$^7$, OC(O)R$^7$, COOR$^7$, C(O)R$^8$, OC(O)R$^8$, COOR$^8$, C(O) NR$^7$R$^7$, C(S)NR$^7$R', NR$^7$C(O)R$^7$, NR$^7$C(S)R$^7$, NR$^7$C(O) NR$^7$R$^7$, NR$^7$C(S)NR$^7$R$^7$, NR$^7$(COOR$^7$), OC(O)NR$^7$R$^7$, C(O)NR$^7$R$^8$, C(S)NR$^7$R$^8$, NR$^7$C(O)R$^8$, NR$^7$C(S)R$^8$, NR$^7$C (O)NR$^7$R$^8$, NR$^7$C(S)NR$^7$R$^8$, NR$^7$(COOR$^8$), OC(O)NR$^7$R$^8$, S(O)$_2$R$^7$, S(O)$_2$NR$^7$R$^7$, NR$^7$S(O)$_2$NR$^7$R$^7$, NR$^7$S(O)$_2$R$^7$, S(O)$_2$R$^8$, S(O)$_2$NR$^7$R$^8$, NR$^7$S(O)$_2$NR$^7$R$^8$ or NR$^7$S(O)$_2$R$^8$, or X is C$_{1-10}$alkyl optionally substituted with one or more substituents of R$^9$, or X is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of R$^5$, R$^8$ or R$^9$;

R$^2$ is H, halo, haloalkyl, NO$_2$, OR$^7$, NR$^7$R$^7$ or C$_{1-10}$-alkyl;

R$^3$ is H, halo, haloalkyl, NO$_2$, CN, OR$^7$, NR$^7$R$^7$ or C$_{1-10}$alkyl;

R$^{4a}$ is NR$^{10}$R$^{10}$, NR$^{10}$R$^{11}$, C(O)NR$^{10}$R$^{10}$, C(O)NR$^{10}$R$^{11}$, NR$^{10}$C(O)R$^{10}$, NR$^{10}$C(O)R$^{11}$, NR$^{10}$C(O)NR$^{10}$R$^{10}$, NR$^{10}$C (O)NR$^{10}$R$^{11}$, S(O)$_2$NR$^{10}$R$^{10}$, S(O)$_2$NR$^{10}$R$^{11}$, NR$^{10}$S(O)$_2$ NR$^{10}$R$^{11}$, NR$^{10}$S(O)$_2$R$^{10}$ or NR$^{10}$S(O)$_2$R$^{11}$;

each R$^{4b}$, independently, is halo, haloalkyl, CN, NO$_2$, NH$_2$, C$_{1-10}$-alkyl, C$_{1-10}$-alkoxyl, C$_{2-10}$-alkenyl, C$_{2-10}$-alkynyl or C$_{3-10}$-cycloalkyl;

R$^7$ is H, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with one or more substituents of NR$^8$R$^9$, NR$^9$R$^9$, OR$^8$, SR$^8$, OR$^9$, SR$^9$, C(O)

$R^8$, OC(O)$R^8$, COO$R^8$, C(O)$R^9$, OC(O)$R^9$, COO$R^9$, C(O)NR$^8$R$^9$, C(O)NR$^9$R$^9$, NR$^9$C(O)R$^8$, NR$^9$C(O)R$^9$, NR$^9$C(O)NR$^8$R$^9$, NR$^9$C(O)NR$^9$R$^9$, NR$^9$(COOR$^8$), NR$^9$(COOR$^9$), OC(O)NR$^8$R$^9$, OC(O)NR$^9$R$^9$, S(O)$_2$R$^8$, S(O)$_2$NR$^8$R$^9$, S(O)$_2$R$^9$, S(O)$_2$NR$^9$R$^9$, NR$^9$S(O)$_2$NR$^8$R$^9$, NR$^9$S(O)$_2$NR$^9$R$^9$, NR$^9$S(O)$_2$R$^8$, NR$^9$S(O)$_2$R$^9$, R$^8$ or R$^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^9$, oxo, NR$^9$R$^9$, OR$^9$, SR$^9$, C(O)R$^9$, COOR$^9$, C(O)NR$^9$R$^9$, NR$^9$C(O)R$^9$, NR$^9$C(O)NR$^9$R$^9$, OC(O)NR$^9$R$^9$, S(O)$_2$R$^9$, S(O)$_2$NR$^9$R$^9$, NR$^9$S(O)$_2$R$^9$, or a partially or fully saturated or unsaturated 5-6 membered ring of carbon atoms optionally including 1-3 heteroatoms selected from O, N, or S, and optionally substituted independently with 1-3 substituents of R$^9$;

alternatively, R$^7$ and R$^8$ taken together with the atom to which they are attached form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-5 substituents of R$^9$;

$R^9$ is H, halo, haloalkyl, CN, OH, NO$_2$, NH$_2$, acetyl, oxo, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and each ring of said ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, NO$_2$, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with one or more substituents of R$^{11}$, R$^{12}$ or R$^{16}$, NR$^{11}$R$^{12}$, NR$^{12}$R$^{12}$, OR$^{11}$, SR$^{11}$, OR$^{12}$, SR$^{12}$, C(O)R$^{11}$, OC(O)R$^{11}$, COOR$^{11}$, C(O)R$^{12}$, OC(O)R$^{12}$, COOR$^{12}$, C(O)NR$^{11}$R$^{12}$, NR$^{12}$C(O)R$^{11}$, C(O)NR$^{12}$R$^{12}$, NR$^{12}$C(O)R$^{12}$, NR$^{12}$C(O)NR$^{11}$R$^{12}$, NR$^{12}$C(O)NR$^{12}$R$^{12}$, NR$^{12}$(COOR$^{11}$), NR$^{12}$(COOR$^{12}$), OC(O)NR$^{11}$R$^{12}$, OC(O)NR$^{12}$R$^{12}$, S(O)$_2$R$^{11}$, S(O)$_2$R$^{12}$, S(O)$_2$NR$^{11}$R$^{12}$, S(O)$_2$NR$^{12}$R$^{12}$, NR$^{12}$S(O)$_2$NR$^{11}$R$^{12}$, NR$^{12}$S(O)$_2$NR$^{12}$R$^{12}$, NR$^{12}$S(O)$_2$R$^{11}$, NR$^{12}$S(O)$_2$R$^{12}$, NR$^{12}$S(O)$_2$R$^{11}$ or NR$^{12}$S(O)$_2$R$^{12}$;

$R^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^{12}$, R$^{13}$, R$^{14}$ or R$^{16}$;

alternatively, R$^{10}$ and R$^{11}$ taken together form a partially or fully saturated or unsaturated 5-6 membered ring of carbon atoms optionally including 1-3 heteroatoms selected from O, N, or S, and the ring optionally substituted independently with 1-5 substituents of R$^{12}$, R$^{13}$, R$^{14}$ or R$^{16}$;

$R^{12}$ is H, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkyl, each of which is optionally substituted independently with 1-5 substituents of R$^{13}$, R$^{14}$, R$^{15}$ or R$^{16}$;

$R^{13}$ is NR$^{14}$R$^{15}$, NR$^{15}$R$^{15}$, OR$^{14}$, SR$^{14}$, OR$^{15}$, SR$^{15}$, C(O)R$^{14}$, OC(O)R$^{14}$, COOR$^{14}$, C(O)R$^{15}$, OC(O)R$^{15}$, COOR$^{15}$, C(O)NR$^{14}$R$^{15}$, C(O)NR$^{15}$R$^{15}$, NR$^{14}$C(O)R$^{14}$, NR$^{15}$C(O)R$^{14}$, NR$^{14}$C(O)R$^{15}$, NR$^{15}$C(O)R$^{15}$, NR$^{15}$C(O)NR$^{14}$R$^{15}$, NR$^{15}$C(O)NR$^{15}$R$^{15}$, NR$^{15}$(COOR$^{14}$), NR$^{15}$(COOR$^{15}$), OC(O)NR$^{14}$R$^{15}$, OC(O)NR$^{15}$R$^{15}$, S(O)$_2$R$^{14}$, S(O)$_2$R$^{15}$, S(O)$_2$NR$^{14}$R$^{15}$, S(O)$_2$NR$^{15}$R$^{15}$, NR$^{14}$S(O)$_2$NR$^{14}$R$^{15}$, NR$^{15}$S(O)$_2$NR$^{15}$R$^{15}$, NR$^{14}$S(O)$_2$R$^{14}$ or NR$^{15}$S(O)$_2$R$^{15}$;

$R^{14}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^{15}$ or R$^{16}$;

$R^{15}$ is H or C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkoxyl, each of which is optionally substituted independently with 1-5 substituents of R$^{16}$;

$R^{16}$ is H, halo, haloalkyl, CN, OH, NO$_2$, NH$_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl; and n is 1, 2 or 3.

In another embodiment, the compounds of Formula II include compounds wherein R$^1$ is C$_{1-10}$alkyl optionally substituted with one or more substituents of R$^9$, or R$^1$ is phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, dihydrobenzofuranyl, benzothiophenyl, benzisoxazolyl, benzopyrazolyl, benzothiazolyl or benzimidazolyl, each of which is optionally substituted as defined in claim 9;

each of R$^2$ and R$^3$, independently, is H or C$_{1-10}$-alkyl;

R$^{4a}$ is C(O)NR$^{10}$R$^{10}$, C(O)NR$^{10}$R$^{11}$, NR$^{10}$C(O)R$^{10}$, NR$^{10}$C(O)R$^{11}$, S(O)$_2$NR$^{10}$R$^{10}$, S(O)$_2$NR$^{10}$R$^{11}$, NR$^{10}$S(O)$_2$R$^{10}$ or NR$^{10}$S(O)$_2$R$^{11}$;

each R$^{4b}$, independently, is halo, haloalkyl, CN, NO$_2$, NH$_2$, C$_{1-10}$-alkyl or C$_{1-10}$-alkoxyl; and n is 1 or 2, in conjunction with any of the above or below embodiments.

In another embodiment, the invention provides compounds generally defined by Formula IIA

IIA

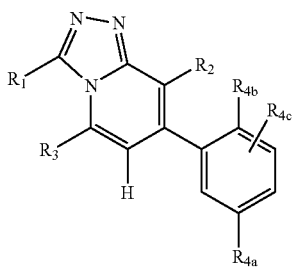

wherein $R^1$, $R^2$, $R^3$ and $R^{4a}$ are as defined in any of the above embodiments, $R^{4b}$ is halo, haloalkyl or $C_{1-10}$-alkyl and $R^{4c}$ is H, halo, haloalkyl, CN, OH, $NO_2$, $NH_2$ or $C_{1-10}$-alkyl.

In another embodiment, the invention provides compounds generally defined by Formula IIB

IIB

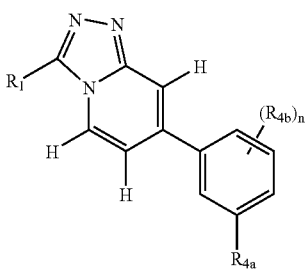

wherein $R^1$ and $R^{4a}$ are as defined in any of the above or below embodiments, each $R^{4b}$, independently, is halo, haloalkyl, CN, $NO_2$, $NH_2$, $C_{1-10}$-alkyl or $C_{1-10}$-alkoxyl and n is 1 or 2.

In another embodiment, Formula I includes compounds wherein A is $CR^5$ or N, in conjunction with any of the above or below embodiments.

In another embodiment, Formula I includes compounds wherein A is N, in conjunction with any of the above or below embodiments.

In another embodiment, Formula I includes compounds wherein A is CH, in conjunction with any of the above or below embodiments.

In another embodiment, Formula I includes compounds wherein B is a direct bond, in conjunction with any of the above or below embodiments.

In another embodiment, Formula I includes compounds wherein B is $-(CR^5R^6)_m-$, wherein m is 0, 1 or 2, in conjunction with any of the above or below embodiments.

In another embodiment, Formula I includes compounds wherein B is $-C(=O)-$, in conjunction with any of the above or below embodiments.

In another embodiment, Formula I includes compounds wherein B is $-N(R^6)-$, in conjunction with any of the above or below embodiments.

In another embodiment, Formula I includes compounds wherein B is $-O-$, in conjunction with any of the above or below embodiments.

In another embodiment, Formula I includes compounds wherein B is $-S(=O)_m-$, wherein m is 0, 1 or 2, in conjunction with any of the above or below embodiments.

In another embodiment, the compounds of Formula I or II include compounds wherein $R^1$ is $-C(R^7R^7)_nX$ or $-C(R^7R^8)_nX$, wherein n is 0, 1 or 2 and X is $NR^7R^7$, $NR^7R^8$, $OR^7$; $SR^7$, $OR^8$; $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$, $NR^7S(O)_2R^8$ or X is $C_{1-10}$alkyl optionally substituted with one or more substituents of $R^9$, in conjunction with any of the above or below embodiments.

In another embodiment, the compounds of Formula I or II include compounds wherein $R^1$ is $-C(R^7R^7)_nX$ or $-C(R^7R^8)_nX$, wherein n is 0, 1 or 2 and X is $C_{1-10}$alkyl optionally substituted with one or more substituents of $R^9$, or X is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^5$, $R^8$ or $R^9$, in conjunction with any of the above or below embodiments.

In another embodiment, the compounds of Formula I or II include compounds wherein $R^1$ is $C_{1-10}$alkyl optionally substituted with one or more substituents of $R^9$, $NR^7R^7$, $NR^7R^7R^8$, $OR^7$, $SR^7$, $OR^8$, $SR^8$, $C(O)R^7$, $C(O)R^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $S(O)_2NR^7R^7$, $NR^7S(O)_2NR^7R^7$, $NR^7S(O)_2R^7$, $S(O)_2NR^7R^8$, $NR^7S(O)_2NR^7R^8$, $NR^7S(O)_2R^8$ or a ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl as $R^1$, in conjunction with any of the above or below embodiments, wherein said ring system is optionally substituted independently with 1-5 substituents of $R^7$, $R^8$, $R^9$, oxo, $OR^7$, $SR^7$, $C(O)R^7$, $NR^7R^7$, $NR^7R^8$, $OR^8$, $SR^8$, $C(O)R^8$, $COOR^7$, $OC(O)R^7$, $COOR^8$, $OC(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $S(O)_2NR^7R^7$, $S(O)_2NR^7R^8$, $NR^7S(O)_2NR^7R^7$ or $NR^7S(O)_2NR^7R^8$.

In another embodiment, the compounds of Formula I or II include compounds wherein $R^1$ is $C_{1-10}$alkyl optionally substituted with one or more substituents of $R^9$, $OR^7$, $SR^7$, $OR^8$, $SR^8$, $C(O)R^7$, $C(O)R^8$, $C(O)NR^7R^7$, $NR^7C(O)R^7$, $NR^7C(O)NR^7R^7$, $NR^7(COOR^7)$, $C(O)NR^7R^8$, $NR^7C(O)R^8$, $NR^7C(O)NR^7R^8$, $NR^7(COOR^8)$, $S(O)_2NR^7R^7$, $NR^7S(O)_2NR^7R^7$, $NR^7S(O)_2R^7$, $S(O)_2NR^7R^8$, $NR^7S(O)_2NR^7R^8$, $NR^7S(O)_2R^8$ or a ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring system is optionally substituted independently with 1-3 substituents of $R^7$, $R^8$, $R^9$, oxo, $OR^7$, $SR^7$, $C(O)R^7$, $NR^7R^7$, $NR^7R^8$, $OR^8$, $SR^8$, $C(O)R^8$, $COOR^7$, $OC(O)R^7$, $COOR^8$, OC(O)R$^8$, C(O)NR$^7$R$^7$, C(O)NR$^7$R$^8$, NR$^7$C(O)R$^7$, NR$^7$C(O)R$^8$, NR$^7$C(O)NR$^7$R$^7$, NR$^7$C(O)NR$^7$R$^8$, S(O)$_2$NR$^7$R$^7$, S(O)$_2$NR$^7$R$^8$, NR$^7$S(O)$_2$NR$^7$R$^7$ or NR$^7$S(O)$_2$NR$^7$R$^8$, in conjunction with any of the above or below embodiments.

In another embodiment, the compounds of Formula I or II include compounds wherein R$^2$ is H, halo, haloalkyl, NO$_2$, CN, OR$^7$, SR$^7$, NR$^7$R$^8$, C(O)R$^7$, C$_{1-10}$-alkyl, C$_{2-10}$-alkenyl, C$_{2-10}$-alkynyl, C$_{3-10}$-cycloalkyl or C$_{4-10}$-cycloalkenyl, in conjunction with any of the above or below embodiments.

In another embodiment, the compounds of Formula I or II include compounds wherein R$^2$ is H, halo, haloalkyl, NO$_2$, OR$^7$, SR$^7$, NR$^7$R$^8$, C(O)R$^7$, C$_{1-10}$-alkyl, C$_{2-10}$-alkenyl, C$_{2-10}$-alkynyl, C$_{3-10}$-cycloalkyl or C$_{4-10}$-cycloalkenyl, in conjunction with any of the above or below embodiments.

In another embodiment, the compounds of Formula I or II include compounds wherein R$^2$ is H, halo, haloalkyl, NO$_2$, OR$^7$, SR$^7$, NR$^7$R$^8$, C(O)R$^7$ or C$_{1-10}$-alkyl, in conjunction with any of the above or below embodiments.

In another embodiment, the compounds of Formula I or II include compounds wherein R$^2$ is H or C$_{1-10}$-alkyl, in conjunction with any of the above or below embodiments.

In another embodiment, the compounds of Formula I or II include compounds wherein R$^2$ is H, in conjunction with any of the above or below embodiments.

In another embodiment, the compounds of Formula I or II include compounds wherein R$^3$ is H, halo, haloalkyl, NO$_2$, CN, OR$^7$, SR$^7$, NR$^7$R$^8$, C(O)R$^7$, C$_{1-10}$-alkyl, C$_{2-10}$-alkenyl, C$_{2-10}$-alkynyl, C$_{3-10}$-cycloalkyl or C$_{4-10}$-cycloalkenyl, in conjunction with any of the above or below embodiments.

In another embodiment, the compounds of Formula I or II include compounds wherein R$^3$ is H or C$_{1-10}$alkyl, in conjunction with any of the above or below embodiments.

In another embodiment, the compounds of Formula I or II include compounds wherein R$^3$ is H, in conjunction with any of the above or below embodiments.

In another embodiment, the compounds of Formula I or II include compounds wherein R$^4$ includes one or more substituents of R$^{10}$, R$^{11}$, R$^{16}$, NR$^{10}$R$^{10}$, NR$^{10}$R$^{11}$, OR$^{10}$, SR$^{10}$, OR$^{11}$, SR$^{11}$, C(O)R$^{10}$, C(S)R$^{10}$, C(NCN)R$^{10}$, C(O)R$^{11}$, C(S)R$^{11}$, C(NCN)R$^{11}$, C(O)C(O)R$^{10}$, OC(O)R$^{10}$, COOR$^{10}$, C(O)SR$^{10}$, C(O)C(O)R$^{11}$, OC(O)R$^{11}$, COOR$^{11}$, C(O)SR$^{11}$, C(O)NR$^{10}$R$^{10}$, C(S)NR$^{10}$R$^{10}$, C(O)NR$^{10}$R$^{11}$, C(S)NR$^{10}$R$^{11}$, OC(O)NR$^{10}$R$^{11}$, NR$^{10}$C(O)R$^{10}$, NR$^{10}$C(O)R$^{11}$, NR$^{10}$C(S)R$^{10}$, NR$^{10}$C(S)R$^{11}$, NR$^{10}$C(O)NR$^{10}$R$^{10}$, NR$^{10}$C(O)NR$^{10}$R$^{11}$, NR$^{10}$(COOR$^{10}$), NR$^{10}$(COOR$^{11}$), NR$^{10}$C(O)C(O)R$^{10}$, NR$^{10}$C(O)C(O)R$^{11}$, NR$^{10}$C(O)C(O)NR$^{10}$R$^{11}$, S(O)$_2$R$^{10}$, S(O)$_2$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$, in conjunction with any of the above or below embodiments.

In another embodiment, the compounds of Formula I or II include compounds wherein R$^4$ includes least one substituent of NR$^{10}$R$^{10}$, NR$^{10}$R$^{11}$, S(O)$_2$R$^{10}$, S(O)$_2$R$^{11}$, C(O)NR$^{10}$R$^{10}$, C(S)NR$^{10}$R$^{10}$, C(O)NR$^{10}$R$^{11}$, C(S)NR$^{10}$R$^{11}$, NR$^{10}$C(O)R$^{10}$, NR$^{10}$C(S)R$^{10}$, NR$^{10}$C(O)R$^{11}$, NR$^{10}$C(S)R$^{11}$, NR$^{10}$C(O) NR$^{10}$R$^{10}$, NR$^{10}$C(O)NR$^{10}$R$^{11}$, NR$^{10}$C(S)NR$^{10}$R$^{10}$, NR$^{10}$C(S)NR$^{11}$R$^{11}$, S(O)$_2$NR$^{10}$R$^{10}$, S(O)$_2$NR$^{10}$R$^{11}$, NR$^{11}$S(O)$_2$NR$^{10}$R$^{11}$, NR$^{10}$S(O)$_2$R$^{10}$ or NR$^{10}$S(O)$_2$R$^{11}$, in conjunction with any of the above or below embodiments.

In another embodiment, the compounds of Formula I or II include two substituents on R$^4$, a first substituent of NR$^{10}$R$^{10}$, NR$^{10}$R$^{11}$, S(O)$_2$R$^{10}$, S(O)$_2$R$^{11}$, C(O)NR$^{10}$R$^{10}$, C(O)NR$^{10}$R$^{11}$, NR$^{10}$C(O)R$^{10}$, NR$^{10}$C(O)R$^{11}$, NR$^{10}$C(O)NR$^{10}$R$^{10}$, NR$^{10}$C(O)NR$^{10}$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$ and a second substituent of R$^6$, in conjunction with any of the above or below embodiments.

In another embodiment, the compounds of Formula I or II include compounds wherein R$^4$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, dihydrobenzofuranyl, benzothiophenyl, benzoxazolyl, benzopyrazolyl, benzisoxazolyl, benzothiazolyl or benzimidazolyl, each of which has one substituent of NR$^{10}$R$^{10}$, NR$^{10}$R$^{11}$, C(O)R$^{10}$, OC(O)R$^{10}$, COOR$^{10}$, C(O)R$^{11}$, OC(O)R$^{11}$, COOR$^{11}$, C(O)SR$^{10}$, C(O)SR$^{11}$, C(O)NR$^{10}$R$^{10}$, C(S)NR$^{10}$R$^{10}$, C(O)NR$^{10}$R$^{11}$, C(S)NR$^{10}$R$^{11}$, NR$^{10}$C(O)R$^{10}$, NR$^{10}$C(S)R$^{10}$, NR$^{10}$C(O)R$^{11}$, NR$^{10}$C(S)R$^{11}$, NR$^{10}$C(O)NR$^{10}$R$^{10}$, NR$^{10}$C(O)NR$^{10}$R$^{11}$, NR$^{10}$C(S)NR$^{10}$R$^{10}$, NR$^{10}$C(S)NR$^{10}$R$^{11}$, NR$^{10}$(COOR$^{10}$), NR$^{10}$(COOR$^{11}$), OC(O)NR$^{10}$R$^{11}$, S(O)$_2$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$, and 1-3 optional substituents of R$^{10}$, R$^{11}$, R$^{16}$, NR$^{10}$R$^{10}$, NR$^{10}$R$^{11}$, OR$^{10}$, SR$^{10}$, OR$^{11}$, SR$^{11}$, C(O)R$^{10}$, C(S)R$^{10}$, C(NCN)R$^{10}$, C(O)R$^{11}$, C(S)R$^{11}$, C(NCN)R$^{11}$, C(O)C(O)R$^{10}$, OC(O)R$^{10}$, COOR$^{10}$, C(O)SR$^{10}$, C(O)C(O)R$^{11}$, OC(O)R$^{11}$, COOR$^{11}$, C(O)SR$^{11}$, C(O)NR$^{10}$R$^{10}$, C(S)NR$^{10}$R$^{10}$, C(O)NR$^{10}$R$^{11}$, C(S)NR$^{10}$R$^{11}$, OC(O)NR$^{10}$R$^{11}$, NR$^{10}$C(O)R$^{10}$, NR$^{10}$C(O)R$^{11}$, NR$^{10}$C(S)R$^{10}$, NR$^{10}$C(S)R$^{11}$, NR$^{10}$C(O)NR$^{10}$R$^{10}$, NR$^{10}$C(O)NR$^{10}$R$^{11}$, NR$^{10}$C(S) NR$^{10}$R$^{10}$, NR$^{10}$C(S)NR$^{10}$R$^{11}$, NR$^{10}$(COOR$^{10}$), NR$^{10}$ (COOR$^{11}$), NR$^{10}$C(O)C(O)R$^{10}$, NR$^{10}$C(O)C(O)R$^{11}$, NR$^{10}$C (O)C(O)NR$^{10}$R$^{11}$, S(O)$_2$R$^{10}$, S(O)$_2$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$, in conjunction with any of the above or below embodiments.

In another embodiment, the compounds of Formula I or II include one substituent of NR$^{10}$R$^{10}$, NR$^{10}$R$^{11}$, C(O) NR$^{10}$R$^{10}$, C(S)NR$^{10}$R$^{10}$, C(O)NR$^{10}$R$^{11}$, C(S)NR$^{10}$R$^{11}$, NR$^{10}$C(O)R$^{10}$, NR$^{10}$C(S)R$^{10}$, NR$^{10}$C(O)R$^{11}$, NR$^{10}$C(S)R$^{11}$, NR$^{10}$C(O)NR$^{10}$R$^{10}$, NR$^{10}$C(O)NR$^{10}$R$^{11}$, NR$^{10}$C(S) NR$^{10}$R$^{10}$, NR$^{10}$C(S)NR$^{10}$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$ and 0-3 substituents of R$^{16}$, on R$^4$, in conjunction with any of the above or below embodiments.

The compounds of the invention contain at least one substituent other than hydrogen, as noted in exemplary embodiments above, on R$^4$. The invention does not include those compounds in which R$^4$ has no substituents attached thereto, other than attachment to B or directly to the pyridine core of Formulas I and II.

In another embodiment, the compounds of Formula I include H, halo, haloalkyl, NO$_2$, CN, NR$^7$R$^7$, NR$^7$R$^8$, OR$^7$, SR$^7$, C(O)R$^7$, C$_{1-10}$-alkyl, C$_{2-10}$-alkenyl, C$_{2-10}$-alkynyl, C$_{3-10}$-cycloalkyl or C$_{4-10}$-cycloalkenyl as R$^5$, in conjunction with any of the above or below embodiments.

In another embodiment, the compounds of Formula I include H or C$_{1-10}$-alkyl as R$^5$, in conjunction with any of the above or below embodiments.

In another embodiment, there are provided compounds of Formula I wherein wherein B is a direct bond;

R$^1$ is C$_{1-10}$alkyl optionally substituted with one or more substituents of R$^9$, NR$^7$R$^7$, NR$^7$R$^8$, OR$^7$, OR$^8$, C(O)R$^7$, C(O) R$^8$, C(O)NR$^7$R$^7$, NR$^7$C(O)R$^7$, NR$^7$C(O)NR$^7$R$^7$, C(O) NR$^7$R$^8$, NR$^7$C(O)R$^8$, NR$^7$C(O)NR$^7$R$^8$, S(O)$_2$NR$^7$R$^7$, NR$^7$S (O)$_2$NR$^7$R$^7$, NR$^7$S(O)$_2$R$^7$, S(O)$_2$NR$^7$R$^8$, NR$^7$S(O)$_2$NR$^7$R$^8$, NR$^7$S(O)$_2$R$^8$ or R$^1$ is a ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring system is optionally substituted independently with 1-3 substituents of $R^7$, $R^8$, $R^9$, oxo, $OR^7$, $SR^7$, $C(O)R^7$, $NR^7R^7$, $NR^7R^8$, $OR^8$, $SR^8$, $C(O)R^8$, $COOR^7$, $OC(O)R^7$, $COOR^8$, $OC(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $S(O)_2NR^7R^7$, $S(O)_2NR^7R^8$, $NR^7S(O)_2NR^7R^7$ or $NR^7S(O)_2NR^7R^8$;

each of $R^2$ and $R^3$, independently, is H or $C_{1-10}$-alkyl;

$R^4$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, dihydrobenzofuranyl, benzothiophenyl, benzoxazolyl, benzopyrazolyl, benzisoxazolyl, benzothiazolyl or benzimidazolyl, said $R^4$ substituted with one substituent of $NR^{10}R^{10}$, $NR^{10}R^{11}$, $C(O)NR^{10}R^{10}$, $C(O)NR^{10}R^{11}$, $NR^{10}C(O)R^{10}$, $NR^{10}C(O)R^{11}$, $NR^{10}C(O)NR^{10}R^{10}$, $NR^{10}C(O)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$ and 0-3 substituents of $R^{16}$;

$R^7$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together with the atom to which they are attached form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl or $C_{3-10}$-cycloalkyl, each of the $C_{1-10}$-alkyl, $C_{2-10}$-alkenyl, and $C_{3-10}$-cycloalkyl optionally comprising 1-4 heteroatoms selected from N, O and S and optionally substituted with 1-3 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{11}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-3 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{14}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-3 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, NO$_2$, NH$_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

In another embodiment, the compounds of Formulas I or II include compounds wherein R$^4$ is

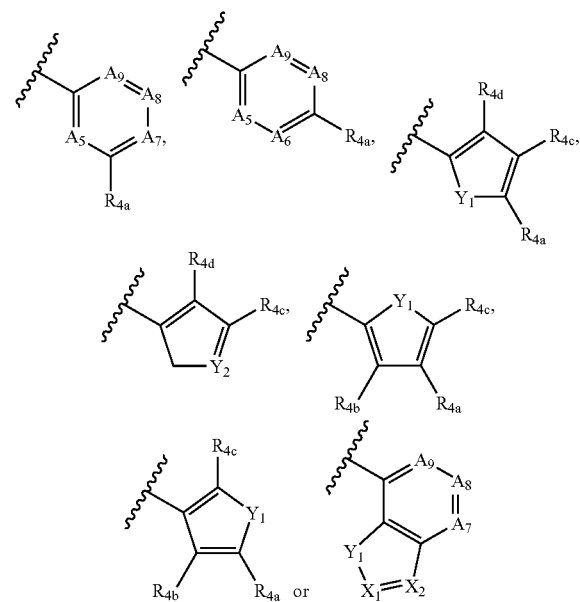

wherein
each of A$^5$, A$^6$, and A$^7$ is, independently, CR$^{4b}$ or N;
A$^8$ is CR$^{4c}$ or N; and
A$^9$ is CR$^{4d}$ or N;
X$^1$ is, independently, CR$^{4b}$ or N;
X$^2$ is CR$^{4a}$;
Y$^1$ is NH, O or S;
Y$^2$ is NR$^{4a}$;
R$^{4a}$ is NR$^{10}$R$^{10}$, NR$^{10}$R$^{11}$, C(O)NR$^{10}$R$^{10}$, C(O)NR$^{10}$R$^{11}$, NR$^{10}$C(O)R$^{10}$, NR$^{10}$C(O)R$^{11}$, NR$^{10}$(O)NR$^{10}$R$^{10}$, NR$^{10}$C(O)NR$^{10}$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$;
R$^{4b}$ is H, halo, haloalkyl, CN, NO$_2$, NH$_2$, C$_{1-10}$-alkyl, C$_{1-10}$-alkoxyl, C$_{2-10}$-alkenyl, C$_{2-10}$-alkynyl or C$_{3-10}$-cycloalkyl;
R$^{4c}$ is H, halo, haloalkyl, CN, NO$_2$, NH$_2$, C$_{1-10}$-alkyl, C$_{1-10}$-alkoxyl, C$_{2-10}$-alkenyl, C$_{2-10}$-alkynyl or C$_{3-10}$-cycloalkyl;
R$^{4d}$ is H, halo, haloalkyl, CN, NO$_2$, NH$_2$, C$_{1-10}$-alkyl, C$_{1-10}$-alkoxyl, C$_{2-10}$-alkenyl, C$_{2-10}$-alkynyl or C$_{3-10}$-cycloalkyl; and
alternatively, R$^{4c}$ and R$^{4d}$ taken together with the atoms to which they are attached form a 5- or 6-membered aromatic ring system optionally comprising 1-3 heteroatoms selected from N, O and S, and the ring system optionally substituted with 1-3 substituents of halo, haloalkyl, CN, NO$_2$, NH$_2$, C$_{1-10}$-alkyl, C$_{2-10}$-alkenyl, C$_{2-10}$-alkynyl or C$_{3-10}$-cycloalkyl, in conjunction with any of the above or below embodiments.

In another embodiment, the compounds of Formulas I or II include compounds wherein R$^4$ is

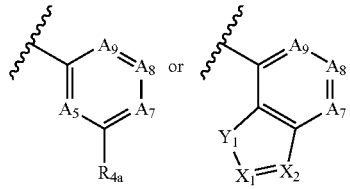

wherein
each of A$^5$ and A$^7$ is, independently, CR$^{4b}$ or N;
A$^8$ is CR$^{4c}$ or N; and
A$^9$ is CR$^{4d}$ or N;
X$^1$ is, independently, CR$^{4b}$ or N;
X$^2$ is CR$^{4a}$;
Y$^1$ is NH, O or S;
R$^{4a}$ is NR$^{10}$R$^{10}$, NR$^{10}$R$^{11}$, C(O)NR$^{10}$R$^{10}$, C(O)NR$^{10}$R$^{11}$, NR$^{10}$C(O)R$^{10}$, NR$^{10}$C(O)R$^{11}$, NR$^{10}$C(O)NR$^{10}$R$^{10}$, NR$^{10}$C(O)NR$^{10}$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$;
R$^{4b}$ is H, halo, haloalkyl, CN, NO$_2$, NH$_2$, C$_{1-10}$-alkyl, C$_{1-10}$-alkoxyl, C$_{2-10}$-alkenyl, C$_{2-10}$-alkynyl or C$_{3-10}$-cycloalkyl;
R$^{4c}$ is H, halo, haloalkyl, CN, NO$_2$, NH$_2$, C$_{1-10}$-alkyl, C$_{1-10}$-alkoxyl, C$_{2-10}$-alkenyl, C$_{2-10}$-alkynyl or C$_{3-10}$-cycloalkyl;
R$^{4d}$ is H, halo, haloalkyl, CN, NO$_2$, NH$_2$, C$_{1-10}$-alkyl, C$_{1-10}$-alkoxyl, C$_{2-10}$-alkenyl, C$_{2-10}$-alkynyl or C$_{3-10}$-cycloalkyl; and
alternatively, R$^{4c}$ and R$^{4d}$ taken together with the atoms to which they are attached form a 5- or 6-membered aromatic ring system optionally comprising 1-3 heteroatoms selected from N, O and S, and the ring system optionally substituted with 1-3 substituents of halo, haloalkyl, CN, NO$_2$, NH$_2$, C$_{1-10}$-alkyl, C$_{2-10}$-alkenyl, C$_{2-10}$-alkynyl or C$_{3-10}$-cycloalkyl, in conjunction with any of the above or below embodiments.

In yet another embodiment, the compounds of Formulas I and II include the examples described hereinbelow.

DEFINITIONS

The following definitions should assist in understanding the invention described herein.

The term "comprising" is meant to be open ended, including the indicated component(s), but not excluding other elements.

The term "C$_{\alpha-\beta}$alkyl", when used either alone or within other terms such as "haloalkyl" and "alkylamino", embraces linear or branched radicals having α to β number of carbon atoms (such as C$_1$-C$_{10}$). Examples of such radicals include methyl, ethyl, n-propyl, isopropyl, n-butyl, isobutyl, sec-butyl, tert-butyl, pentyl, isoamyl, hexyl and the like. The term "alkylenyl" embraces bridging divalent alkyl radicals such as methylenyl and ethylenyl.

The term "alkenyl", when used alone or in combination, embraces linear or branched radicals having at least one carbon-carbon double bond in a moiety having between two and ten carbon atoms. Examples of alkenyl radicals include, without limitation, ethenyl, propenyl, allyl, propenyl, butenyl and 4-methylbutenyl. The terms "alkenyl" and "lower alkenyl", embrace radicals having "cis" and "trans" orientations, or alternatively, "E" and "Z" orientations, as appreciated by those of ordinary skill in the art.

The term "alkynyl", when used alone or in combination, denotes linear or branched radicals having at least one carbon-carbon triple bond and having two to ten carbon atoms. Examples of such radicals include, without limitation, ethynyl, propynyl (propargyl), butynyl, and the like.

The term "alkoxy" or "alkoxyl", when used alone or in combination, embraces linear or branched oxygen-containing radicals each having alkyl portions of one or more carbon atoms. Examples of such radicals include methoxy, ethoxy, propoxy, butoxy and tert-butoxy. Alkoxy radicals may be further substituted with one or more halo atoms, such as fluoro, chloro or bromo, to provide "haloalkoxy" radicals. Examples of such radicals include fluoromethoxy, chloromethoxy, trifluoromethoxy, trifluoroethoxy, fluoroethoxy and fluoropropoxy.

The term "aryl", when used alone or in combination, means a carbocyclic aromatic moiety containing one, two or even three rings wherein such rings may be attached together in a fused manner. Every ring of an "aryl" ring system need not be aromatic, and the ring(s) fused to the aromatic ring may be partially or fully unsaturated and include one or more heteroatoms selected from nitrogen, oxygen and sulfur. Thus, the term "aryl" embraces aromatic radicals such as phenyl, naphthyl, indenyl, tetrahydronaphthyl, dihydrobenzafuranyl, anthracenyl, indanyl, benzodioxazinyl, and the like. Unless otherwise specified, the "aryl" group may be substituted, such as with 1 to 5 substituents including lower alkyl, hydroxyl, halo, haloalkyl, nitro, cyano, alkoxy and lower alkylamino, and the like. Phenyl substituted with —O—CH$_2$—O— or —O—CH$_2$—CH$_2$—O— forms an aryl benzodioxolyl substituent.

The term "carbocyclic", also referred to herein as "cycloalkyl", when used alone or in combination, means a partially or fully saturated ring moiety containing one ("monocyclic"), two ("bicyclic") or even three ("tricyclic") rings wherein such rings may be attached together in a fused manner and formed from carbon atoms. Examples of saturated carbocyclic radicals include saturated 3 to 6-membered monocyclic groups such as cyclopropane, cyclobutane, cyclopentane and cyclohexane and partially saturated monocyclic groups such as cyclopentene, cyclohexene or cyclohexadiene. The partially saturated groups are also encompassed in the term "cycloalkenyl" as defined below.

The terms "ring" and "ring system" refer to a ring comprising the delineated number of atoms, the atoms being carbon or, where indicated, a heteroatom such as nitrogen, oxygen or sulfur. Where the number of atoms is not delineated, such as a "monocyclic ring system" or a "bicyclic ring system", the numbers of atoms are 3-8 for a monocyclic and 6-12 for a bicyclic ring. The ring itself, as well as any substitutents thereon, may be attached at any atom that allows a stable compound to be formed. The term "nonaromatic" ring or ring system refers to the fact that at least one, but not necessarily all, rings in a bicyclic or tricyclic ring system is nonaromatic.

The terms "partially or fully saturated or unsaturated" and "saturated or partially or fully unsaturated" with respect to each individual ring, refer to the ring either as fully aromatic (fully unsaturated), partially aromatic (or partially saturated) or fully saturated (containing no double or triple bonds therein). If not specified as such, then it is contemplated that each ring (monocyclic) in a ring system (if bicyclic or tricyclic) may either be fully aromatic, partially aromatic or fully saturated, and optionally substituted with up to 5 substituents.

The term "cycloalkenyl", when used alone or in combination, means a partially or fully saturated cycloalkyl containing one, two or even three rings in a structure having at least one carbon-carbon double bond in the structure. Examples of cycloalkenyl groups include $C_3$-$C_6$ rings, such as compounds including, without limitation, cyclopropene, cyclobutene, cyclopentene and cyclohexene. The term also includes carbocyclic groups having two or more carbon-carbon double bonds such as "cycloalkyldienyl" compounds. Examples of cycloalkyldienyl groups include, without limitation, cyclopentadiene and cycloheptadiene.

The term "halo", when used alone or in combination, means halogens such as fluorine, chlorine, bromine or iodine atoms.

The term "haloalkyl", when used alone or in combination, embraces radicals wherein any one or more of the alkyl carbon atoms is substituted with halo as defined above. For example, this term includes monohaloalkyl, dihaloalkyl and polyhaloalkyl radicals such as a perhaloalkyl. A monohaloalkyl radical, for example, may have either an iodo, bromo, chloro or fluoro atom within the radical. Dihalo and polyhaloalkyl radicals may have two or more of the same halo atoms or a combination of different halo radicals. Examples of haloalkyl radicals include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perfluoroalkyl", as used herein, refers to alkyl radicals having all hydrogen atoms replaced with fluoro atoms. Examples include trifluoromethyl and pentafluoroethyl.

The term "heteroaryl", as used herein, either alone or in combination, means a fully unsaturated (aromatic) ring moiety formed from carbon atoms and having one or more heteroatoms selected from nitrogen, oxygen and sulfur. The ring moiety or ring system may contain one ("monocyclic"), two ("bicyclic") or even three ("tricyclic") rings wherein such rings are attached together in a fused manner. Every ring of a "heteroaryl" ring system need not be aromatic, and the ring(s) fused thereto (to the heteroaromatic ring) may be partially or fully saturated and optionally include one or more heteroatoms selected from nitrogen, oxygen and sulfur. The term "heteroaryl" does not include rings having ring members of —O—O—, —O—S— or —S—S—.

Examples of heteroaryl radicals, include unsaturated 5- to 6-membered heteromonocyclyl groups containing 1 to 4 nitrogen atoms, including for example, pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, 1H-1,2,3-triazolyl, 2H-1,2,3-triazolyl] and tetrazole; unsaturated 7- to 10-membered heterobicyclyl groups containing 1 to 4 nitrogen atoms, including for example, quinolinyl, isoquinolinyl, quinazolinyl, isoquinazolinyl, aza-quinazolinyl, and the like; unsaturated 5- to 6-membered heteromonocyclic group containing an oxygen atom, for example, pyranyl, 2-furyl, 3-furyl, benzofuryl, etc.; unsaturated 5 to 6-membered heteromonocyclic group containing a sulfur atom, for example, 2-thienyl, 3-thienyl, benzothienyl, etc.; unsaturated 5- to 6-membered heteromonocyclic group containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic group containing 1 to 2 sulfur atoms and 1 to 3 nitrogen atoms, for example, thiazolyl, isothiazolyl, thiadiazolyl [e.g., 1,2,4-thiadiazolyl, 1,3,4-thiadiazolyl, 1,2,5-thiadiazolyl].

The term "heteroaryl" also embraces bicyclic radicals wherein 5- or 6-membered heteroaryl radicals are fused/condensed with aryl radicals or unsaturated condensed heterocyclic groups containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl [e.g., tetrazolo[1,5-b]pyridazinyl]; unsaturated condensed heterocyclic group containing 1 to 2 oxygen atoms and 1 to 3 nitrogen atoms [e.g. benzoxazolyl, benzoxadiazolyl]; unsaturated condensed heterocyclic group containing 1 to 2 sulfur atoms and 1 to 3 nitrogen atoms [e.g., benzothiazolyl, benzothiadiazolyl]; and saturated, partially unsaturated and unsaturated condensed heterocyclic group containing 1 to 2 oxygen or sulfur atoms [e.g. benzofuryl, benzothienyl, 2,3-dihydro-benzo[1,4]dioxinyl and dihydrobenzofuryl]. Examples of heterocyclic radicals include five to ten membered fused or unfused radicals.

The term "heterocyclic", when used alone or in combination, means a partially or fully saturated ring moiety containing one, two or even three rings wherein such rings may be attached together in a fused manner, formed from carbon atoms and including one or more heteroatoms selected from N, O or S. Examples of heterocyclic radicals include saturated 3 to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include dihydrothienyl, dihydropyranyl, dihydrofuryl and dihydrothiazolyl.

Examples of partially saturated and saturated heterocyclyl include, without limitation, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl, and the like.

The term "alkylamino" includes "N-alkylamino" where amino radicals are independently substituted with one alkyl radical. Preferred alkylamino radicals are "lower alkylamino" radicals having one to six carbon atoms. Even more preferred are lower alkylamino radicals having one to three carbon atoms. Examples of such lower alkylamino radicals include N-methylamino, and N-ethylamino, N-propylamino, N-isopropylamino and the like.

The term "dialkylamino" includes "N,N-dialkylamino" where amino radicals are independently substituted with two alkyl radicals. Preferred alkylamino radicals are "lower alkylamino" radicals having one to six carbon atoms. Even more preferred are lower alkylamino radicals having one to three carbon atoms. Examples of such lower alkylamino radicals include N,N-dimethylamino, N,N-diethylamino, and the like.

The terms "alkylthio" and "thioalkoxyl" embrace radicals containing a linear or branched alkyl radical, of one to ten carbon atoms, attached to a divalent sulfur atom. An example of "alkylthio" is methylthio, ($CH_3S-$).

The term "Formula I" includes any sub formulas, such as Formula IA and II. Similarly, the term "Formula II" includes any sub formulas, such as Formulas IIA and IIB.

The term "pharmaceutically-acceptable" when used with reference to a compound of Formulas I or II is intended to refer to a form of the compound that is safe for administration to a subject. For example, a free base, a salt form, a solvate, a hydrate, a prodrug or derivative form of a compound of Formula I or of Formula II, which has been approved for mammalian use, via oral ingestion or any other route of administration, by a governing authority or regulatory agency, such as the Food and Drug Administration (FDA) of the United States, is pharmaceutically acceptable.

Included in the compounds of Formulas I and II are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. As appreciated by those of ordinary skill in the art, salts may be formed from ionic associations, charge-charge interactions, covalent bonding, complexation, coordination, etc. The nature of the salt is not critical, provided that it is pharmaceutically acceptable.

Suitable pharmaceutically acceptable acid addition salts of compounds of Formulas I and II may be prepared from an inorganic acid or from an organic acid. Examples of such inorganic acids are hydrochloric, hydrobromic, hydroiodic, hydrofluoric, nitric, carbonic, sulfonic, sulfuric and phosphoric acid. Appropriate organic acids may be selected from aliphatic, cycloaliphatic, aromatic, arylaliphatic, heterocyclic, carboxylic and sulfonic classes of organic acids, examples of which include, without limitation, formic, acetic, adipic, butyric, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, ethanedisulfonic, benzenesulfonic, pantothenic, 2-hydroxyethanesulfonic, toluenesulfonic, sulfanilic, cyclohexylaminosulfonic, camphoric, camphorsulfonic, digluconic, cyclopentanepropionic, dodecylsulfonic, glucoheptanoic, glycerophosphonic, heptanoic, hexanoic, 2-hydroxy-ethanesulfonic, nicotinic, 2-naphthalenesulfonic, oxalic, palmoic, pectinic, persulfuric, 2-phenylpropionic, picric, pivalic propionic, succinic, thiocyanic, undecanoic, stearic, algenic, β-hydroxybutyric, salicylic, galactaric and galacturonic acid. Suitable pharmaceutically-acceptable base addition salts of compounds of Formulas I and II include metallic salts, such as salts made from aluminum, calcium, lithium, magnesium, potassium, sodium and zinc, or salts made from organic bases including, without limitation, primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, disopropylethylamine and trimethylamine. All of these salts may be prepared by conventional means from the corresponding compound of the invention by reacting, for example, the appropriate acid or base with the compound of Formulas I or II.

Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Additional examples of such salts can be found in Berge et al., J. Pharm. Sci., 66, 1 (1977). Conventional methods may be used to form the salts. For example, a phosphate salt of a compound of the invention may be made by combining the desired compound free base in a desired solvent, or combination of solvents, with phosphoric acid in a desired stoichiometric amount, at a desired temperature, typically under heat (depending upon the boiling point of the solvent). The salt can be precipitated upon cooling (slow or fast) and may crystallize (i.e., if crystalline in nature), as appreciated by those of ordinary skill in the art. Further, hemi-, mono-, di, tri- and poly-salt forms of the compounds of the present invention are also contemplated herein. Similarly, hemi-, mono-, di, tri- and poly-hydrated forms of the compounds, salts and derivatives thereof, are also contemplated herein.

The term "derivative" is broadly construed herein, and intended to encompass any salt of a compound of this invention, any ester of a compound of this invention, or any other compound, which upon administration to a patient is capable of providing (directly or indirectly) a compound of this invention, or a metabolite or residue thereof, characterized by the ability to the ability to modulate a kinase enzyme.

The term "pharmaceutically-acceptable derivative" as used herein, denotes a derivative, which is pharmaceutically acceptable.

The term "prodrug", as used herein, denotes a compound which upon administration to a subject or patient is capable of providing (directly or indirectly) a compound of this invention. Examples of prodrugs would include esterified or hydroxylated compounds where the ester or hydroxyl groups would cleave in vivo, such as in the gut, to produce a compound according to Formula I. A "pharmaceutically-acceptable prodrug" as used herein, denotes a prodrug, which is pharmaceutically acceptable. Pharmaceutically acceptable modifications to the compounds of Formula I are readily appreciated by those of ordinary skill in the art.

The compound(s) of Formula I or II may be used to treat a subject by administering the compound(s) as a pharmaceutical composition. To this end, the compound(s) can be combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount may be administered in a single dosage form or in multiple dosage forms.

The term "leaving groups" (also denoted as "LG") generally refer to groups that are displaceable by a nucleophile. Such leaving groups are known in the art. Examples of leaving groups include, but are not limited to, halides (e.g., I, Br, F, Cl), sulfonates (e.g., mesylate, tosylate), sulfides (e.g., $SCH_3$), N-hydroxsuccinimide, N-hydroxybenzotriazole, and the like. Nucleophiles are species that are capable of attacking a molecule at the point of attachment of the leaving group causing displacement of the leaving group. Nucleophiles are known in the art. Examples of nucleophilic groups include, but are not limited to, amines, thiols, alcohols, Grignard reagents, anionic species (e.g., alkoxides, amides, carbanions) and the like.

General Synthetic Procedures

The compounds of Formulas I and II can be synthesized according to the procedures described in the following Schemes 1-3, wherein the substituents are as defined for Formulas I and II, above, except where further noted. The synthetic methods described below are merely exemplary, and the compounds of the invention may also be synthesized by alternate routes as appreciated by persons of ordinary skill in the art.

The list of abbreviations below have the following meanings:

| | |
|---|---|
| ACN, MeCN | acetonitrile |
| BSA | bovine serum albumin |
| BOP | benzotriazol-1-yl-oxy hexafluorophosphate |
| CDI | carbonyldiimidazole |
| $Cs_2CO_3$ | cesium carbonate |
| $CHCl_3$ | chloroform |
| $CH_2Cl_2$, DCM | dichloromethane, methylene chloride |
| DCC | dicyclohexylcarbodiimide |
| DIC | 1,3-diisopropylcarbodiimide |
| DIEA, $(iPr)_2NEt$ | diisopropylethylamine |
| DME | dimethoxyethane |
| DMF | dimethylformamide |
| DMAP | 4-dimethylaminopyridine |
| DMSO | dimethylsulfoxide |
| EDC | 1-(3-dimethylaminopropyl)-3-ethylcarbodiimide |
| $Et_2O$ | diethyl ether |
| EtOAc | ethyl acetate |
| G, gm | gram |
| h, hr | hour |
| $H_2$ | hydrogen gas |
| $H_2O$ | water |
| HATU | O-(7-azabenzotriazol-1-yl)-N,N,N',N'-tetramethyluroniumhexafluorophosphate |
| HBr | hydrobromic acid |
| HCl | hydrochloric acid |
| HOBt | 1-hydroxybenzotriazole hydrate |
| HOAc | acetic acid |
| HPLC | high pressure liquid chromatography |
| IPA, IpOH | isopropyl alcohol |
| $K_2CO_3$ | potassium carbonate |
| KI | potassium iodide |
| LG | leaving group |
| $MgSO_4$ | magnesium sulfate |
| MS | mass spectrum |
| MeOH | methanol |
| $N_2$ | nitrogen gas |
| $NaCNBH_3$ | sodium cyanoborohydride |
| $Na_2CO_3$ | sodium carbonate |
| $NaHCO_3$ | sodium bicarbonate |
| NaH | sodium hydride |
| $NaOCH_3$ | sodium methoxide |
| NaOH | sodium hydroxide |
| $Na_2SO_4$ | sodium sulfate |
| NBS | N-bromosuccinimide |
| $NH_4Cl$ | ammonium chloride |
| $NH_4OH$ | ammonium hydroxide |
| NMP | N-methylpyrrolidinone |
| $P(t-bu)_3$ | tri(tert-butyl)phosphine |
| PBS | phospate buffered saline |
| Pd/C | palladium on carbon |
| $Pd(PPh_3)_4$ | palladium(0)triphenylphosphine tetrakis |

-continued

| | |
|---|---|
| Pd(dppf)Cl$_2$ | palladium(1,1-bisdipbenylphosphinoferrocene) II chloride |
| Pd(PhCN)$_2$Cl$_2$ | palladium di-cyanophenyl dichloride |
| Pd(OAc)$_2$ | palladium acetate |
| Pd$_2$(dba)$_3$ | tris(dibenzylideneacetone) dipalladium |
| PyBop | benzotriazol-1-yl-oxy-tripyrrolidino-phosphonium hexafluorophosphate |
| RT | room temperature |
| RBF | round-bottom flask |
| TBTU | O-benzotriazol-1-yl-N,N,N',N'-tetramethyluronium tetrafluoroborate |
| TEA, Et$_3$N | triethylamine |
| TFA | trifluoroacetic acid |
| THF | tetrahydrofuran |
| UV | ultraviolet light |

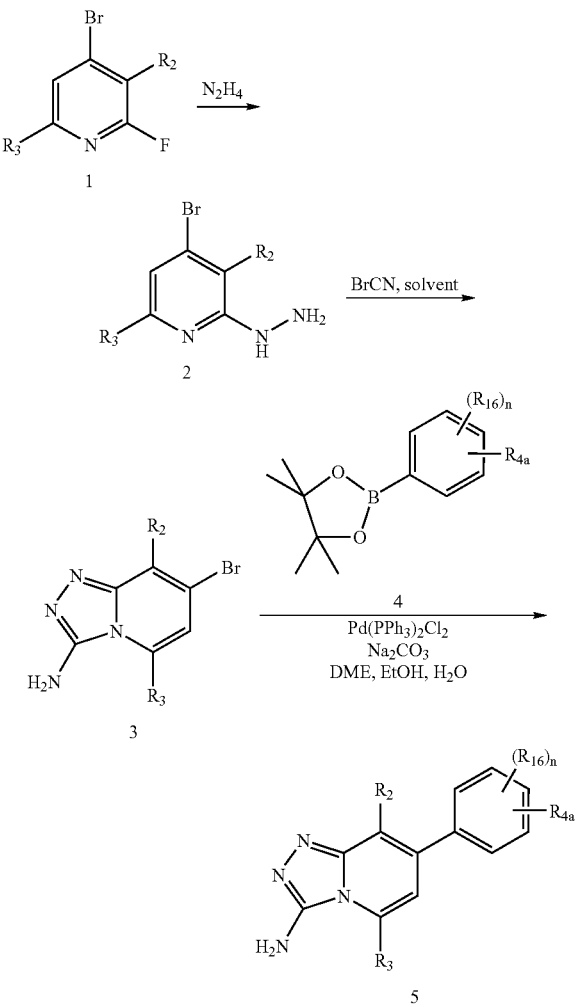

Scheme 1

Amino-substituted triazolo-pyridines 5, (where A in Formula I is N; B is a direct bond and R$^4$ as shown is a desirably substituted phenyl, R$^{4a}$ and R$^{16}$ are defined herein and n is 0-3) may be made by the method generally described in Scheme 1. As shown, a substituted bromo-fluoro-pyridine 1 can be treated with hyrazine under suitable conditions for a time period sufficient to form the bromo-hydazino-pyridine adduct 2. Intermediate 2 can be reacted with bromocyanide, in the presence of a suitable solvent, to form the triazolo ring of the resulting triazolo-pyridine adduct 3. The bromide of the amino triazolo-pyridine intermediate 3 can be reacted with a desired boronic acid reagent, such as boronate 4, in a Suzuki-like fashion in the presence of a suitable palladium catalyst and reaction media, to provide desired compounds 5. R$^4$ is also referred to herein in scheme 2 below and throughout the specification as the "B" ring. The Suzuki method is a reaction using a borane reagent, such as a dioxaborolane intermediate 4 (also described in scheme 3 below as a borane B-A intermediate 8), and a suitable leaving group containing reagent, such as the X-triazolo-pyridine 3 (X is a leaving group "LG", which may be an I or Br). As appreciated to one of ordinary skill in the art, Suzuki reactions also utilize a palladium catalyst. Suitable palladium catalysts include Pd(PPh3)4, Pd(OAc)2 or Pd(dppf)Cl2. Where LG is a halide, the halide may be an iodide, a bromide or even a chloride (chloro-pyridyl or chloro-picolinyl B rings undergo Suzuki reactions in the presence of Pd(OAc)2). Other LGs are also suitable. For example, Suzuki couplings are known to occur with a sulfonate, such as trifluoromethanesulfonate, as the leaving group.

The Suzuki reaction conditions may vary. For example, Suzuki reactions are generally run in the presence of a suitable base such as a carbonate base, bicarbonate or an acetate base, in a suitable solvent such as toluene, acetonitrile, DMF or an aqueous-organic solvent combination or a biphasic system of solvents. Further, the reaction may require heat depending upon the particular triazolo-pyridine 3 and/or boronic acid 4, as appreciated by those skilled in the art. In addition, where R$^4$ is an aromatic moiety, such as phenyl, the reaction may be complete in a short period of time with heat.

Further, the boronic acid 4 may be any suitable desired boronic acid having the general formula (RO)$_2$B—R$^4$ (where "B" is a direct bond) or (RO)$_2$B—"B"—R$^4$, (where "B" is a spacer such as an —(CR$^5$R$^6$)$_{0-2}$—, —C(═O)—, —N(R$^6$)—, —O— or —S(═O)$_{0-2}$—) as defined in Formula I. The boronic acid may also be a cyclic boronate (not shown). In this fashion, desired R$^1$ groups, such as amino R$^1$ groups, and R$^4$ groups such as aryl or heteroaryl R$^4$ groups, can be installed into the imidazo-pyridine (not shown) or triazolo-pyridine core 3. The desired boronic acid compounds 4 may generally be made as illustrated in scheme 3 below.

See also Examples 5 and 6 for methods of installing the boronate on a desired phthalazine ring. Other known metal coupling chemistry, such Stille, Kumada, Negishi coupling methods, and the like, may be employed to imidazo-pyridine (not shown) or triazolo-pyridine core 3 to desired cyclic R4-substituted moieties.

Scheme 2

1.

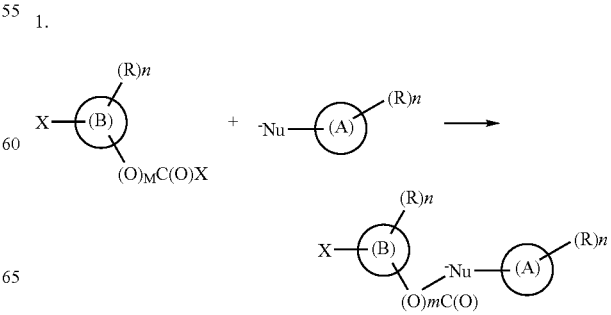

-continued

2.
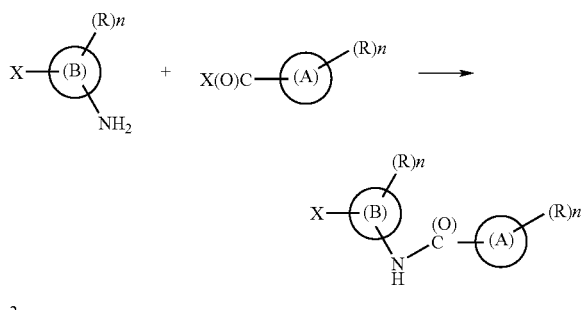

3.
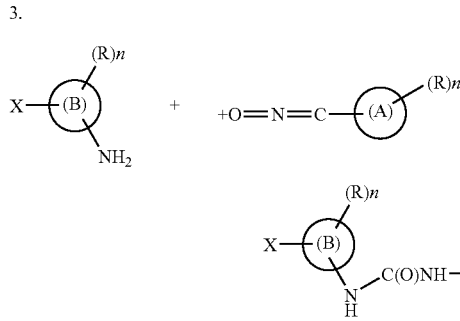

4.
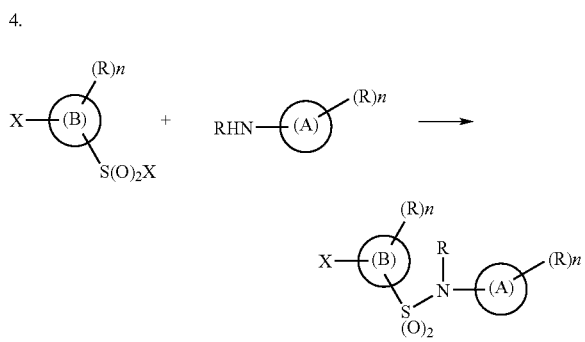

5.
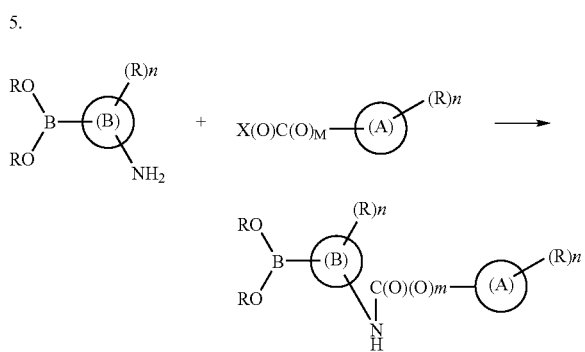

6.
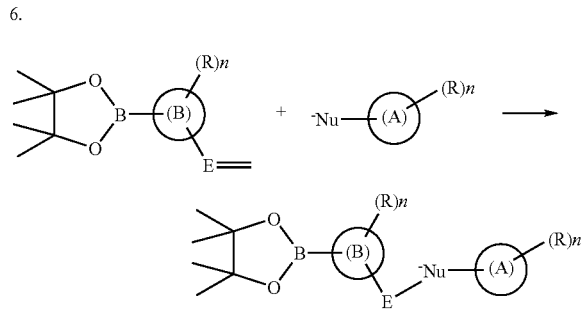

-continued

7.

8.

9.

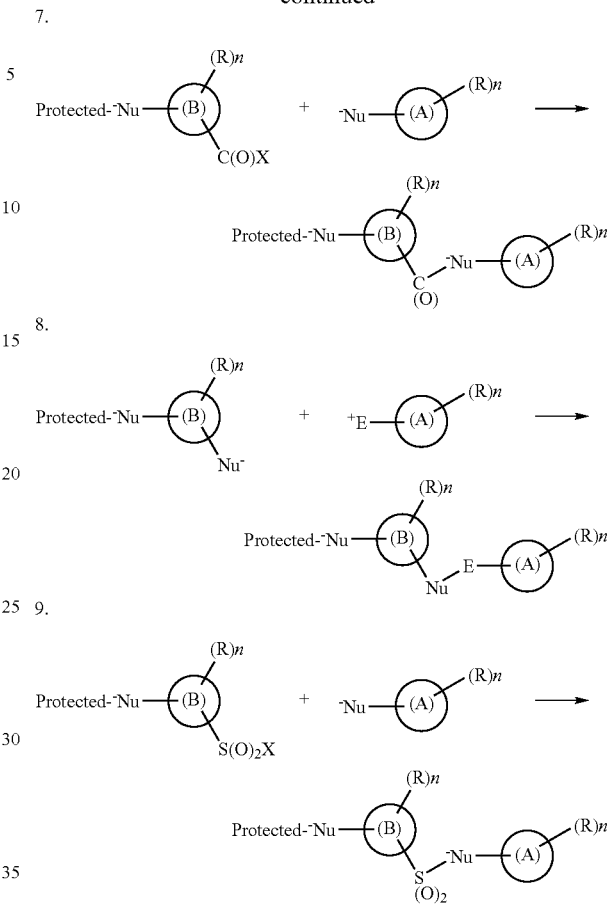

$R^4$ ring systems, generally designated and referred to in Scheme 2, and throughout the specification, as the "B ring" may be substituted with various substitutions as specified herein. For example, the substitution may be a linker, such as amino, carboxyl, sulfonyl, amido, and urea linker as defined herein in Formulas I and II, connecting various substitutions, including $R^{10}$ groups and $R^{11}$ ring systems (generally designated and referred to in Scheme 2, and throughout the specification, as the "A" group or "A" ring) to the $R^4$ ring ("B ring"). This linker may be attached by various coupling methods as described in Scheme 2. Each of the nine sub-schemes, numbered 1-9 above and described below, utilize the following meanings for $(R)_n$, X, Nu⁻, E⁺ and m: $(R)_n$ refers to n number of $R^{10}$, $R^{11}$ and $R^{16}$ substitutions wherein n is an integer from 0-9; X refers generally to a "leaving group" such as a halide (bromine, chlorine, iodine or fluorine), alkylsulfonate and other known groups (also see definitions herein); Nu⁻ refers generally to a nucleophilic species such as a primary or secondary amine, an oxygen, a sulfur or a anionic carbon species—examples of nucleophiles include, without limitation, amines, hydroxides, alkoxides and the like; E+ refers generally to an electrophilic species, such as the carbon atom of a carbonyl, which is susceptible to nucleophilic attack or readily eliminates—examples of suitable electrophilic carbonyl species include, without limitation, acid halides, mixed anhydrides, aldehydes, carbamoyl-chlorides, sulfonyl chlorides, acids activated with activating reagents such as TBTU, HBTU, HATU, HOBT, BOP, PyBOP and carbodiimides (DCC, EDC, CDI and the like), and other electrophilic species including halides, isocyanates, daizonium ions and the like; and m is either 0 or 1.

The coupling of ring B to A, as shown as products in sub-schemes 1-9, can be brought about using various conventional methods to link ring B and A together. For example, an amide or a sulfonamide linkage, as shown in sub-schemes 2 and 4, and 7 and 9 where the Nu– is an amine, respectively, can be made utilizing an amine on either the B or A groups and an acid chloride or sulfonyl chloride on the other of either the B or A groups. The reaction proceeds generally in the presence of a suitable solvent and/or base. Suitable solvents include, without limitation, generally non-nucleophilic, anhydrous solvents such as toluene, $CH_2Cl_2$, THF, DMF, DMSO, N,N-dimethylacetamide and the like, including solvent combinations thereof. The solvent may range in polarity, as appreciated by those skilled in the art. Suitable bases include, for example, tertiary amine bases such as DIEA, TEA, carbonate bases such as $Na_2CO_3$, $K_2CO_3$, $Cs_2CO_3$, hydrides such as NaH, KH, borohydrides, cyanoborohydrides and the like, alkoxides such as $NaOCH_3$, and the like. The base itself may also serve as a solvent. The reaction may optionally be run neat, i.e., without any base and/or solvent. These coupling reactions are generally fast and conversion occurs typically in ambient conditions. However, depending upon the particular substrate, such reactions may require heat, as appreciated by those skilled in the art.

Similarly, carbamates as illustrated in sub-schemes 5 and 1 where Nu– is an amine, anhydrides as illustrated in sub-scheme 1 where Nu– is an oxygen, reverse amides as generally illustrated in sub-scheme 8 where Nu– is an amine and E+ is an acid chloride, ureas as illustrated in sub-scheme 3, thioamides and thioureas where the respective carbonyl oxygen is a sulfur, thiocarbamates where the respective carbonyl oxygen and/or carbamate oxygen is a sulfur, and the like. While the above methods are so described, they are not exhaustive, and other methods for linking groups A and B together may be utilized as appreciated by those skilled in the art.

Although sub-schemes 1-9 are illustrated as having the nucleophilic and electrophilic coupling groups, such as the amino group and acid chloride groups illustrated in sub-scheme 2, directly attached to the substrate, either the A group or B ring, in question, the invention is not so limited. It is contemplated herein that these nucleophilic and/or electrophilic coupling groups may be tethered from their respective ring. For example, the amine group on the B ring, and/or the acid halide group on the A group or ring, as illustrated in sub-scheme 2, may be removed from direct attachment to the ring by a one or more atom spacer, such as by a methylene, ethylene spacer or the like. As appreciated by those skilled in the art, such spacer may or may not affect the coupling reactions described above, and accordingly, such reaction conditions may need to be modified to effect the desired transformation.

The coupling methods described in sub-schemes 1-9 of scheme 2 are also applicable for coupling desired A groups or rings to desired triazolo-pyridine-B ring intermediates, such as to substituted $R^4$ carboxylic acids (Example 2) to synthesize desired compounds of Formulas I and II. For example, a desirably substituted triazolo-pyridine-benzoic acid may be reacted with a desirably substituted primary or secondary amine, such as an $NHR^{10}R^{10}$ or $NHR^{10}R^{11}$ group in the presence of a suitable solvent and a known coupling reagent, such as TBTU, HATU, CDI or others, to prepare the desired A-BCD amide bond, and the final compound of Formulas I or II.

Note that the B-A moiety is connected through a linker "L". "L" may be any linker generally defined by the $R^4$ and $R^{4a}$ substitutions in Formulas I and II, and particularly, it includes, without limitation, an amide, a urea, a thiourea, a thioamide, a carbamate, an anhydride, a sulfonamide and the like, allowing for spacer atoms either between ring B and L and/or between ring or group A and L, as described in Scheme 2 above.

Further, the amine may be protected (not shown), such as with BOC—ON, while further substituents are coupled to the B ring, prior to or after coupling the B ring to an A ring or A group to form the desired $R^3$ group.

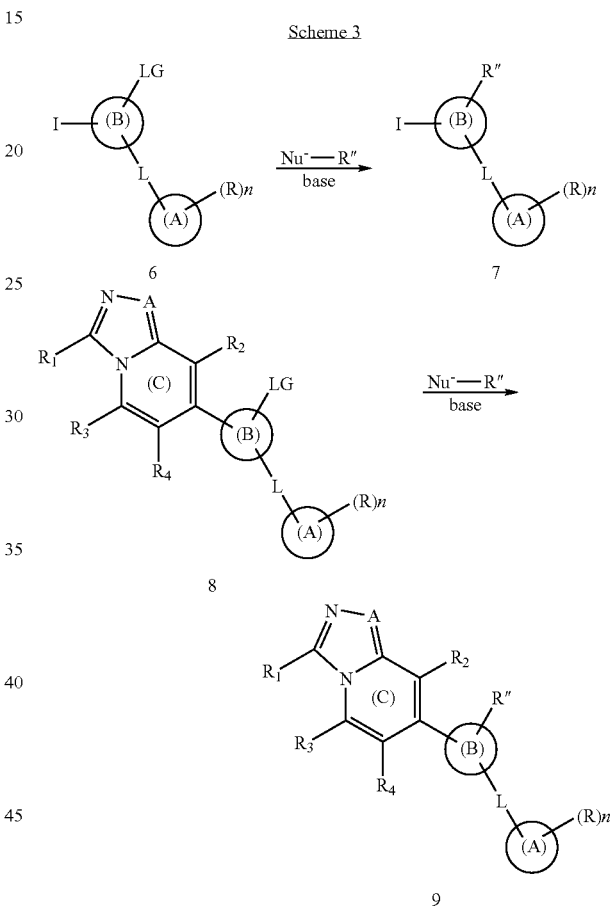

Scheme 3

Various $R^{10}$, $R^{11}$ and $R^{16}$ substitutions (designated generally as R" groups in compounds 7 and 9) can be installed on $R^4$ and $R^{4a}$ of Formulas I and II, with or without the triazolo-pyridine ring system attached, as described in Scheme 3. For instance, compounds 7 and 9 may be made by the method described in Scheme 3. As shown, iodinated aryl B ring compounds 6 and compounds 8 may contain suitable leaving groups, such as a fluoride, at a desired position for substitution. These intermediates (compounds 6 and 8) may be reacted with desirable nucleophilic R" groups ($R^{10}$, $R^{11}$ and $R^{16}$ substitutions), such as alkoxides, amines and the like, in the presence of a suitable base, such as a hydride or borohydride, to covalently bind the R" group to the B ring. Alternatively, the B ring may have a nucleophile, such as a hydroxide or an amine, which may be further functionalized as desired via standard chemical methodology, as appreciated by those skilled in the art.

To enhance the understanding and appreciation of the present invention, the following specific examples (starting reagents, intermediates and compounds of Formulas I and II) and methods of making compounds of the invention are set forth. It should be appreciated that the above general methods and specific examples below are merely for illustrative purposes only and are not to be construed as limiting the scope of this invention in any manner. The following analytical methods were used to purify and/or characterize the compounds, and intermediates, described in the examples below.

Analytical Methods:

Unless otherwise indicated, all HPLC analyses were run on a Agilent Model 1100 system with an Agilent Technologies Zorbax SB-C$_8$ (5μ) reverse phase column (4.6×150 mm; Part no. 883975-906) run at 30° C. with a flow rate of about 1.50 mL/min. The mobile phase used solvent A (H$_2$O/0.1% TFA) and solvent B (ACN/0.1% TFA) with a 11 min gradient from 5% to 100% ACN. The gradient was followed by a 2 min. return to 5% ACN and about a 2.5 min. re-equilibration (flush).

LC-MS Method:

Samples were run on an Agilent model-1100 LC-MSD system with an Agilent Technologies XDB-C$_8$ (3.5μ) reverse phase column (4.6×75 mm) at 30° C. The flow rate was constant and ranged from about 0.75 mL/min to about 1.0 mL/min.

The mobile phase used a mixture of solvent A (H$_2$O/0.1% HOAc) and solvent B (ACN/0.1% HOAc) with a 9 min time period for a gradient from 10% to 90% solvent B. The gradient was followed by a 0.5 min period to return to 10% solvent B and a 2.5 min 10% solvent B re-equilibration (flush) of the column.

Preparative HPLC Method:

Where indicated, compounds of interest were purified via reverse phase HPLC using a Gilson workstation utilizing one of the following two columns and methods: (A) Using a 50×100 mm column (Waters, Exterra, C18, 5 microns) at 50 mL/min. The mobile phase used was a mixture of solvent A (H$_2$O/10 mM ammonium carbonate at pH about 10, adjusted with conc. NH$_4$OH) and solvent B (85:15 ACN/water, 10 mM ammonium carbonate at pH of about 10 adjusted with conc. NH$_4$OH). Each purification run utilized a 10 minute gradient from 40% to 100% solvent B followed by a 5 minute flow of 100% solvent B. The gradient was followed by a 2 min return to 40% solvent B. (B) Using a 20×50 mm column at 20 mL/min. The mobile phase used was a mixture of solvent A (H$_2$O/0.1% TFA) and solvent B (ACN/0.1% TFA) with a 10 min gradient from 5% to 100% solvent B. The gradient is followed by a 2 min return to 5% ACN.

Proton NMR Spectra:

Unless otherwise indicated, all $^1$H NMR spectra were run on a Varian series Mercury 300 MHz instrument or a Bruker series 400 MHz instrument. Where so characterized, all observed protons are reported as parts-per-million (ppm) downfield from tetramethylsilane (TMS) or other internal reference in the appropriate solvent indicated.

Mass Spectra (MS)

Unless otherwise indicated, all mass spectral data for starting materials, intermediates and/or exemplary compounds are reported as mass/charge (m/z), having an (M+H$^+$) molecular ion. The molecular ion reported was obtained by electrospray detection method. Compounds having an isotopic atom, such as bromine and the like, are reported according to the detected isotopic pattern, as appreciated by those skilled in the art.

Example 1

Method A

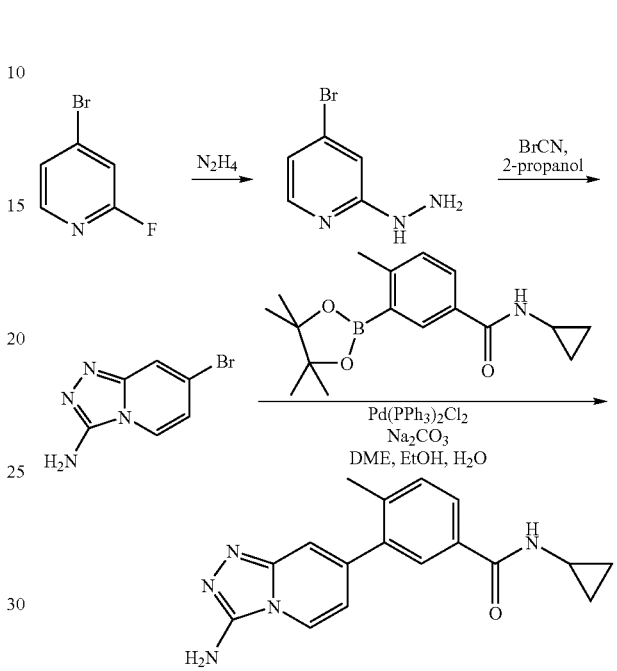

Step 1: Synthesis of
1-(4-Bromopyridin-2-yl)hydrazine

A mixture of 4-bromo-2-fluoropyridine (8.67 g, 49.3 mmol) and anhydrous hydrazine (16.00 ml, 501 mmol) was heated at 70° C. for 2.5 h. The reaction was cooled to RT, basified with 5N NaOH and diluted with 60 mL of water. The precipitate was filtered, washed with water and dried in vacuo at 50° C. to give 6.80 g of the title compound as a white amorphous solid.

Step 2: Synthesis of
7-Bromo-[1,2,4]triazolo[4,3-a]pyridin-3-amine

To a suspension of 1-(4-bromopyridin-2-yl)hydrazine (0.710 g, 3.78 mmol) in 10 mL of 2-propanol was added cyanogen bromide (0.400 g, 3.78 mmol) at 25° C. The reaction was heated at 70° C. for 2 h and the reaction was monitored by LCMS. Additional cyanogen bromide (0.060 g) was added and the reaction was continued for another 2 h. The reaction was filtered while hot and the solid was washed with 2-propanol and pentane, and dried in vacuo to give the title compounds as a light orange amorphous solid. MS m/z: 214.9 [M+1].

Step 3: Synthesis of 3-(3-Amino-[1,2,4]triazolo[4,3-a]pyridin-7-yl)-N-cyclopropyl-4-methylbenzamide A mixture of 7-bromo-[1,2,4]triazolo[4,3-a]pyridin-3-amine (0.202 g, 0.95 mmol), N-cyclopropyl-4-methyl-3-(4,4,5,5-tetramethyl-1,3,2-dioxaborolan-2-yl)benzamide (0.358 g, 1.2 mmol), sodium carbonate (0.439 g, 4.1 mmol)

and trans-dichlorobis(triphenyl-phosphine)palladium (II) (0.057 g, 0.081 mmol) in 7 μL of DME/3 mL of H₂O/2 mL of EtOH was heated at 80° C. After 2.5 h, the reaction mixture was cooled to 25° C., evaporated onto silica gel and purified by flash column chromatography eluting with 2M NH₃ in MeOH:CH₂Cl₂ (0:1→3:97) to give the title compound as a tan amorphous solid. MS m/z: 308.1 [M+1].

Example 2

Method B

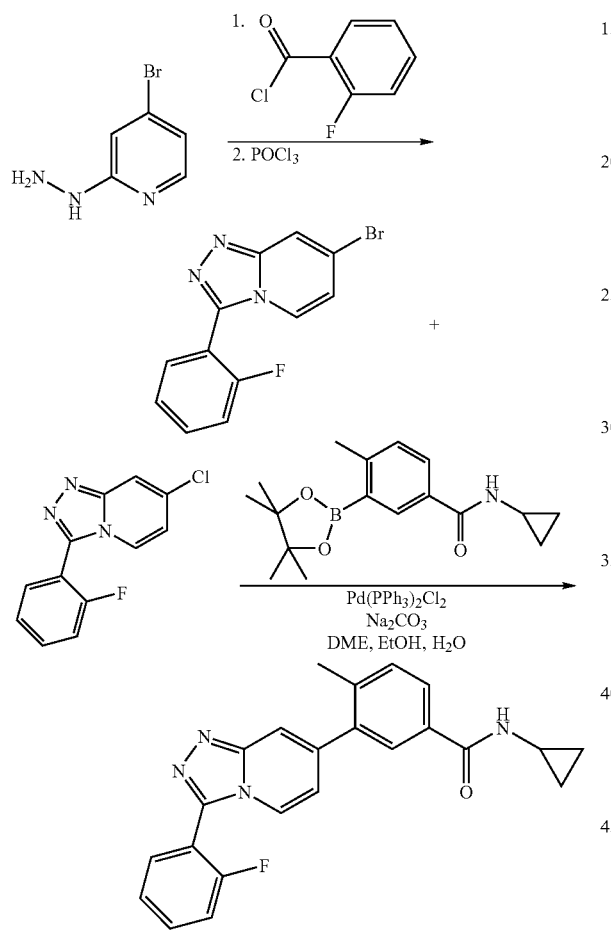

Step 1: Synthesis of 7-Bromo-3-(2-fluorophenyl)-[1,2,4]triazolo[4,3-a]pyridine and 7-chloro-3-(2-fluorophenyl)-[1,2,4]triazolo[4,3-a]pyridine To a solution of 1-(4-bromopyridin-2-yl)hydrazine (0.700 g, 3.72 mmol) in 30 mL of CH₂Cl₂ was added a solution of o-fluorobenzoyl chloride (0.550 ml, 4.61 mmol) in 5 mL of CH₂Cl₂ at RT. After 2.5 h, the mixture was filtered and the solid was washed with CH₂Cl₂, and dried in vacuo to give the acyl hydrazine intermediate as a white powder. Phosphorus oxychloride (6.00 ml, 65.5 mmol) was added to the solid and the mixture was heated at 100° C. for 5 h. The mixture was cooled to room temperature and the excess POCl₃ was removed in vacuo. The residue was azeotroped with toluene (2×) and the residue was dried in vacuo to give an off-white amorphous solid as a mixture 7-bromo-3-(2-fluorophenyl)-[1,2,4]triazolo[4,3-a]pyridine (MS m/z: 292.0 [M+1]) and 7-chloro-3-(2-fluorophenyl)-[1,2,4]triazolo[4,3-a]pyridine (MS m/z: 248.1 [M+1]).

Step 2: Synthesis of N-Cyclopropyl-3-(3-(2-fluorophenyl)-[112.4]triazolo[4,3-a]pyridin-7-yl)-4-methylbenzamide A mixture of 7-bromo-3-(2-fluorophenyl)-[1,2,4]triazolo[4,3-a]pyridine (0.215 g, 0.74 mmol), N-cyclopropyl-4-methyl-3-(4,4,5,5-tetramethyl-1,3,2-dioxaborolan-2-yl)benzamide (0.273 g, 0.91 mmol), sodium carbonate (0.516 g, 4.9 mmol) and trans-dichlorobis(triphenylphosphine)palladium (II) (0.046 g, 0.066 mmol) in 4.2 mL of DME/1.8 mL of H₂O/1.2 mL of EtOH was heated at 150° C. for 15 min in the microwave. The reaction mixture was diluted with MeOH, evaporated onto silica gel and purified by flash chromatography eluting with 2M NH₃ in MeOH:CH₂Cl₂ (0:1→3:197) to give a brown tar that was impure by TLC. The material was dissolved in MeOH and purified further by reverse-phase HPLC (Gilson; Phenomenex Synergi, 4u MAX-RP, 150×21 20 mm) eluting with 0.1% TFA-H₂O:0.1% TFA CH₃CN (9:1→1:9). The fractions containing the desired compound were combined and partitioned between EtOAc/saturated NaHCO₃. The aqueous layer was extracted with EtOAc (3×) and the combined organic layers were dried over MgSO₄. Concentration in vacuo gave the title compound as a white amorphous solid. MS m/z: 387.2 [M+1].

Example 3

Method C

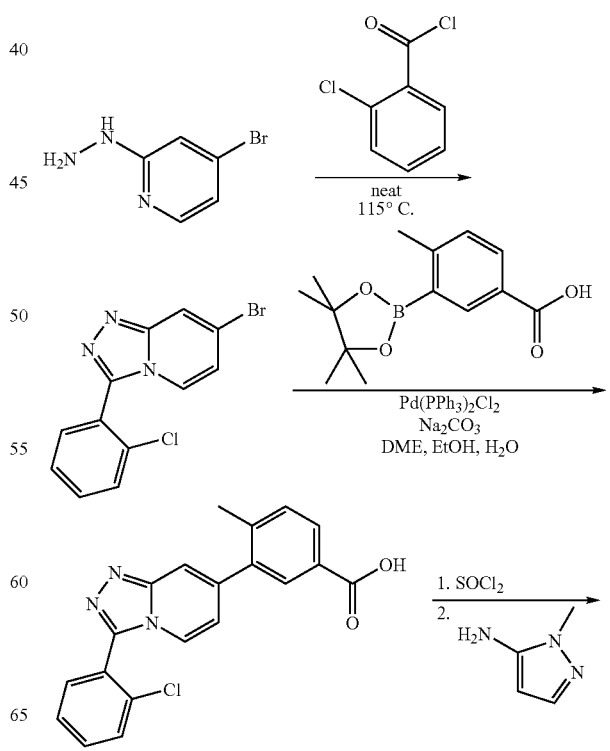

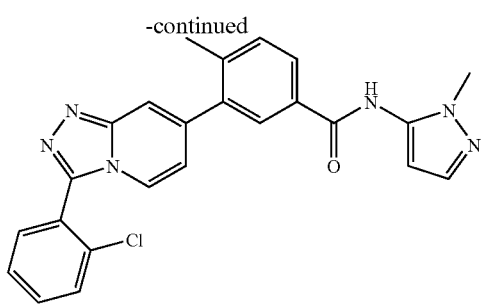

Step 1: 7-Bromo-3-(2-chlorophenyl)-[1,2,4]triazolo[4,3-a]pyridine

A mixture of 1-(4-bromopyridin-2-yl)hydrazine (1.00 g, 5.3 mmol) and 2-chlorobenzoyl chloride (8.00 ml, 63 mmol, Aldrich) was heated to 115° C. for 3 h. The mixture was diluted with MeOH and concentrated over $SiO_2$. The residue was purified using column chromatography (MeOH/$CH_2Cl_2$=0-10%) yielding the title compound as a tan solid. MS (ESI, pos. ion) m/z: 264.0 (M+1).

Step 2: Synthesis of 3-(3-(2-Chlorophenyl)-[1,2,4]triazolo[4,3-a]pyridin-7-yl)-4-methylbenzoic acid A mixture of 7-chloro-3-(2-chlorophenyl)-[1,2,4]triazolo[4,3-a]pyridine (1.77 g, 6.7 mmol), 3-borono-4-methylbenzoic acid (1.57 g, 8.7 mmol), $Pd(PPh_3)_2Cl_2$ (0.329 g, 0.46 mmol, Strem), and sodium carbonate (2.13 g, 20 mmol, JT Baker) in DME:EtOH:$H_2O$=7:2:3 (8 ml) was heated to 80° C. for 8 h. The mixture was cooled to room temperature, diluted with MeOH and filtered through Celite. The filtrate was concentrated to yield the title compound as a brown solid. MS (ESI, pos. ion) m/z: 364.0 (M+1).

Step 3: Synthesis of 3-(3-(2-Chlorophenyl)-[1,2,4]triazolo[4,3-a]pyridin-7-yl)-4-methyl-N-(1-methyl-1H-pyrazol-5-yl)benzamide A mixture of 3-(3-(2-chlorophenyl)-[1,2,4]triazolo[4,3-a]pyridin-7-yl)-4-methylbenzoic acid (2.44 g, 6.7 mmol) and thionyl chloride (30 ml, 411 mmol, Aldrich) was heated to 95° C. for 2 h. The volatiles were removed in vacuo. The solids were re-dissolved in $CH_2Cl_2$ (30 ml). A 10 ml aliquot of this solution (860 mg, 2.2 mmol) was treated with 1-methyl-1H-pyrazol-5-amine (656 mg, 6.7 mmol, Maybridge), followed by triethylamine (939 μl, 6.7 mmol, Aldrich). The mixture was diluted with 10% $Na_2CO_3$ and extracted with $CH_2Cl_2$ (3×). The combined organics were dried over $Na_2SO_4$, filtered and concentrated over silica gel. The residue was purified using column chromatography (Acetone/Hexanes=0-50%). The mixture was dissolved in MeOH and loaded onto an Agilent AccuBOND II SCX solid phase extraction column. After washing with MeOH, the title compound was eluted with 2M $NH_3$ in MeOH. The residue was recrystallized from MeOH yielding the title compound as a white solid. HRMS (TOF) Calcd for $C_{24}H_{20}ClN_6O^+$: 443.1382, found: 443.1389.

Example 4

Method D

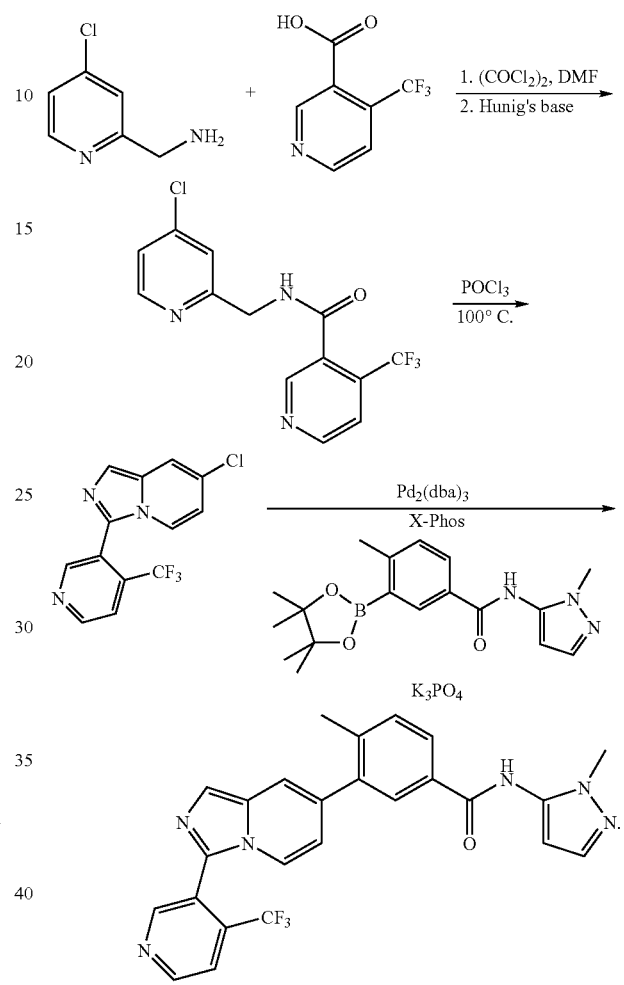

Step 1: Synthesis of N-((4-chloropyridin-2-yl)methyl)-4-(trifluoromethyl)nicotinamide To a 100 mL round-bottomed flask was added 4-(trifluoromethyl)nicotinic acid (938 mg, 4909 μmol) in DCM (5 mL), 2 drops of DMF was added oxalyl chloride, 2.0M solution in DCM (7364 μl, 14728 μmol) and the reaction mixture was allowed to stir for 30 mins. Reaction Mixture was evaporated in vacuo to remove volatiles. The acid chloride so formed was dried under vacuum at RT, re-dissolved in DCM (5 mL) and Hunig's Base (857 μl, 4909 μmol) was added. To this, (4-chloropyridin-2-yl)methanamine (700 mg, 4909 μmol, synthesized as described in WO 2005/090304) dissolved in DCM (5 mL) was added and the brown solution allowed to stir for 2 hours. The reaction mixture was washed with satd. sodium bicarbonate (200 mL) and brine (100 mL) in separating funnel. The organic layer was dried over sodium sulfate and evaporated to yield crude. The crude product was chromatographed through a Redi-Sep® pre-packed silica gel column (12 g), eluting with a gradient of 50% to 80% EtOAc in hexane, to provide N-((4-chloropyridin-2-yl)methyl)-4-(trifluoromethyl)nicotinamide (735 mg, 47% yield).

Step 2: Synthesis of 7-chloro-3-(4-(trifluoromethyl)pyridin-3-yl)H-imidazo[1,5-a]pyridine To a 50 mL round-bottomed flask was added N-((4-chloropyridin-2-yl)methyl)-4-(trifluoromethyl)nicotinamide (300 mg, 950 μmol) and cooled with a ice bath. Phosphorous oxychloride (2746 μl, 29460 μmol) was added dropwise and the reaction mixture was allowed to stir for 15 mins. The reaction mixture was then heated under a reflux condenser at 100 deg C. After 48 hours, ice was slowly added to the reaction mixture followed by ammonium hydroxide to basify. The reaction mixture was separated between DCM and water. The organic layer was dried over sodium sulfate and evaporated to yield a crude material. The crude product-containing material was loaded on silica gel and chromatographed through a Redi-Sep® pre-packed silica gel column (12 g), eluting with a gradient of 40% to 60% EtOAc in hexane, to provide 7-chloro-3-(4-(trifluoromethyl)pyridin-3-yl)H-imidazo[1,5-a]pyridine.

Step 3: Synthesis of 4-methyl-N-(1-methyl-1H-pyrazol-5-yl)-3-(3-(4-(trifluoromethyl)pyridin-3-yl)H-imidazo[1,5-a]pyridin-7-yl)benzamide A glass microwave reaction vessel was charged with tris(dibenzylideneacetone)dipalladium (0) (3.1 mg, 3.4 μmol), potassium phosphate tribasic (41 μl, 504 μmol), 4-methyl-N-(1-methyl-1H-pyrazol-5-yl)-3-(4,4,5,5-tetramethyl-1,3,2-dioxaborolan-2-yl)benzamide (85 mg, 249 μmol), 7-chloro-3-(4-(trifluoromethyl)pyridin-3-yl)H-imidazo[1,5-a]pyridine (50 mg, 168 μmol), X-phos (4.7 mg, 0.04 eq) and dioxane (1.5 mL) and water (0.5 mL). The reaction mixture was stirred and heated in a Smith Synthesizer® microwave reactor (Personal Chemistry, Inc., Upssala, Sweden) at 140° C. for 20 mins. The reaction mixture was evaporated and residue dissolved in EtOAc (20 mL) and washed with water (2×20 mL) and dried over MgSO₄ and rotovaped to yield crude product, which was chromatographed through a Redi-Sep® pre-packed silica gel column (12 g), eluting with a gradient of 50% to 75% ethyl acetate in hexane, to provide 4-methyl-N-(1-methyl-1H-pyrazol-5-yl)-3-(3-(4-(trifluoromethyl)pyridin-3-yl)H-imidazo[1,5-a]pyridin-7-yl)benzamide. MS (ESI, pos. ion) m/z: (M+1) 477.1.

Example 5

Method E

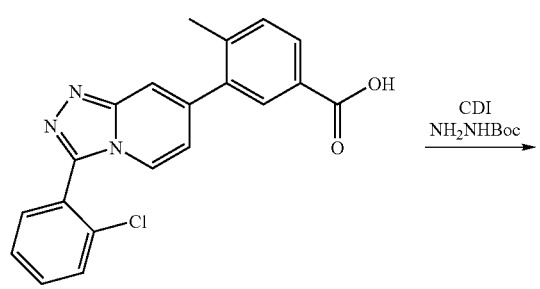

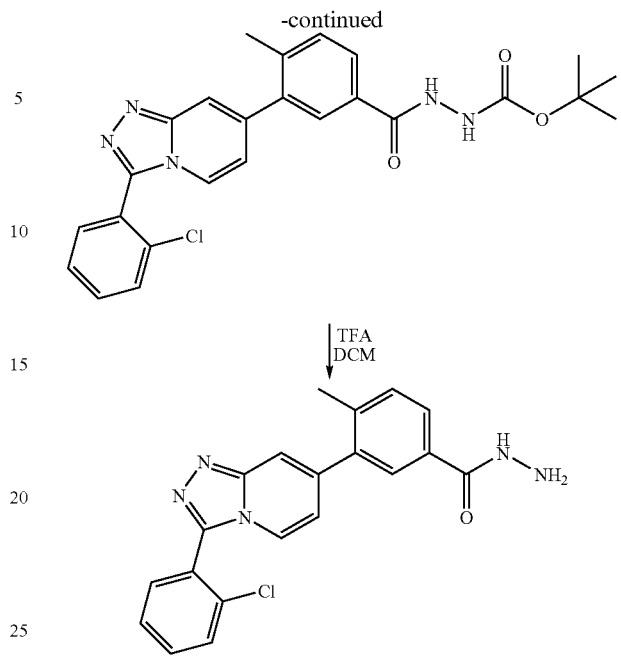

Synthesis of N'-Boc-3-(3-(2-chlorophenyl)-[1,2,4]triazolo[4,3-a]pyridin-7-yl)-4-methylbenzohydrazide Step 1: N'-boc-3-(3-(2-chlorophenyl)-[1,2,4]triazolo[4,3-a]pyridin-7-yl)-4-methylbenzohydrazide To a solution of 3-(3-(2-chlorophenyl)-[1,2,4]triazolo[4,3-a]pyridin-7-yl)-4-methylbenzoic acid (444 mg, 1.22 mmol) in 15 mL of THF at RT was added CDI (218 mg, 1.34 mmol). The resulting mixture was heated for 1 h at 50° C. The reaction mixture was then cooled to RT and tert-butyl carbazate (177 mg, 1.34 mmol) was added. The reaction mixture was again heated at 50° C. for 24 h. After the reaction mixture was concentrated to dryness, the residue was purified on the ISCO (40 g column, 50-100% EtOAc in Hexanes) to afford the title compound as an off-white amorphous solid. MS (ESI, pos. ion) m/z: 478.1 (M+1).

Step 2: 3-(3-(2-Chlorophenyl)-[1,2,4]triazolo[4,3-a]pyridin-7-yl)-4-methylbenzohydrazide A solution of N'-boc-3-(3-(2-chlorophenyl)-[1,2,4]triazolo[4,3-a]pyridin-7-yl)-4-methylbenzohydrazide (300 mg, 0.63 mmol) in 3.0 mL of DCM at RT was treated with 2.0 mL of TFA. After 1.5 h of stirring, the volatiles were evaporated. The residue was dissolved in DCM, washed with 1 N NaOH followed by brine. The DCM layer was dried and concentrated to afford the title compound as a white amorphous solid. MS (ESI, pos. ion) m/z: 378 (M+1).

Example 6

Method F

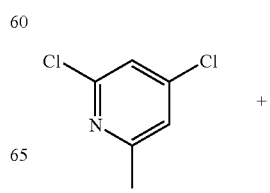

+

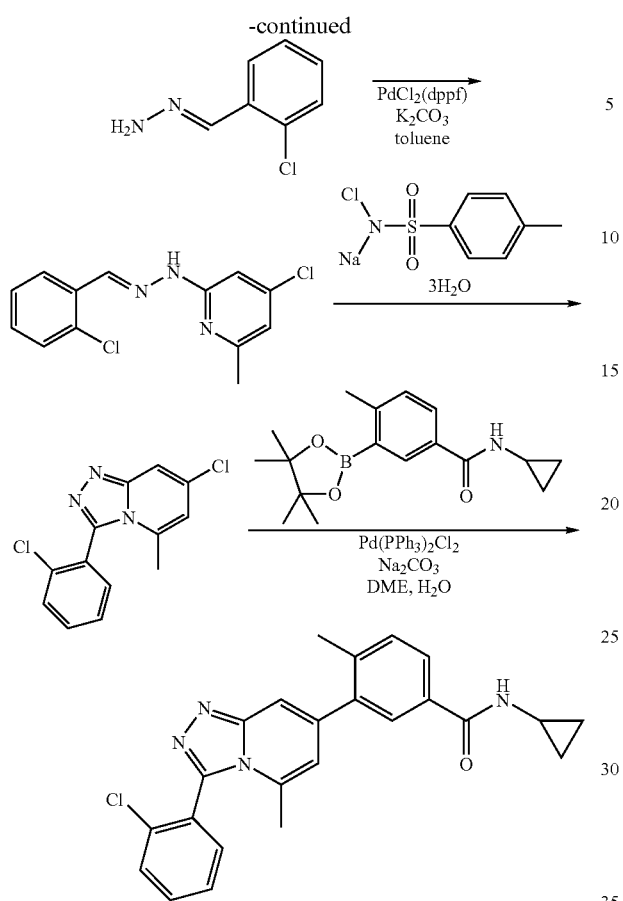

Synthesis of 3-(3-(2-chlorophenyl)-5-methyl-[1,2,4]triazolo[4,3-a]pyridin-7-yl)-N-cyclopropyl-4-methylbenzamide Step 1: Synthesis of (E)-1-(2-chlorobenzylidene)-2-(4-chloro-6-methylpyridin-2-yl)hydrazine (E)-1-(2-chlorobenzylidene)hydrazine (0.351 g, 2.27 mmol), dichloro[1,1'bis(diphenylphosphino)ferrocene]palladium (II) dichloromethane adduct (0.0185 g, 0.0227 mmol) and potassium carbonate (0.471 g, 3.41 mmol) was added to a 50-mL RBF. Toluene (2 mL) was added and 2,4-dichloro-6-methylpyridine (0.368 g, 2.27 mmol) in 3 mL of toluene was added. The red mixture was heated to 100° C. After 18 h, the reaction was allowed to cool to RT and water (20 mL) was added. The mixture was filtered and 190 mg of (E)-1-(2-chlorobenzylidene)-2-(4-chloro-6-methylpyridin-2-yl) hydrazine was collected as a tan solid. The filtrate was absorbed on silica gel and purified by silica gel chromatography (8/2 hexanes/DCM to 7/2/1 hexans/DCM/EtOAc) to afford an additional 200 mg of (E)-1-(2-chlorobenzylidene)-2-(4-chloro-6-methylpyridin-2-yl) hydrazine as a tan solid. MS (ESI, pos. ion) m/z: 280.0 (M+1).

Step 2: Synthesis of 7-chloro-3-(2-chlorophenyl)-5-methyl-[1,2,4]triazolo[4,3-a]pyridine A mixture of (E)-1-(2-chlorobenzylidene)-2-(4-chloro-6-methylpyridin-2-yl)hydrazine (0.247 g, 0.882 mmol) and chloramine trihydrate (0.273 g, 0.970 mmol) in 7 mL of EtOH was heated at 80° C. for 2 h. After cooling to RT, water was added and the mixture was extracted with EtOAc (3×). The combined organic layers were dried over anhydrous sodium sulfate, filtered and concentrated to give 1.05 g of crude material. The crude material was purified by silica gel chromatography (50-75% EtOAc in hexanes) to afford 7-chloro-3-(2-chlorophenyl)-5-methyl-[1,2,4]triazolo[4,3-a]pyridine as an off white solid. MS (ESI, pos. ion) m/z: 278.0 (M+1).

Step 3: Synthesis of 3-(3-(2-chlorophenyl)-5-methyl-[1,2,4]triazolo[4,3-a]pyridin-7-yl)-N-cyclopropyl-4-methylbenzamide In a microwave tube was placed 7-chloro-3-(2-chlorophenyl)-5-methyl-[1,2,4]triazolo[4,3-a]pyridine (0.061 g, 0.22 mmol), N-cyclopropyl-4-methyl-3-(4,4,5,5-tetramethyl-1,3,2-dioxaborolan-2-yl)benzamide (0.086 g, 0.29 mmol), trans-dichlorobis(triphenylphosphine)palladium (II) (0.013 g, 0.018 mmol) and sodium carbonate monohydrate (0.16 g, 1.3 mmol) in 1 mL of DME and 0.4 mL of water. The mixture was heated in the microwave at 140° C. for 15 min. Water was then added and the mixture was extracted with EtOAc (3×). The combined organic layers were dried over anhydrous sodium sulfate, filtered and concentrated to give 220 mg of a brown oil. The crude material was purified by silica gel chromatography (0-5% MeOH in DCM) to afford the title compound as an off-white solid. MS (ESI, pos. ion) m/z: 417.2 (M+1).

Example 7

Method G

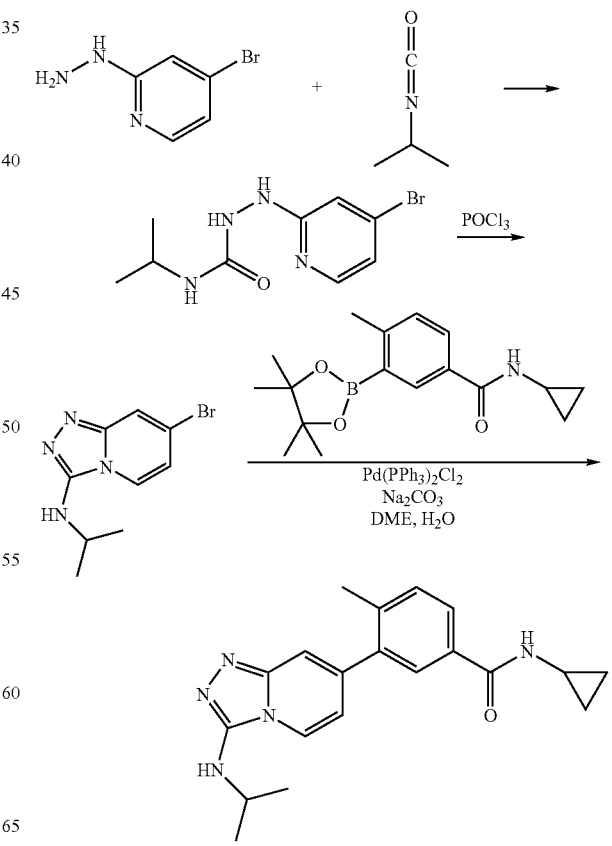

Synthesis of N-cyclopropyl-3-(3-(isopropylamino)-[1,2,4]triazolo[4,3-a]pyridin-7-yl)-4-methylbenzamide

Step 1: Synthesis of 1-(4-bromopyridin-2-yl)-4-isopropylsemicarbazide

To a solution of 1-(4-bromopyridin-2-yl) hydrazine (0.376 g, 2.00 mmol) in 10 mL of DCM at 0° C. was added isopropyl isocyanate (0.216 mL, 2.20 mmol). The heterogeneous mixture was allowed to warm up to RT and stir. A white precipitate appeared and after 1 h the solid was collected by filtration and washed with DCM to afford 1-(4-bromopyridin-2-yl)-4-isopropylsemicarbazide as a white solid. MS (ESI, pos. ion) m/z: 273.2 (M+1).

Step 2: Synthesis of 7-bromo-N-isopropyl-[1,2,4]triazolo[4,3-a]pyridin-3-amine A heterogeneous mixture of 1-(4-bromopyridin-2-yl)-4-isopropylsemicarbazide (0.315 g, 1.15 mmol) in phosphorous oxychloride (1.06 mL, 11.5 mmol) was heated at 100° C. for 2 h. The homogenous solution was allowed to cool to RT. Toluene (10 mL) was added and removed in vacuo (3×). DCM (20 mL) and saturated sodium bicarbonate (aq.) was added to the solid and stirred. The off-white solid was collected by filtration and washed with DCM to give 7-bromo-N-isopropyl-[1,2,4]triazolo[4,3-a]pyridin-3-amine. MS (ESI, pos. ion) m/z: 255.2 (M+1).

Step 3: Synthesis of N-cyclopropyl-3-(3-(isopropylamino)-[1,2,4]triazolo[4,3-a]pyridin-7-yl)-4-methylbenzamide In a microwave tube was placed 7-bromo-N-isopropyl-[1,2,4]triazolo[4,3-a]pyridin-3-amine (0.105 g, 0.41 mmol), N-cyclopropyl-4-methyl-3-(4,4,5,5-tetramethyl-1,3,2-dioxaborolan-2-yl)benzamide (0.16 g, 0.54 mmol), trans-dichlorobis(triphenyl-phosphine)palladium (II) (0.024 g, 0.034 mmol) and sodium carbonate monohydrate (0.29 g, 2.3 mmol) in 2.8 mL of DME and 1.1 mL of water. The mixture was heated in the microwave at 150° C. for 15 min. Water was then added and the mixture was extracted with DCM (3×). The combined organic layers were dried over anhydrous sodium sulfate, filtered and concentrated to give 203 mg of a black solid. The crude material was purified by silica gel chromatography (0-5% MeOH in DCM) to afford the title compound as a pale yellow solid. MS (ESI, pos. ion) m/z: 350.4 (M+1).

The following Examples in Table 1 will further assist in understanding and appreciating the invention. However, in no way is the following list of compounds intended to limit the scope of the invention. The compounds of examples 5-33 were made in accordance with exemplary methods A-D, which correspond to Examples 14 above, respectively, and named according to the ACD naming convention, as associated with ISIS software. The mass spectral data is recorded M+H+, which is the positive ion as measured by an electrospray ionization method. The biological data (uM) have been conventionally rounded off to the next higher or lower decimal third place.

TABLE 1

| Ex. No | Name | MS (M + H+) | Method | p38 HTRF assay | THP-1 cell assay | LPS induced TNFa |
|---|---|---|---|---|---|---|
| 4 | 4-methyl-N-(1-methyl-1H-pyrazol-5-yl)-3-(3-(4-(trifluoromethyl)-3-pyridinyl)imidazo[1,5-a]pyridin-7-yl)benzamide | 477.1 | D | + | ++ | ++ |
| 8 | 3-(3-(3,5-difluorophenyl)imidazo[1,5-a]pyridin-7-yl)-4-methyl-N-(1-methyl-1H-pyrazol-5-yl)benzamide | 444.1 | D | + | +++ | +++++ |
| 9 | 3-(3-(2-chlorophenyl)imidazo[1,5-a]pyridin-7-yl)-4-methyl-N-(1-methyl-1H-pyrazol-5-yl)benzamide | 442.1 | D | + | + | ++ |
| 10 | 3-(3-(2-chlorophenyl)[1,2,4]triazolo-[4,3-a]pyridin-7-yl)-N-cyclopropyl-4-methylbenzamide | 403.1 | C | + | + | ++ |
| 11 | 3-(3-(2-chlorophenyl)[1,2,4]triazolo-[4,3-a]pyridin-7-yl)-4-methyl-N-(1-methylcyclopropyl)benzamide | 417.1 | C | + | ++ | ++ |
| 3 | 3-(3-(2-chlorophenyl)[1,2,4]triazolo-[4,3-a]pyridin-7-yl)-4-methyl-N-(1-methyl-1H-pyrazol-5-yl)benzamide | 443.1 | C | + | + | + |
| 12 | N-cyclopropyl-4-methyl-3-(3-(4-(methylsulfonyl)phenyl)[1,2,4]-triazolo[4,3-a]pyridin-7-yl)benzamide | 447.1 | C | ++ | +++++ | ++++ |

TABLE 1-continued

| Ex. No | Name | MS (M + H+) | Method | p38 HTRF assay | THP-1 cell assay | LPS induced TNFa |
|---|---|---|---|---|---|---|
| 13 | 4-methyl-N-(1-methylcyclopropyl)-3-(3-(4-(methylsulfonyl)phenyl)[1,2,4]-triazolo[4,3-a]pyridin-7-yl)benzamide | 461.2 | C | ++ | ++++ | ++++ |
| 14 | 4-methyl-N-(1-methyl-1H-pyrazol-5-yl)-3-(3-(4-(methylsulfonyl)phenyl)[1,2,4]-triazolo[4,3-a]pyridin-7-yl)benzamide | 487.2 | C | ++ | +++++ | +++++ |
| 15 | N-cyclopropyl-3-(3-(4-fluoro-2-methylphenyl)[1,2,4]triazolo-[4,3-a]pyridin-7-yl)-4-methylbenzamide | 401.2 | B | + | + | ++ |
| 16 | 3-(3-(4-fluoro-2-methylphenyl)[1,2,4]triazolo-[4,3-a]pyridin-7-yl)-4-methyl-N-(1-methylcyclopropyl)benzamide | 415.2 | B | ++ | +++ | +++ |
| 17 | 3-(3-(4-fluoro-2-methylphenyl)[1,2,4]triazolo-[4,3-a]pyridin-7-yl)-4-methyl-N-(1-methyl-1H-pyrazol-5-yl)benzamide | 441.2 | B | + | + | + |
| 18 | N-cyclopropyl-4-methyl-3-(3-(3-(methylsulfonyl)phenyl)[1,2,4]-triazolo[4,3-a]pyridin-7-yl)benzamide | 447 | B | ++ | ++++ | +++ |
| 19 | N-cyclopropyl-4-methyl-3-(3-phenyl[1,2,4]triazolo[4,3-a]pyridin-7-yl)benzamide | 369.1 | B | + | +++ | ++++ |
| 20 | 4-methyl-N-(1-methyl-1H-pyrazol-5-yl)-3-(3-(1-(trifluoromethyl)cyclopropyl)-[1,2,4]triazolo[4,3-a]pyridin-7-yl)benzamide | 441.2 | B | + | + | |
| 21 | N-cyclopropyl-4-methyl-3-(3-(1-(trifluoromethyl)cyclopropyl)-[1,2,4]triazolo[4,3-a]pyridin-7-yl)benzamide | 401.1 | B | + | + | |
| 22 | N-cyclopropyl-3-(3-(4-fluoro-2-methylphenyl)imidazo[1,5-a]pyridin-7-yl)-4-methylbenzamide | 400.1 | D | + | ++ | ++ |
| 23 | 3-(3-(4-fluoro-2-methylphenyl)imidazo[1,5-a]pyridin-7-yl)-4-methyl-N-(1-methyl-1H-pyrazol-5-yl)benzamide | 440.2 | D | + | + | ++ |
| 1 | 3-(3-amino[1,2,4]triazolo[4,3-a]pyridin-7-yl)-N-cyclopropyl-4-methylbenzamide | 308.1 | A | ++++ | +++++ | +++++ |
| 24 | 3-(3-amino[1,2,4]triazolo[4,3-a]pyridin-7-yl)-4-methylbenzamide | 268.1 | A | +++++ | +++++ | +++++ |
| 25 | N-cyclopropyl-3-(3-(2,2-dimethylpropyl)[1,2,4]triazolo-[4,3-a]pyridin-7-yl)-4-methylbenzamide | 363.2 | C | + | ++ | ++ |
| 26 | 3-(3-(2-chloro-4-(methylsulfonyl)phenyl)[1,2,4]-triazolo[4,3-a]pyridin-7-yl)-N-cyclopropyl-4-methylbenzamide | 481.1 | B | + | +++ | |
| 27 | N-cyclopropyl-4-methyl-3-(3-(1-methylethyl)[1,2,4]triazolo[4,3-a]pyridin-7-yl)benzamide | 335.2 | B | + | ++ | |
| 28 | 4-methyl-3-(3-(1-methylethyl)[1,2,4]triazolo[4,3-a]pyridin-7-yl)-N-(1-methyl-1H-pyrazol-5-yl)benzamide | 375.2 | B | + | +++ | +++ |

TABLE 1-continued

| Ex. No | Name | MS (M + H+) | Method | p38 HTRF assay | THP-1 cell assay | LPS induced TNFa |
|---|---|---|---|---|---|---|
| 29 | N-cyclopropyl-4-methyl-3-(3-(3-pyridinyl)[1,2,4]triazolo[4,3-a]pyridin-7-yl)benzamide | 370.2 | B | +++ | +++ | +++ |
| 2 | N-cyclopropyl-3-(3-(2-fluorophenyl)[1,2,4]triazolo[4,3-a]pyridin-7-yl)-4-methylbenzamide | 387.2 | B | + | ++ | ++ |
| 30 | 3-(3-(2-fluorophenyl)[1,2,4]triazolo[4,3-a]pyridin-7-yl)-4-methyl-N-(1-methyl-1H-pyrazol-5-yl)benzamide | 427.1 | B | + | ++ | ++ |
| 31 | N-cyclopropyl-4-methyl-3-(3-(2,2,2-trifluoroethyl)[1,2,4]triazolo-[4,3-a]pyridin-7-yl)benzamide | 375.1 | B | ++ | +++ | ++++ |
| 32 | N-cyclopropyl-4-methyl-3-(3-(2-methylphenyl)[1,2,4]triazolo[4,3-a]pyridin-7-yl)benzamide | 383.2 | C | + | ++ | +++ |
| 33 | 4-methyl-N-(1-methyl-1H-pyrazol-5-yl)-3-(3-(2-methyl-3-pyridinyl)[1,2,4]triazolo[4,3-a]pyridin-7-yl)benzamide | 424.4 | B | ++ | +++ | ++++ |
| 34 | N-cyclopropyl-4-methyl-3-(3-(2-methyl-3-pyridinyl)[1,2,4]triazolo[4,3-a]pyridin-7-yl)benzamide | 384.4 | B | ++ | ++ | +++ |
| 35 | 3-(3-(2-chlorophenyl)-6-methyl[1,2,4]triazolo[4,3-a]pyridin-7-yl)-N-cyclopropyl-4-methylbenzamide | 417.1 | B | + | + | ++ |
| 36 | 3-(3-(2-chlorophenyl)-6-methyl[1,2,4]triazolo[4,3-a]pyridin-7-yl)-4-methyl-N-(1-methyl-1H-pyrazol-5-yl)benzamide | 457.1 | B | + | + | ++ |
| 37 | N-cyclopropyl-4-methyl-3-(3-phenyl[1,2,4]triazolo[4,3-a]pyridin-7-yl)benzamide | 369.1 | B | + | +++ | ++++ |
| 38 | N-cyclopropyl-4-methyl-3-(3-(2-methyl-3-pyridinyl)[1,2,4]triazolo[4,3-a]pyridin-7-yl)benzamide | 384.4 | B | ++ | ++ | +++ |
| 39 | 3-(3-(2-chloro-3-fluorophenyl)[1,2,4]triazolo[4,3-a]pyridin-7-yl)-N-cyclopropyl-4-methylbenzamide | 421.1 | B | + | ++ | +++ |
| 40 | 3-(3-(2-chlorophenyl)[1,2,4]triazolo-[4,3-a]pyridin-7-yl)-N,4-dimethylbenzamide | 377.1 | B | ++ | ++ | +++ |
| 41 | 3-(3-(2-chloro-3-fluorophenyl)[1,2,4]triazolo[4,3-a]pyridin-7-yl)-4-methyl-N-(1-methyl-1H-pyrazol-5-yl)benzamide | 461.1 | B | + | + | ++ |
| 42 | 3-(3-(2-chloro-4-fluorophenyl)[1,2,4]triazolo[4,3-a]pyridin-7-yl)-N-cyclopropyl-4-methylbenzamide | 421.1 | B | + | ++ | +++ |
| 43 | 3-(3-(2-chlorophenyl)[1,2,4]triazolo-[4,3-a]pyridin-7-yl)-4-methyl-N-(1-methylethyl)benzamide | 405.1 | B | ++ | +++ | ++++ |
| 44 | 3-(3-(2-chlorophenyl)[1,2,4]triazolo-[4,3-a]pyridin-7-yl)-4-methylbenzamide | 363.1 | B | + | ++ | +++ |
| 45 | 3-(3-(2-chloro-4-fluorophenyl)[1,2,4]triazolo[4,3-a]pyridin-7-yl)-4-methyl-N-(1-methyl-1H-pyrazol-5-yl)benzamide | 461.1 | B | + | + | +++ |

TABLE 1-continued

| Ex. No | Name | MS (M + H+) | Method | p38 HTRF assay | THP-1 cell assay | LPS induced TNFa |
|---|---|---|---|---|---|---|
| 46 | 3-(3-(2-chloro-5-fluorophenyl)[1,2,4]triazolo[4,3-a]pyridin-7-yl)-N-cyclopropyl-4-methylbenzamide | 421.1 | B | + | + | ++ |
| 47 | 3-(3-(2-chloro-5-fluorophenyl)[1,2,4]triazolo[4,3-a]pyridin-7-yl)-4-methyl-N-(1-methyl-1H-pyrazol-5-yl)benzamide | 461.1 | B | + | + | ++ |
| 48 | 3-(3-(2-chloro-4,5-difluorophenyl)[1,2,4]triazolo-[4,3-a]pyridin-7-yl)-N-cyclopropyl-4-methylbenzamide | 439.1 | B | + | +++ | +++ |
| 49 | 3-(3-(2-chloro-4,5-difluorophenyl)[1,2,4]triazolo-[4,3-a]pyridin-7-yl)-4-methyl-N-(1-methyl-1H-pyrazol-5-yl)benzamide | 479.1 | B | + | ++ | ++ |
| 50 | N-cyclopropyl-3-(3-(1,1-dimethylethyl)[1,2,4]triazolo-[4,3-a]pyridin-7-yl)-5-fluoro-4-methylbenzamide | 367.2 | B | + | + | + |
| 51 | 3-(3-(2-chlorophenyl)[1,2,4]triazolo-[4,3-a]pyridin-7-yl)-N-cyclopropyl-5-fluoro-4-methylbenzamide | 421.2 | B | + | + | ++ |
| 52 | 3-(3-(2-chlorophenyl)[1,2,4]triazolo-[4,3-a]pyridin-7-yl)-N-ethyl-4-methylbenzamide | 391.1 | B | + | +++ | +++ |
| 53 | N-cyclopropyl-4-methyl-3-(3-(3-methyl-2-thienyl)[1,2,4]triazolo[4,3-a]pyridin-7-yl)benzamide | 389.1 | B | + | ++ | ++ |
| 54 | 4-methyl-N-(1-methyl-1H-pyrazol-5-yl)-3-(3-(3-methyl-2-thienyl)[1,2,4]triazolo[4,3-a]pyridin-7-yl)benzamide | 429.1 | B | + | + | ++ |
| 55 | 3-(3-(3-chloro-2-thienyl)[1,2,4]triazolo[4,3-a]pyridin-7-yl)-N-cyclopropyl-4-methylbenzamide | 409.1 | B | + | + | ++ |
| 56 | 3-(3-(2-chloro-6-fluorophenyl)[1,2,4]triazolo[4,3-a]pyridin-7-yl)-N-cyclopropyl-5-fluoro-4-methylbenzamide | 439.1 | B | + | + | + |
| 57 | N-cyclopropyl-4-methyl-3-(3-(4-methyl-1,3-oxazol-5-yl)[1,2,4]triazolo[4,3-a]pyridin-7-yl)benzamide | 374.1 | B | ++ | ++++ | ++++ |
| 58 | 4-methyl-3-(3-(4-methyl-1,3-oxazol-5-yl)[1,2,4]triazolo[4,3-a]pyridin-7-yl)-N-(1-methyl-1H-pyrazol-5-yl)benzamide | 412.1 | B | ++ | ++++ | ++++ |
| 59 | N-cyclopropyl-3-(3-(2,6-dichlorophenyl)[1,2,4]triazolo-[4,3-a]pyridin-7-yl)-5-fluoro-4-methylbenzamide | 457 | B | + | + | + |
| 60 | N-cyclopropyl-3-fluoro-4-methyl-5-(3-(4-methyl-1,3-oxazol-5-yl)[1,2,4]triazolo-[4,3-a]pyridin-7-yl)benzamide | 392.1 | B | + | +++ | +++ |
| 61 | 3-(3-(2-chloro-6-fluorophenyl)[1,2,4]triazolo[4,3-a]pyridin-7-yl)-5-fluoro-4-methyl-N-(1-methyl-1H-pyrazol-5-yl)benzamide | 479.3 | C | ++ | ++ | +++ |

TABLE 1-continued

| Ex. No | Name | MS (M + H+) | Method | p38 HTRF assay | THP-1 cell assay | LPS induced TNFa |
|---|---|---|---|---|---|---|
| 62 | N-cyclopropyl-3-(3-(2,6-dichlorophenyl)[1,2,4]triazolo-[4,3-a]pyridin-7-yl)-4-methylbenzamide | 439.2 | B | + | + | + |
| 63 | 3-(3-(2-chloro-6-fluorophenyl)[1,2,4]triazolo[4,3-a]pyridin-7-yl)-N-cyclopropyl-4-methylbenzamide | 421.1 | B | + | + | + |
| 64 | N-cyclopropyl-3-(3-(2,6-difluorophenyl)[1,2,4]triazolo-[4,3-a]pyridin-7-yl)-5-fluoro-4-methylbenzamide | 423.2 | B | + | + | + |
| 65 | N-cyclopropyl-3-(3-(2,6-difluorophenyl)[1,2,4]triazolo-[4,3-a]pyridin-7-yl)-4-methylbenzamide | 405.2 | B | + | + | + |
| 7 | N-cyclopropyl-4-methyl-3-(3-((1-methylethyl)amino)[1,2,4]triazolo-[4,3-a]pyridin-7-yl)benzamide | 350.4 | G | + | +++ | +++ |
| 66 | N-cyclopropyl-4-methyl-3-(3-(phenylamino)[1,2,4]triazolo-[4,3-a]pyridin-7-yl)benzamide | 384.4 | G | + | ++++ | +++ |
| 67 | N-cyclopropyl-2-fluoro-4-methyl-5-(3-(3-methyl-2-thienyl)[1,2,4]triazolo[4,3-a]pyridin-7-yl)benzamide | 407.1 | B |  | ++ | +++ |
| 68 | 2-fluoro-4-methyl-N-(1-methyl-1H-pyrazol-5-yl)-5-(3-(3-methyl-2-thienyl)[1,2,4]triazolo[4,3-a]pyridin-7-yl)benzamide | 447.2 | B |  | + | +++ |
| 69 | N-cyclopropyl-3-(3-(2-fluoro-6-(trifluoromethyl)phenyl)[1,2,4]-triazolo[4,3-a]pyridin-7-yl)-4-methylbenzamide | 455.2 | B | + | + | ++ |
| 70 | 5-(3-(2-chlorophenyl)[1,2,4]triazolo-[4,3-a]pyridin-7-yl)-N-cyclopropyl-2-fluoro-4-methylbenzamide | 421.1 | B | + | ++ | +++ |
| 71 | 5-(3-(2-chlorophenyl)[1,2,4]triazolo-[4,3-a]pyridin-7-yl)-2-fluoro-4-methyl-N-(1-methyl-1H-pyrazol-5-yl)benzamide | 461.1 | B |  | ++ | +++ |
| 72 | 5-(3-(2-chloro-6-fluorophenyl)[1,2,4]triazolo[4,3-a]pyridin-7-yl)-N-cyclopropyl-2-fluoro-4-methylbenzamide | 439.1 | B |  | ++ | ++ |
| 73 | 5-(3-(2-chloro-6-fluorophenyl)[1,2,4]triazolo[4,3-a]pyridin-7-yl)-2-fluoro-4-methyl-N-(1-methyl-1H-pyrazol-5-yl)benzamide | 479.1 | B |  | + | ++ |
| 74 | N-cyclopropyl-3-fluoro-4-methyl-5-(3-(2-(trifluoromethyl)phenyl)[1,2,4]-triazolo[4,3-a]pyridin-7-yl)benzamide | 455.1 | B | + | + | + |
| 75 | N-cyclopropyl-4-methyl-3-(3-(methyl(phenyl)amino)[1,2,4]-triazolo[4,3-a]pyridin-7-yl)benzamide | 398.4 | B | + | ++ | ++++ |
| 76 | N-cyclopropyl-3-(3-(1,1-dimethylethyl)-8-methyl[1,2,4]triazolo[4,3-a]pyridin-7-yl)-5-fluoro-4-methylbenzamide | 380.7 | B |  | ++ | +++ |
| 77 | N-cyclopropyl-3-(3-(1,1-dimethylethyl)-8-methyl[1,2,4]triazolo[4,3-a]pyridin-7-yl)-4-methylbenzamide | 363 | B |  | ++ | +++ |

TABLE 1-continued

| Ex. No | Name | MS (M + H+) | Method | p38 HTRF assay | THP-1 cell assay | LPS induced TNFa |
|---|---|---|---|---|---|---|
| 78 | 3-(3-(2-chlorophenyl)-8-methyl[1,2,4]triazolo[4,3-a]pyridin-7-yl)-N-cyclopropyl-4-methylbenzamide | 417.2 | B | ++ | ++ | ++++ |
| 79 | 3-(3-(3-chloro-4-pyridinyl)[1,2,4]triazolo[4,3-a]pyridin-7-yl)-N-cyclopropyl-5-fluoro-4-methylbenzamide | 422.1 | B | + | + | ++ |
| 80 | 3-(3-(3-chloro-4-pyridinyl)[1,2,4]triazolo[4,3-a]pyridin-7-yl)-N-cyclopropyl-4-methylbenzamide | 404.1 | B | + | + | ++ |
| 81 | 3-(3-(2-chloro-6-methylphenyl)[1,2,4]triazolo-[4,3-a]pyridin-7-yl)-N-cyclopropyl-4-methylbenzamide | 417.2 | B | + | + | + |
| 82 | N-cyclopropyl-3-fluoro-4-methyl-5-(3-(2-methylphenyl)[1,2,4]triazolo-[4,3-a]pyridin-7-yl)benzamide | 401.1 | B | + | + | + |
| 83 | N-cyclopropyl-3-fluoro-5-(3-(2-fluoro-6-methylphenyl)[1,2,4]triazolo-[4,3-a]pyridin-7-yl)-4-methylbenzamide | 419.1 | B | + | + | + |
| 84 | N-cyclopropyl-3-(3-(2-fluoro-6-methylphenyl)[1,2,4]triazolo-[4,3-a]pyridin-7-yl)-4-methylbenzamide | 401.1 | B | + | | |
| 85 | N-cyclopropyl-4-methyl-3-(3-(2-(methyloxy)phenyl)[1,2,4]triazolo-[4,3-a]pyridin-7-yl)benzamide | 399.2 | B | + | | |
| 86 | N-cyclopropyl-4-methyl-3-(3-((1S)-2,2,2-trifluoro-1-methylethyl)[1,2,4]triazolo[4,3-a]pyridin-7-yl)benzamide | 389.2 | B | | | |
| 87 | N-cyclopropyl-4-methyl-3-(3-((1R)-2,2,2-trifluoro-1-methylethyl)[1,2,4]triazolo[4,3-a]pyridin-7-yl)benzamide | 389.2 | B | | ++ | +++ |
| 88 | 1,1-dimethylethyl 2-((3-(3-(2-chlorophenyl)[1,2,4]triazolo-[4,3-a]pyridin-7-yl)-4-methylphenyl)carbonyl)hydrazinecarboxylate | 478.1 | E | | | |
| 5 | 3-(3-(2-chlorophenyl)[1,2,4]triazolo-[4,3-a]pyridin-7-yl)-4-methylbenzohydrazide | 378 | E | | | |
| 89 | N-cyclopropyl-4-methyl-3-(3-(phenylmethyl)[1,2,4]triazolo-[4,3-a]pyridin-7-yl)benzamide | 383.2 | B | + | +++ | ++++ |
| 90 | 2-chloro-5-(3-(2-chlorophenyl)[1,2,4]triazolo-[4,3-a]pyridin-7-yl)-N-cyclopropyl-4-methylbenzamide | 437.1 | B | ++++ | +++++ | ++++++ |
| 91 | 3-(3-(2-chloro-6-methylphenyl)[1,2,4]triazolo-[4,3-a]pyridin-7-yl)-N-cyclopropyl-5-fluoro-4-methylbenzamide | 435.2 | B | + | + | + |
| 92 | 3-(3-(2,6-difluorophenyl)[1,2,4]triazolo-[4,3-a]pyridin-7-yl)-5-fluoro-N-3-isoxazolyl-4-methylbenzamide | 450 | C | + | + | + |

TABLE 1-continued

| Ex. No | Name | MS (M + H+) | Method | p38 HTRF assay | THP-1 cell assay | LPS induced TNFa |
|---|---|---|---|---|---|---|
| 6 | 3-(3-(2-chlorophenyl)-5-methyl[1,2,4]triazolo[4,3-a]pyridin-7-yl)-N-cyclopropyl-4-methylbenzamide | 417.2 | F | + | + | ++ |
| 93 | N-cyclopropyl-3-(3-cyclopropyl[1,2,4]triazolo[4,3-a]pyridin-7-yl)-4-methylbenzamide | 333.2 | B | + | ++ | +++ |
| 94 | 3-(3-cyclohexyl[1,2,4]triazolo[4,3-a]pyridin-7-yl)-N-cyclopropyl-4-methylbenzamide | 375.2 | B | + | ++ | +++ |
| 95 | 3-(3-cyclopentyl[1,2,4]triazolo[4,3-a]pyridin-7-yl)-N-cyclopropyl-4-methylbenzamide | 361.2 | B | + | + | ++ |
| 96 | N-cyclopropyl-4-methyl-3-(3-(1-pyrrolidinyl)[1,2,4]triazolo[4,3-a]pyridin-7-yl)benzamide | 362.2 | B | + | ++ | ++++ |
| 97 | N-cyclopropyl-4-methyl-3-(3-(tetrahydro-2H-pyran-4-yl)[1,2,4]triazolo[4,3-a]pyridin-7-yl)benzamide | 377.2 | B | + | ++ | +++ |
| 98 | N-cyclopropyl-4-methyl-3-(3-((3s,5s,7s)-tricyclo[3.3.1.1~3,7~]dec-1-yl)[1,2,4]triazolo[4,3-a]pyridin-7-yl)benzamide | 427.2 | B | + | ++ | +++ |
| 99 | N-cyclopropyl-4-methyl-3-(3-(1-piperidinyl)[1,2,4]triazolo[4,3-a]pyridin-7-yl)benzamide | 376.2 | B | + | ++ | ++++ |
| 100 | N-cyclopropyl-4-methyl-3-(3-(2-oxo-1-imidazolidinyl)[1,2,4]triazolo-[4,3-a]pyridin-7-yl)benzamide | 377.2 | B | | ++++ | +++++ |
| 101 | N-cyclopropyl-4-methyl-3-(3-(4-morpholinyl)[1,2,4]triazolo[4,3-a]pyridin-7-yl)benzamide | 378.2 | B | ++ | +++ | +++ |
| 102 | N-cyclopropyl-4-methyl-3-(3-(trifluoromethyl)[1,2,4]triazolo-[4,3-a]pyridin-7-yl)benzamide | 361.1 | B | +++ | ++++ | ++++ |
| 103 | N-cyclopropyl-3-(3-(2-ethylphenyl)[1,2,4]triazolo[4,3-a]pyridin-7-yl)-4-methylbenzamide | 397.2 | B | + | ++ | +++ |
| 104 | N-cyclopropyl-4-methyl-3-(3-(2-(trifluoromethyl)phenyl)[1,2,4]-triazolo[4,3-a]pyridin-7-yl)benzamide | 437.2 | B | + | ++ | +++ |
| 105 | N-cyclopropyl-3-(3-(1,1-dimethylethyl)[1,2,4]triazolo-[4,3-a]pyridin-7-yl)-4-methylbenzamide | 349.2 | B | + | ++ | ++ |
| 106 | 3-(3-(2,6-difluorophenyl)[1,2,4]triazolo-[4,3-a]pyridin-7-yl)-N-3-isoxazolyl-4-methylbenzamide | 432.1 | C | + | + | + |
| 107 | N-cyclopropyl-3-(3-(1,1-dimethylethyl)-8-methyl[1,2,4]triazolo[4,3-a]pyridin-7-yl)-5-fluoro-4-methylbenzamide | 381 | B | | ++ | +++ |

TABLE 1-continued

| Ex. No | Name | MS (M + H+) | Method | p38 HTRF assay | THP-1 cell assay | LPS induced TNFa |
|---|---|---|---|---|---|---|
| 108 | N-cyclopropyl-3-(3-(1,1-dimethylethyl)-8-methyl[1,2,4]triazolo[4,3-a]pyridin-7-yl)-4-methylbenzamide | 362.9 | B | | ++ | +++ |

Data Key:
"+++++" designates an IC$_{50}$ value in the range beginning from 1.0 uM and ending at 5.0 uM;
"++++" designates an IC$_{50}$ value in the range beginning from 250 nM and ending at 1.0 uM;
"+++" designates an IC$_{50}$ value in the range beginning from 100 nM and ending at 250 nM;
"++" designates an IC$_{50}$ value in the range beginning from 25 nM and ending at 100 nM; and
"+" designates an IC$_{50}$ value of less than 25 nM.

The following compounds in Tables 2 and 3 are additional representative examples of Formula I, as provided by the present invention.

TABLE 2

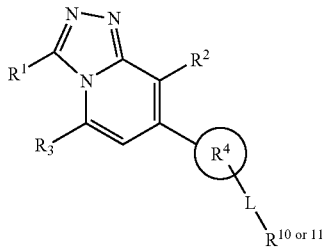

| Ex. No. | R$^1$ | R$^3$ | R$^5$ | L | R$^{10}$ or R$^{11}$ |
|---|---|---|---|---|---|
| 34 | 1-morpholinyl | 2-CH$_3$-phenyl | H | m-C(O)NH— | Methyl or cyclopropyl |
| 35 | 1-piperazinyl | 4-CH$_3$-phenyl | H | m-C(O)NH— | Methyl or cyclopropyl |
| 36 | 1-piperidinyl | phenyl | H | m-C(O)NH— | Methyl or cyclopropyl |
| 37 | cyclohexyl-N— | 6-CH$_3$-phenyl | H | m-C(O)NH— | Methyl or cyclopropyl |
| 38 | morpholine-(CH$_2$)$_2$—N— | 2-OCH$_3$-phenyl | H | m-C(O)NH— | Methyl or cyclopropyl |
| 39 | (CH$_3$)$_2$N—(CH$_2$)$_2$—N— | 4-OCH$_3$-phenyl | H | m-C(O)NH— | Methyl or cyclopropyl |
| 40 | (C$_2$H$_5$)$_2$N—(CH$_2$)$_2$—N— | phenyl | H | m-C(O)NH— | Methyl or cyclopropyl |
| 41 | 3-OH-1-pyrrolidinyl | 6-OCH$_3$-phenyl | H | m-C(O)NH— | Methyl or cyclopropyl |
| 42 | 3-amido-1-pyrrolidinyl | 6-OCH$_3$-phenyl | H | m-C(O)NH— | Methyl or cyclopropyl |
| 43 | 4-amido-1-piperidinyl | 2-F-phenyl | H | m-C(O)NH— | Methyl or cyclopropyl |
| 44 | 3-amido-1-piperidinyl | 2-F-phenyl | H | m-C(O)NH— | Methyl or cyclopropyl |
| 45 | 4N—CH$_3$-1-piperizinyl | 4-F-phenyl | H | m-C(O)NH— | Methyl or cyclopropyl |
| 46 | 2-cl-phenyl | phenyl | H | m-C(O)NH— | Methyl or cyclopropyl |
| 47 | 2-CH$_3$-phenyl | 6-F-phenyl | H | m-C(O)NH— | Methyl or cyclopropyl |
| 48 | 4-CH$_3$-phenyl | 2-thiophene | H | m-C(O)NH— | Methyl or cyclopropyl |
| 49 | 4-cl-phenyl | 3-thiophene | H | m-C(O)NH— | Methyl or cyclopropyl |
| 50 | 3-cl-phenyl | 2-pyridine | H | m-C(O)NH— | Methyl or cyclopropyl |
| 51 | 3-CH$_3$-phenyl | 3-pyridine | H | m-C(O)NH— | Methyl or cyclopropyl |

TABLE 2-continued

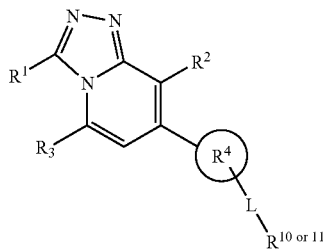

| Ex. No. | R¹ | R³ | R⁵ | L | R¹⁰ or R¹¹ |
|---|---|---|---|---|---|
| 52 | 2-thiophene | 2-CH₃-phenyl | H | m-C(O)NH— | Methyl or cyclopropyl |
| 53 | 3-thiophene | 4-CH₃-phenyl | H | m-C(O)NH— | Methyl or cyclopropyl |
| 54 | 2-pyridine | phenyl | H | m-C(O)NH— | Methyl or cyclopropyl |
| 55 | 1-morpholinyl | 2-CH₃-phenyl | H | m-C(O)NH— | ethyl |
| 56 | 1-piperazinyl | 4-CH₃-phenyl | H | m-C(O)NH— | ethyl |
| 57 | 1-piperidinyl | phenyl | H | m-C(O)NH— | ethyl |
| 58 | cyclohexyl-N— | 6-CH₃-phenyl | H | m-C(O)NH— | ethyl |
| 59 | morpholine-(CH₂)₂—N— | 2-OCH₃-phenyl | H | m-C(O)NH— | ethyl |
| 60 | (CH₃)₂N—(CH₂)₂—N— | 4-OCH₃-phenyl | H | m-C(O)NH— | ethyl |
| 61 | (C₂H₅)₂N—(CH₂)₂—N— | phenyl | H | m-C(O)NH— | ethyl |
| 62 | 3-OH-1-pyrrolidinyl | 6-OCH₃-phenyl | H | m-C(O)NH— | ethyl |
| 63 | 3-amido-1-pyrrolidinyl | 6-OCH₃-phenyl | H | m-C(O)NH— | ethyl |
| 64 | 3-amido-1-piperidinyl | 2-F-phenyl | H | m-C(O)NH— | ethyl |
| 65 | 4-amido-1-piperidinyl | 2-F-phenyl | H | m-C(O)NH— | ethyl |
| 66 | 4N—CH₃-1-piperizinyl | 4-F-phenyl | H | m-C(O)NH— | ethyl |
| 67 | 2-cl-phenyl | phenyl | H | m-C(O)NH— | ethyl |
| 68 | 2-CH₃-phenyl | 6-F-phenyl | H | m-C(O)NH— | ethyl |
| 69 | 4-CH₃-phenyl | 2-thiophene | H | m-C(O)NH— | ethyl |
| 70 | 4-cl-phenyl | 3-thiophene | H | m-C(O)NH— | ethyl |
| 71 | 3-cl-phenyl | 2-pyridine | H | m-C(O)NH— | ethyl |
| 72 | 3-CH₃-phenyl | 3-pyridine | H | m-C(O)NH— | ethyl |
| 73 | 2-thiophene | 2-CH₃-phenyl | H | m-C(O)NH— | ethyl |
| 74 | 3-thiophene | 4-CH₃-phenyl | H | m-C(O)NH— | ethyl |
| 75 | 2-pyridine | phenyl | H | m-C(O)NH— | ethyl |
| 76 | 1-morpholinyl | 2-CH₃-phenyl | H | m-C(O)NH— | propyl |
| 77 | 1-piperazinyl | 4-CH₃-phenyl | H | m-C(O)NH— | propyl |
| 78 | 1-piperidinyl | phenyl | H | m-C(O)NH— | propyl |
| 79 | cyclohexyl-N— | 6-CH₃-phenyl | H | m-C(O)NH— | propyl |
| 80 | morpholine-(CH₂)₂—N— | 2-OCH₃-phenyl | H | m-C(O)NH— | propyl |
| 81 | (CH₃)₂N—(CH₂)₂—N— | 4-OCH₃-phenyl | H | m-C(O)NH— | propyl |
| 82 | (C₂H₅)₂N—(CH₂)₂—N— | phenyl | H | m-C(O)NH— | propyl |
| 83 | 3-OH-1-pyrrolidinyl | 6-OCH₃-phenyl | H | m-C(O)NH— | propyl |
| 84 | 3-amido-1-pyrrolidinyl | 6-OCH₃-phenyl | H | m-C(O)NH— | propyl |
| 85 | 3-amido-1-piperidinyl | 2-F-phenyl | H | m-C(O)NH— | propyl |
| 86 | 4-amido-1-piperidinyl | 2-F-phenyl | H | m-C(O)NH— | propyl |
| 87 | 4N—CH₃-1-piperizinyl | 4-F-phenyl | H | m-C(O)NH— | propyl |
| 88 | 2-cl-phenyl | phenyl | H | m-C(O)NH— | propyl |
| 89 | 2-CH₃-phenyl | 6-F-phenyl | H | m-C(O)NH— | propyl |
| 90 | 4-CH₃-phenyl | 2-thiophene | H | m-C(O)NH— | propyl |
| 91 | 4-cl-phenyl | 3-thiophene | H | m-C(O)NH— | propyl |
| 92 | 3-cl-phenyl | 2-pyridine | H | m-C(O)NH— | propyl |
| 93 | 3-CH₃-phenyl | 3-pyridine | H | m-C(O)NH— | propyl |
| 94 | 2-thiophene | 2-CH₃-phenyl | H | m-C(O)NH— | propyl |
| 95 | 3-thiophene | 4-CH₃-phenyl | H | m-C(O)NH— | propyl |
| 96 | 2-pyridine | phenyl | H | m-C(O)NH— | propyl |
| 97 | 4-F-phenyl | H | CH₃ | m-C(O)NH— | cyclopropyl |

TABLE 3

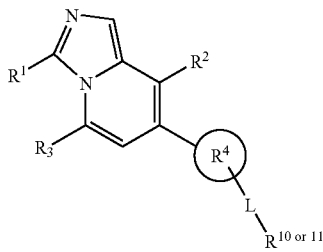

| Ex. No. | $R^1$ | $R^3$ | $R^5$ | L | $R^{10}$ or $R^{11}$ |
|---|---|---|---|---|---|
| 98 | 1-morpholinyl | 2-CH$_3$-phenyl | H | m-C(O)NH— | Methyl or cyclopropyl |
| 99 | 1-piperazinyl | 4-CH$_3$-phenyl | H | m-C(O)NH— | Methyl or cyclopropyl |
| 100 | 1-piperidinyl | phenyl | H | m-C(O)NH— | Methyl or cyclopropyl |
| 101 | cyclohexyl-N— | 6-CH$_3$-phenyl | H | m-C(O)NH— | Methyl or cyclopropyl |
| 102 | morpholine-(CH$_2$)$_2$—N— | 2-OCH$_3$-phenyl | H | m-C(O)NH— | Methyl or cyclopropyl |
| 103 | (CH$_3$)$_2$N—(CH$_2$)$_2$—N— | 4-OCH$_3$-phenyl | H | m-C(O)NH— | Methyl or cyclopropyl |
| 104 | (C$_2$H$_5$)$_2$N—(CH$_2$)$_2$—N— | phenyl | H | m-C(O)NH— | Methyl or cyclopropyl |
| 105 | 3-OH-1-pyrrolidinyl | 6-OCH$_3$-phenyl | H | m-C(O)NH— | Methyl or cyclopropyl |
| 106 | 3-amido-1-pyrrolidinyl | 6-OCH$_3$-phenyl | H | m-C(O)NH— | Methyl or cyclopropyl |
| 107 | 4-amido-1-piperidinyl | 2-F-phenyl | H | m-C(O)NH— | Methyl or cyclopropyl |
| 108 | 3-amido-1-piperidinyl | 2-F-phenyl | H | m-C(O)NH— | Methyl or cyclopropyl |
| 109 | 4N—CH$_3$-1-piperizinyl | 4-F-phenyl | H | m-C(O)NH— | Methyl or cyclopropyl |
| 110 | 2-cl-phenyl | phenyl | H | m-C(O)NH— | Methyl or cyclopropyl |
| 111 | 2-CH$_3$-phenyl | 6-F-phenyl | H | m-C(O)NH— | Methyl or cyclopropyl |
| 112 | 4-CH$_3$-phenyl | 2-thiophene | H | m-C(O)NH— | Methyl or cyclopropyl |
| 113 | 4-cl-phenyl | 3-thiophene | H | m-C(O)NH— | Methyl or cyclopropyl |
| 114 | 3-cl-phenyl | 2-pyridine | H | m-C(O)NH— | Methyl or cyclopropyl |
| 115 | 3-CH$_3$-phenyl | 3-pyridine | H | m-C(O)NH— | Methyl or cyclopropyl |
| 116 | 2-thiophene | 2-CH$_3$-phenyl | H | m-C(O)NH— | Methyl or cyclopropyl |
| 117 | 3-thiophene | 4-CH$_3$-phenyl | H | m-C(O)NH— | Methyl or cyclopropyl |
| 118 | 2-pyridine | phenyl | H | m-C(O)NH— | Methyl or cyclopropyl |
| 119 | 1-morpholinyl | 2-CH$_3$-phenyl | H | m-C(O)NH— | ethyl |
| 120 | 1-piperazinyl | 4-CH$_3$-phenyl | H | m-C(O)NH— | ethyl |
| 121 | 1-piperidinyl | phenyl | H | m-C(O)NH— | ethyl |
| 122 | cyclohexyl-N— | 6-CH$_3$-phenyl | H | m-C(O)NH— | ethyl |
| 123 | morpholine-(CH$_2$)$_2$—N— | 2-OCH$_3$-phenyl | H | m-C(O)NH— | ethyl |
| 124 | (CH$_3$)$_2$N—(CH$_2$)$_2$—N— | 4-OCH$_3$-phenyl | H | m-C(O)NH— | ethyl |
| 125 | (C$_2$H$_5$)$_2$N—(CH$_2$)$_2$—N— | phenyl | H | m-C(O)NH— | ethyl |
| 126 | 3-OH-1-pyrrolidinyl | 6-OCH$_3$-phenyl | H | m-C(O)NH— | ethyl |
| 127 | 3-amido-1-pyrrolidinyl | 6-OCH$_3$-phenyl | H | m-C(O)NH— | ethyl |
| 128 | 3-amido-1-piperidinyl | 2-F-phenyl | H | m-C(O)NH— | ethyl |
| 129 | 4-amido-1-piperidinyl | 2-F-phenyl | H | m-C(O)NH— | ethyl |
| 130 | 4N—CH$_3$-1-piperizinyl | 4-F-phenyl | H | m-C(O)NH— | ethyl |
| 131 | 2-cl-phenyl | phenyl | H | m-C(O)NH— | ethyl |
| 132 | 2-CH$_3$-phenyl | 6-F-phenyl | H | m-C(O)NH— | ethyl |

TABLE 3-continued

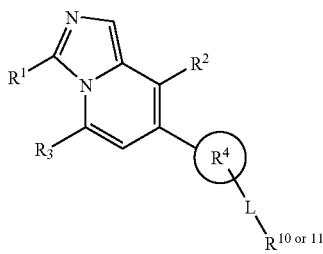

| Ex. No. | $R^1$ | $R^3$ | $R^5$ | L | $R^{10}$ or $R^{11}$ |
|---|---|---|---|---|---|
| 133 | 4-CH₃-phenyl | 2-thiophene | H | m-C(O)NH— | ethyl |
| 134 | 4-cl-phenyl | 3-thiophene | H | m-C(O)NH— | ethyl |
| 135 | 3-cl-phenyl | 2-pyridine | H | m-C(O)NH— | ethyl |
| 136 | 3-CH₃-phenyl | 3-pyridine | H | m-C(O)NH— | ethyl |
| 137 | 2-thiophene | 2-CH₃-phenyl | H | m-C(O)NH— | ethyl |
| 138 | 3-thiophene | 4-CH₃-phenyl | H | m-C(O)NH— | ethyl |
| 139 | 2-pyridine | phenyl | H | m-C(O)NH— | ethyl |
| 140 | 1-morpholinyl | 2-CH₃-phenyl | H | m-C(O)NH— | propyl |
| 141 | 1-piperazinyl | 4-CH₃-phenyl | H | m-C(O)NH— | propyl |
| 142 | 1-piperidinyl | phenyl | H | m-C(O)NH— | propyl |
| 143 | cyclohexyl-N— | 6-CH₃-phenyl | H | m-C(O)NH— | propyl |
| 144 | morpholine-(CH₂)₂—N— | 2-OCH₃-phenyl | H | m-C(O)NH— | propyl |
| 145 | (CH₃)₂N—(CH₂)₂—N— | 4-OCH₃-phenyl | H | m-C(O)NH— | propyl |
| 146 | (C₂H₅)₂N—(CH₂)₂—N— | phenyl | H | m-C(O)NH— | propyl |
| 147 | 3-OH-1-pyrrolidinyl | 6-OCH₃-phenyl | H | m-C(O)NH— | propyl |
| 148 | 3-amido-1-pyrrolidinyl | 6-OCH₃-phenyl | H | m-C(O)NH— | propyl |
| 149 | 3-amido-1-piperidinyl | 2-F-phenyl | H | m-C(O)NH— | propyl |
| 150 | 4-amido-1-piperidinyl | 2-F-phenyl | H | m-C(O)NH— | propyl |
| 151 | 4N—CH₃-1-piperizinyl | 4-F-phenyl | H | m-C(O)NH— | propyl |
| 152 | 2-cl-phenyl | phenyl | H | m-C(O)NH— | propyl |
| 153 | 2-CH₃-phenyl | 6-F-phenyl | H | m-C(O)NH— | propyl |
| 154 | 4-CH₃-phenyl | 2-thiophene | H | m-C(O)NH— | propyl |
| 155 | 4-cl-phenyl | 3-thiophene | H | m-C(O)NH— | propyl |
| 156 | 3-cl-phenyl | 2-pyridine | H | m-C(O)NH— | propyl |
| 157 | 3-CH₃-phenyl | 3-pyridine | H | m-C(O)NH— | propyl |
| 158 | 2-thiophene | 2-CH₃-phenyl | H | m-C(O)NH— | propyl |
| 159 | 3-thiophene | 4-CH₃-phenyl | H | m-C(O)NH— | propyl |
| 160 | 2-pyridine | phenyl | H | m-C(O)NH— | propyl |
| 161 | 4-F-phenyl | H | CH₃ | m-C(O)NH— | cyclopropyl |

While the examples described above provide processes for synthesizing compounds of Formulas I and II, it should be appreciated that other methods may be utilized to prepare such compounds. Methods involving the use of protecting groups may be used. Particularly, if one or more functional groups, for example carboxy, hydroxy, amino, or mercapto groups, are or need to be protected in preparing the compounds of the invention, because they are not intended to take part in a specific reaction or chemical transformation, various known conventional protecting groups may be used. Protecting groups typically utilized in the synthesis of natural and synthetic compounds, including peptides, nucleic acids, derivatives thereof and sugars, having multiple reactive centers, chiral centers and other sites potentially susceptible to the reaction reagents and/or conditions, may be used.

The protection of functional groups by protecting groups, the protecting groups themselves, and their removal reactions (commonly referred to as "deprotection") are described, for example, in standard reference works, such as J. F. W. McOmie, Protective Groups in Organic Chemistry, Plenum Press, London and New York (1973), in T. W. Greene, Protective Groups in Organic Synthesis, Wiley, New York (1981), in The Peptides, Volume 3, E. Gross and J. Meienhofer editors, Academic Press, London and New York (1981), in Methoden der Organischen Chemie (Methods of Organic Chemistry), Houben Weyl, 4$^{th}$ edition, Volume 15/1, Georg Thieme Verlag, Stuttgart (1974), in H.-D. Jakubke and H. Jescheit, Aminosaüren, Peptide, Proteine (Amino Acids, Peptides, Proteins), Verlag Chemie, Weinheim, Deerfield Beach, and Basel (1982), and in Jochen Lehmann, Chemie der Kohlenhydrate: Monosaccharide und Derivate (Chemistry of Carbohydrates: Monosaccharides and Derivatives), Georg Thieme Verlag, Stuttgart (1974).

Salts of a compound of the invention having a salt-forming group may be prepared in a conventional manner or manner known to persons skilled in the art. For example, acid addition salts of compounds of the invention may be obtained by treatment with an acid or with a suitable anion exchange reagent. A salt with two acid molecules (for example a dihalogenide) may also be converted into a salt with one acid molecule per compound (for example a monohalogenide); this may be done by heating to a melt, or for example by heating as a solid under a high vacuum at elevated temperature, for example from 50° C. to 170° C., one molecule of the acid being expelled per molecule of the compound.

Acid salts can usually be converted to free-base compounds, e.g. by treating the salt with suitable basic agents, for example with alkali metal carbonates, alkali metal hydrogen carbonates, or alkali metal hydroxides, typically potassium carbonate or sodium hydroxide. Exemplary salt forms and their preparation are described herein in the Definition section of the application.

All synthetic procedures described herein can be carried out under known reaction conditions, advantageously under those described herein, either in the absence or in the presence (usually) of solvents or diluents. As appreciated by those of ordinary skill in the art, the solvents should be inert with respect to, and should be able to dissolve, the starting materials and other reagents used. Solvents should be able to partially or wholly solubilize the reactants in the absence or presence of catalysts, condensing agents or neutralizing agents, for example ion exchangers, typically cation exchangers for example in the $H^+$ form. The ability of the solvent to allow and/or influence the progress or rate of the reaction is generally dependant on the type and properties of the solvent(s), the reaction conditions including temperature, pressure, atmospheric conditions such as in an inert atmosphere under argon or nitrogen, and concentration, and of the reactants themselves.

Suitable solvents for conducting reactions to synthesize compounds of the invention include, without limitation, water; esters, including lower alkyl-lower alkanoates, e.g., ethyl acetate; ethers including aliphatic ethers, e.g., $Et_2O$ and ethylene glycol dimethylether or cyclic ethers, e.g., THF; liquid aromatic hydrocarbons, including benzene, toluene and xylene; alcohols, including MeOH, EtOH, 1-propanol, IPOH, n- and t-butanol; nitriles including $CH_3CN$; halogenated hydrocarbons, including $CH_2Cl_2$, $CHCl_3$ and $CCl_4$; acid amides including DMF; sulfoxides, including DMSO; bases, including heterocyclic nitrogen bases, e.g. pyridine; carboxylic acids, including lower alkanecarboxylic acids, e.g., AcOH; inorganic acids including HCl, HBr, HF, $H_2SO_4$ and the like; carboxylic acid anhydrides, including lower alkane acid anhydrides, e.g., acetic anhydride; cyclic, linear, or branched hydrocarbons, including cyclohexane, hexane, pentane, isopentane and the like, and mixtures of these solvents, such as purely organic solvent combinations, or water-containing solvent combinations e.g., aqueous solutions. These solvents and solvent mixtures may also be used in "working-up" the reaction as well as in processing the reaction and/or isolating the reaction product(s), such as in chromatography.

The invention further encompasses "intermediate" compounds, including structures produced from the synthetic procedures described, whether isolated or not, prior to obtaining the finally desired compound. Structures resulting from carrying out steps from a transient starting material, structures resulting from divergence from the described method(s) at any stage, and structures forming starting materials under the reaction conditions are all "intermediates" included in the invention. Further, structures produced by using starting materials in the form of a reactive derivative or salt, or produced by a compound obtainable by means of the process according to the invention and structures resulting from processing the compounds of the invention in situ are also within the scope of the invention.

For example, triazolopyridine building blocks or intermediates I may generally be prepared via a dehydration or oxidative cyclization route from a suitably derivatized heteroaryl hydrazine of type II, III or IV.

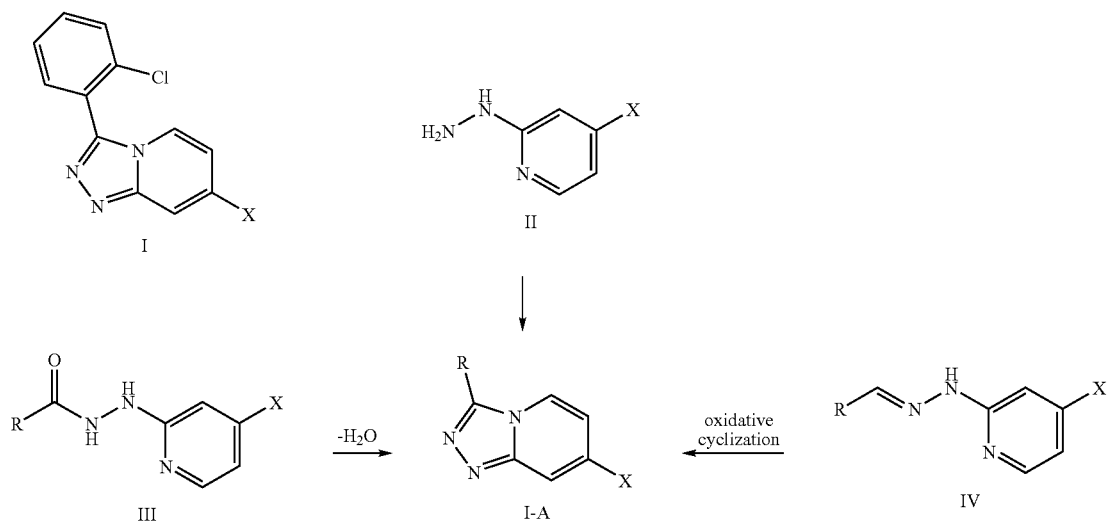

Another approach may be:

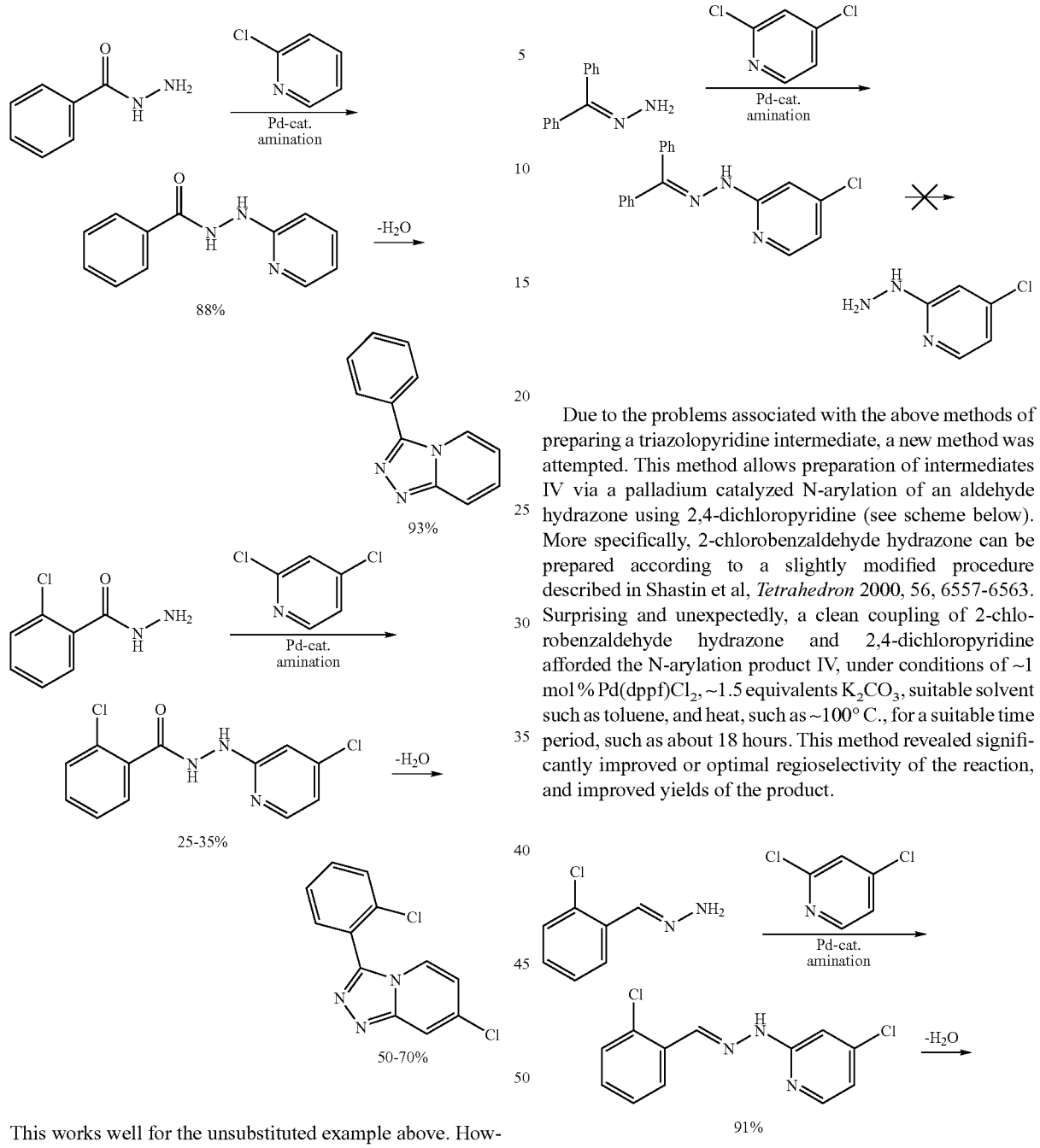

This works well for the unsubstituted example above. However, when you attempt this method with more functionalized coupling partners, such as the chloro-substituted material illustrated above, additional regioselectivity, oligomerization and reactivity issues are introduced which need to be overcome to be more effective.

Yet another approach to prepare intermediates III or IV (see scheme below), may be via the arylation of benzophenone hydrazone (see Mauger, C.; Mignani, G. *Synthetic Comm.* 2006, 36, 1123-1129), liberation of an intermediate II, followed by suitable derivatization to afford III or IV. A palladium catalyzed arylation reaction using 2,4-dichloropyridine afforded 2-regioisomer as a single product. However, conversion to the corresponding hydrazine failed.

Due to the problems associated with the above methods of preparing a triazolopyridine intermediate, a new method was attempted. This method allows preparation of intermediates IV via a palladium catalyzed N-arylation of an aldehyde hydrazone using 2,4-dichloropyridine (see scheme below). More specifically, 2-chlorobenzaldehyde hydrazone can be prepared according to a slightly modified procedure described in Shastin et al, *Tetrahedron* 2000, 56, 6557-6563. Surprising and unexpectedly, a clean coupling of 2-chlorobenzaldehyde hydrazone and 2,4-dichloropyridine afforded the N-arylation product IV, under conditions of ~1 mol % Pd(dppf)Cl$_2$, ~1.5 equivalents K$_2$CO$_3$, suitable solvent such as toluene, and heat, such as ~100° C., for a suitable time period, such as about 18 hours. This method revealed significantly improved or optimal regioselectivity of the reaction, and improved yields of the product.

This newly discovered method may be applied more generally as well. For example, it is contemplated that aryl hyradazines may be made as follows, effectively in good yields. The Pd-catalyzed conditions are the same or similar to those used above.

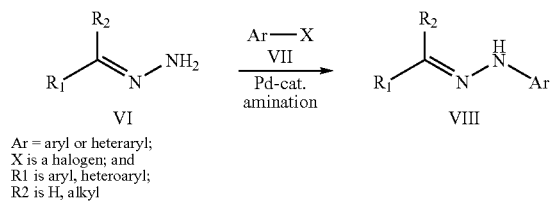

Ar = aryl or heteraryl;
X is a halogen; and
R1 is aryl, heteroaryl;
R2 is H, alkyl Further, generally this method can be used to prepare the following compounds and intermediates.

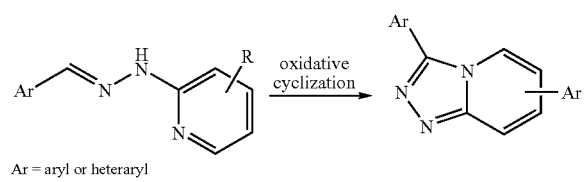

Ar = aryl or heteraryl

Some of the intermediates which have been obtained using this more efficient method, include

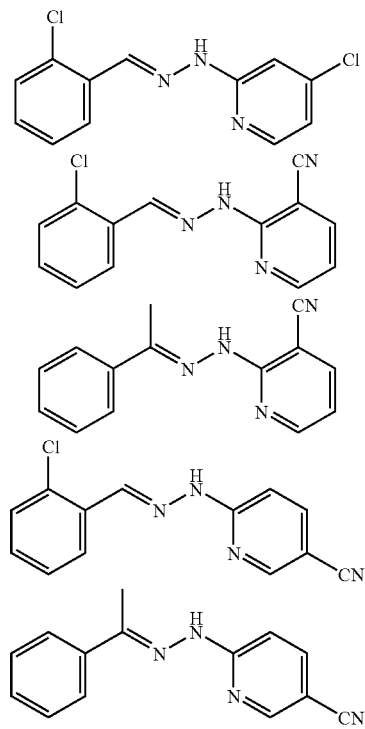

New starting materials and/or intermediates, as well as processes for the preparation thereof, are likewise the subject of this invention. In select embodiments, such starting materials are used and reaction conditions so selected as to obtain the desired compound(s).

Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups may be protected with suitable protecting groups when necessary. Protecting groups, their introduction and removal are described above.

In synthesizing a compound of formulas I and II according to a desired procedure, the steps may be performed in an order suitable to prepare the compound, including a procedure described herein or by an alternate order of steps described herein, and may be preceded, or followed, by additional protection/deprotection steps as necessary. The procedures may further use appropriate reaction conditions, including inert solvents, additional reagents, such as bases (e.g., LDA, DIEA, pyridine, $K_2CO_3$, and the like), catalysts, and salt forms of the above. The intermediates may be isolated or carried on in situ, with or without purification. Purification methods are known in the art and include, for example, crystallization, chromatography (liquid and gas phase, and the like), extraction, distillation, trituration, reverse phase HPLC and the like. Reactions conditions such as temperature, duration, pressure, and atmosphere (inert gas, ambient) are known in the art and may be adjusted as appropriate for the reaction. Synthetic chemistry transformations and protecting group methodologies (protection and deprotection) useful in synthesizing the inhibitor compounds described herein are known in the art and include, for example, those such as described in R. Larock, Comprehensive Organic Transformations, VCH Publishers (1989); T. W. Greene and P. G. M. Wuts, Protective Groups in Organic Synthesis, $3^{rd}$ edition, John Wiley and Sons (1999); L. Fieser and M. Fieser, Fieser and Fieser's Reagents for Organic Synthesis, John Wiley and Sons (1994); A. Katritzky and A. Pozharski, Handbook of Heterocyclic Chemistry, $2^{nd}$ edition (2001); M. Bodanszky, A. Bodanszky, The Practice of Peptide Synthesis, Springer-Verlag, Berlin Heidelberg (1984); J. Seyden-Penne, Reductions by the Alumino- and Borohydrides in Organic Synthesis, $2^{nd}$ edition, Wiley-VCH, (1997); and L. Paquette, editor, Encyclopedia of Reagents for Organic Synthesis, John Wiley and Sons (1995).

In one embodiment, the present invention provides a method of making a compound of Formula I or II, the method comprising the step of reacting a compound 7,

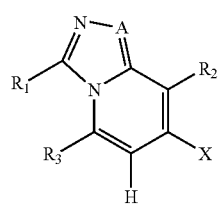

7 wherein A, $R^1$, $R^2$ and $R^3$ are as defined herein in Formulas I or II and X is a halogen such as a bromide, with a boronic acid having a general formula

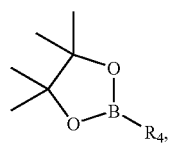

wherein $R^4$ is defined herein, to make a compound of Formula I or II.

In another embodiment, there is provided a method of making a compound of Formula II, the method comprising the step of reacting a compound 7,

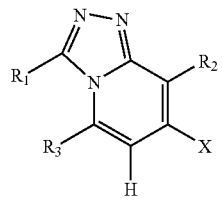

wherein A, $R^1$, $R^2$ and $R^3$ are as defined herein and X is a halogen, with a boronic acid having a general formula

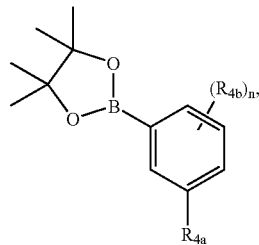

wherein $R^{4a}$, $R^{4b}$ and in are as defined herein, to make a compound of Formula II.

Compounds of the present invention can possess, in general, one or more asymmetric carbon atoms and are thus capable of existing in the form of optical isomers including, without limitation, racemates and racemic mixtures, scalemic mixtures, single enantiomers, individual diastereomers and diastereomeric mixtures. All such isomeric forms of these compounds are expressly included in the present invention. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using optically active starting materials. These isomers may be in the form of a free acid, a free base, an ester or a salt.

The compounds of this invention may also be represented in multiple tautomeric forms. The invention expressly includes all tautomeric forms of the compounds described herein.

The compounds may also occur in cis- or trans- or E- or Z-double bond isomeric forms. All such isomeric forms of such compounds are expressly included in the present invention. All crystal forms of the compounds described herein are expressly included in the present invention.

Substituents on ring moieties (e.g., phenyl, thienyl, etc.) may be attached to specific atoms, whereby they are intended to be fixed to that atom, or they may be drawn unattached to a specific atom, whereby they are intended to be attached at any available atom that is not already substituted by an atom other than H (hydrogen).

The compounds of this invention may contain heterocyclic ring systems attached to another ring system. Such heterocyclic ring systems may be attached through a carbon atom or a heteroatom in the ring system.

The compounds of the invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion. By way of example, a compound of the invention may be modified to incorporate a hydrophobic group or "greasy" moiety in an attempt to enhance the passage of the compound through a hydrophobic membrane, such as a cell wall.

These detailed descriptions fall within the scope, and serve to exemplify, the above-described General Synthetic Procedures which form part of the invention. These detailed descriptions are presented for illustrative purposes only and are not intended as a restriction on the scope of the invention.

Although the pharmacological properties of the compounds of the invention (Formulas I and II) vary with structural change, in general, activity possessed by compounds of Formulas I and II may be demonstrated both in vitro as well as in vivo. Particularly, the pharmacological properties of the compounds of this invention may be confirmed by a number of pharmacological in vitro assays. The following exemplified pharmacological assays have been carried out with the compounds according to the invention. Compounds of the invention were found to inhibit the activity of various kinase enzymes, including, without limitation, p38 receptor kinase at doses less than 25 µM.

Biological Evaluation

The following assays were used to characterize the ability of compounds of the invention to inhibit the production of TNF-α and interleukin cytokines, including IL-1, IL-1-β, Il-6 and IL-8. The second assay can be used to measure the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a cyclooxygenase enzyme (COX-1 and COX-2) inhibition activity in vitro assay, can be used to characterize the ability of compounds of the invention to inhibit COX-1 and/or COX-2.

p38 In-Vitro HTRF Enzyme Assay

The compounds of the invention can be tested for their respective affinities for the p38 protein using a conventional p38 in-vitro enzyme activity assay. For example, a P38-alpha HTRF assay may be used to measure the protein's in-vitro phosphorylation activity, and the data analyzed using time resolved fluorimetry techniques (FRET). A p38 HTRF assay is as follows. The kinase reaction buffer for p38α, p38β, p38δ and p38γ HTRF assays consists of 50 mM Tris-pH 7.5, 5 mM $MgCl_2$, 0.1 mg/mL BSA, 100 µM $Na_3VO_4$ and 0.5 mM DTT.

The HTRF detection buffer contains 100 mM HEPES-pH 7.5, 100 mM NaCl, 0.1% BSA, 0.05% Tween-20, and 10 mM EDTA. Each compound was dissolved in 100% DMSO and serially diluted (3 fold, 10 point) in a polypropylene 96-well microtiter plate (drug plate). The final starting concentration of the compound in the p38α and p38β enzymatic assays was about 1 µM. The final starting concentration of each compound in the p38δ and p38γ enzymatic assays was about 10 µM. The p38α, p38β, p38δ and p38γ kinase reactions were carried out in a polypropylene 96-well black round bottom assay plate in total volume of 30 µL kinase reaction buffer. Appropriate concentration of purified and activated enzyme (recombinant human) was mixed with indicated concentration of ATP and 100 nM GST-ATF2-Avitag, in the presence or absence (HI control) of each compound. In the absence of enzyme, the background was measured as LO control. HI controls and LO controls contained only DMSO. The reaction was allowed to incubate for 1 hour at RT. The kinase reaction was terminated and phospho-ATF2 was revealed by addition of 30 µL of HTRF detection buffer supplemented with 0.1 nM Eu-anti-pTP and 4 nM SA-APC. After 60 minutes incubation at room temperature, the assay plate was read in a Discovery Plate Reader. The wells were excited with coherent 320 nm light and the ratio of delayed (50 ms post excitation) emissions at 620 nM (native europium fluorescence) and 665 nm (europium fluorescence transferred to allophycocyanin—an index of substrate phosphorylation) was determined (Park et al, 1999). The resulting data was analyzed by taking the proportion of substrate phosphorylated in the kinase reaction in the presence of each individual compound and comparing it with that phosphorylated in the presence of DMSO vehicle alone (HI control). The data was calculated using the formula: % control (POC)=(compound−average LO)/(average HI−average LO)*100. Data (consisting of POC and inhibitor concentration in µM) was fitted to a 4-parameter equation (y=A+ ((B−A)/(1+((x/C)^D))), where A is the minimum y (POC) value, B is the maximum y (POC), C is the x (compound concentration) at the point of inflection and D is the slope factor, using a Levenburg-Marquardt non-linear regression algorithm. The inhibition constant (Ki) of the inhibitor was estimated from the $IC_{50}$ (compound concentration at the point of inflection C) using the Cheng-Prussof equation: $Ki=IC_{50}/(1+S/Km)$, where S is the ATP substrate concentration, and Km is the Michaelis constant for ATP as determined experimentally. All results were expressed as the mean±the standard error of the mean. Data acquisition and non-linear regression algorithms were performed using Activity Base v5.2 and XLfit software v4.1 respectively. Additional assay information may be obtained in Park Y W, Cummings R T, Wu L, et al. Homogeneous Proximity Tyrosine Kinase Assays Scintillation Proximity Assay versus Homogeneous Time-Resolved Fluorescence. *Analytical Biochemistry.* 1999; 269: 94-104. Biological data ($IC_{50}$ value ranges—uM) for this assay for example compounds is provided in Table 1.

Lipopolysaccharide-Activated Monocyte TNF Production Assay

Isolation of Monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2\times10^6$/mL in DMEM supplemented to contain 2% FCS, 10 mM, 0.3 mg/mL glutamate, 100 U/mL penicillin G and 100 mg/mL streptomycin sulfate (complete media). Cells were plated into Falcon flat bottom, 96 well culture plates (200 µL/well) and cultured overnight at 37° C. and 6% $CO_2$. Non-adherent cells were removed by washing with 200 µl/well of fresh medium. Wells containing adherent cells (~70% monocytes) were replenished with 100 µL of fresh medium.

Preparation of Test Compound Stock Solutions

Test compounds were dissolved in DMZ. Compound stock solutions were prepared to an initial concentration of 10-50 µM. Stocks were diluted initially to 20-200 µl M in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 µL complete medium. Monocytes were cultured with test compounds for 60 min at which time 25 µL of complete medium containing 30 ng/mL lipopolysaccharide from *E. coli* K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 µL/well of 3 µg/mL murine anti-human TNF-α MAb (R&D Systems #MAB210). Wells were then blocked for 1 h at room temperature with 200 µL/well of $CaCl_2$-free ELISA buffer supplemented to contain 20 mg/mL BSA (standard ELISA buffer: 20 mM, 150 mM NaCl, 2 mM $CaCl_2$, 0.15 mM thimerosal, pH 7.4). Plates were washed and replenished with 100 µL of test supernatants (diluted 1:3) or standards. Standards consisted of eleven 1.5-fold serial dilutions from a stock of 1 ng/mL recombinant human TNF (R&D Systems). Plates were incubated at room temperature for 1 h on orbital shaker (300 rpm), washed and replenished with 100 µL/well of 0.5 µg/mL goat anti-human TNF-α (R&D systems #AB-210-NA) biotinylated at a 4:1 ratio. Plates were incubated for 40 min, washed and replenished with 100 µL/well of alkaline phosphatase-conjugated streptavidin (Jackson ImmunoResearch #016-050-084) at 0.02 µg/mL. Plates were incubated 30 min, washed and replenished with 200 µL/well of 1 mg/mL of p-nitrophenyl phosphate. After 30 min, plates were read at 405 nm on a $V_{max}$ plate reader.

Data Analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production. Test data for exemplary compounds in the whole blood monocyte assay (LPS induced TNF release) is presented in Table 1.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF-α from monocytes, compounds of this invention can also be shown to inhibit LPS induced release of IL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Lipopolysaccharide-Activated THP1 Cell TNF Production Assay

THP1 cells are resuspended in fresh THP1 media (RPMI 1640, 10% heat-inactivated FBS, 1×PGS, 1×NEAA, plus 30 μM βME) at a concentration of 1E6/mL. One hundred microliters of cells per well are plated in a polystyrene 96-well tissue culture. One microgram per mL of bacterial LPS is prepared in THP1 media and is transferred to the wells. Test compounds are dissolved in 100% DMSO and are serially diluted 3-fold in a polypropylene 96-well microtiter plate (drug plate). HI control and LO control wells contain only DMSO. One microliter of test compound from the drug plate followed by 10 μL of LPS are transferred to the cell plate. The treated cells are induced to synthesize and secrete TNF-α at 37° C. for 3 h. Forty microliters of conditioned media are transferred to a 96-well polypropylene plate containing 110 μL of ECL buffer (50 mM Tris-HCl pH 8.0, 100 mM NaCl, 0.05% Tween 20, 0.05% $NaN_3$ and 1% FBS) supplemented with 0.44 nM MAB610 monoclonal Ab (R&D Systems), 0.34 nM ruthenylated AF210NA polyclonal Ab (R&D Systems) and 44 μg/mL sheep anti-mouse M280 Dynabeads (Dynal). After a 2 h incubation at room temperature with shaking, the reaction is read on the ECL M8 Instrument (IGEN Inc.). A low voltage is applied to the ruthenylated TNF-α immune complexes, which in the presence of TPA (the active component in Origlo), results in a cyclical redox reaction generating light at 620 nM. The amount of secreted TNF-α in the presence of compound compared with that in the presence of DMSO vehicle alone (HI control) is calculated using the formula: % control (POC)=(cpd−average LO)/(average HI−average LO)*100. Data (consisting of POC and inhibitor concentration in μM) is fitted to a 4-parameter equation $(y=A+((B-A)/(1+((x/C)^D)))$, where A is the minimum y (POC) value, B is the maximum y (POC), C is the x (cpd concentration) at the point of inflection and D is the slope factor) using a Levenburg-Marquardt non-linear regression algorithm. Test data for exemplary compounds in the THP-1 cellular TNF production assay is presented in Table 1.

Inhibition of LPS-Induced TNF-α Production in Mice

Male DBA/1LACJ mice are dosed with vehicle or test compounds in a vehicle (the vehicle consisting of 0.5% tragacanth in 0.03 N HCl) 30 min prior to lipopolysaccharide (2 mg/Kg, I.V.) injection. Ninety minutes after LPS injection, blood is collected and the serum is analyzed by ELISA for TNF-α levels.

Compounds of the invention may be shown to have anti-inflammatory properties in animal models of inflammation, including carageenan paw edema, collagen induced arthritis and adjuvant arthritis, such as the carageenan paw edema model (C. A. Winter et al., Proc. Soc. Exp. Biol. Med., 111: 544 (1962); K. F. Swingle, in R. A. Scherrer and M. W. Whitehouse, Eds., Anti-inflammatory Agents, Chemistry and Pharmacology, 13(II):33, Academic, New York (1974) and collagen induced arthritis (D. E. Trentham et al., J. Exp. Med., 146:857 (1977); J. S. Courtenay, Nature (New Biol.), 283:666 (1980)).

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/mL ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per mL DMSO and store aliquots at −20° C.; (d) 250 μM human glucagon (Peninsula): solubilize 0.5 mg vial in 575 μl 0.1N acetic acid (1 μL yields 1 μM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 μL 10% BSA (heat-inactivated) and 990 μL Assay Buffer; (g) $^{125}$I-Glucagon (NEN, receptor-grade, 2200 Ci/mmol): dilute to 50,000 cpm/25 μL in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).
2. Add 10 mL Enzyme-free Dissoc. Fluid and hold for about 4 min at 37° C.
3. Gently tap cells free, triturate, take aliquot for counting and centrifuge remainder for 5 min at 1000 rpm.
4. Resuspend pellet in Assay Buffer at 75000 cells per 100 μL.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of $I^{125}$-glucagon binding in the presence of compounds of Formula I. The reagents are combined as follows:

|  | Compound/Vehicle | 250 μM Glucagon | $^{125}$I-Glucagon | CHO/hGLUR Cells |
| --- | --- | --- | --- | --- |
| Total Binding | —/5 μl | — | 25 μL | 100 μL |
| +Compound | 5 μl/— | — | 25 μL | 100 μL |
| Nonspecific Binding | —/5 μl | 1 μl | 25 μL | 100 μL |

The mixture is incubated for 60 min at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM- 10% FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 h on a shaker to prevent attachment. Cells are pelleted and resuspended in Hank's Buffered Saline (HBS) at a concentration of $2.5 \times 10^6$ cells/mL and plated in 96-well culture plates at a density of $5 \times 10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3 \times 10^6$ cells/mL in MEM-FBS containing 1 ng human IL-1b/mL, plated in 96-well tissue culture plates at a density of $3 \times 10^4$ cells per well, incubated on a shaker for 1 hour to evenly distribute cells, followed by an additional 2 hour static incubation to allow attachment. The media is then replaced with MEM containing 2% FBS (MEM-2% FBS) and 1 ng human IL-1b/mL, and the cells incubated for 18-22 h. Following replacement of media with 190 mL MEM, 10 mL of test compound diluted in HBS is added to achieve the desired concentration and the cells incubated for 4 h. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls. Various compounds of the invention may be shown to inhibit the COX-1 and/or COX-2 activity.

Indications

Accordingly, compounds of the invention are useful for, but not limited to, the prevention or treatment of inflammation, pro-inflammatory cytokines levels including, without limitation, TNF, IL-1, IL-2, IL-6 and/or IL-8, and disease associated therewith. The compounds of the invention have kinase modulatory activity in general, and p38 kinase modulatory activity in particular. In one embodiment of the invention, there is provided a method of treating a disorder related to the activity of p38 enzyme in a subject, the method comprising administering to the subject an effective dosage amount of a compound of a compound of Formulas I or II.

Accordingly, the compounds of the invention would be useful in therapy as anti-inflammatory agents in treating inflammation, or to minimize deleterious effects of p38. Based on the ability to modulate pro-inflammatory cytokine production, the compounds of the invention are also useful in treatment and therapy of cytokine-mediated diseases. Particularly, these compounds can be used for the treatment of rheumatoid arthritis, Pagets disease, osteoporosis, multiple myeloma, uveitis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection, or any combination thereof, in a subject.

An example of an inflammation related disorder is (a) synovial inflammation, for example, synovitis, including any of the particular forms of synovitis, in particular bursal synovitis and purulent synovitis, as far as it is not crystal-induced. Such synovial inflammation may for example, be consequential to or associated with disease, e.g. arthritis, e.g. osteoarthritis, rheumatoid arthritis or arthritis deformans. The present invention is further applicable to the systemic treatment of inflammation, e.g. inflammatory diseases or conditions, of the joints or locomotor apparatus in the region of the tendon insertions and tendon sheaths. Such inflammation may be, for example, consequential to or associated with disease or further (in a broader sense of the invention) with surgical intervention, including, in particular conditions such as insertion endopathy, myofasciale syndrome and tendomyosis. The present invention is further applicable to the treatment of inflammation, e.g. inflammatory disease or condition, of connective tissues including dermatomyositis and myositis.

The compounds of the invention can also be used as active agents against such disease states as arthritis, atherosclerosis, psoriasis, hemangiomas, myocardial angiogenesis, coronary and cerebral collaterals, ischemic limb angiogenesis, wound healing, peptic ulcer *Helicobacter* related diseases, fractures, cat scratch fever, rubeosis, neovascular glaucoma and retinopathies such as those associated with diabetic retinopathy or macular degeneration.

The compounds of the invention are also useful in the treatment of diabetic conditions such as diabetic retinopathy and microangiopathy.

The compounds of the present invention are also useful for treating ankylosing spondylitis, inflammatory bowel disease, inflammatory pain, ulcerative colitis, asthma, chronic obstructive pulmonary disease, myelodysplastic syndrome, endotoxic shock, chronic hepatitis C or a combination thereof.

The present invention also provides methods for the treatment of protein tyrosine kinase-associated disorders, comprising the step of administering to a subject in need thereof at least one compound of the Formula I or of Formula II in an amount effective therefore. Other therapeutic agents such as those described below may be employed with the inventive compounds in the present methods. In the methods of the present invention, such other therapeutic agent(s) may be administered prior to, simultaneously with or following the administration of the compound(s) of the present invention.

Use of the compound(s) of the present invention in treating protein tyrosine kinase-associated disorders is exemplified by, but is not limited to, treating a range of disorders such as:

The present invention also provides for a method for treating the aforementioned disorders such as atopic dermatitis by administration of a therapeutically effective amount of a compound of the present invention, which is an inhibitor of protein tyrosine kinase, to a patient, whether or not in need of such treatment.

In yet another embodiment, the compounds are useful for decreasing the level of, or lowering plasma concentrations of, one or more of TNF-α, IL-1β, IL-6 and IL-8 in a subject, generally a mammal and typically a human.

In yet another embodiment, the compounds are useful for treating a pain disorder in a subject, which is typically a human by administering to the subject an effective dosage amount of a compound according to formulas I or II.

In yet another embodiment, the compounds are useful for treating diabetes in a subject, which is typically a human, by administering to the subject an effective dosage amount of a compound according to formulas I or II, to produce a glucagon antagonist effect.

In yet another embodiment, the compounds are useful for decreasing prostaglandin production in a subject, which is typically a human, by administering to the subject an effective dosage amount of a compound according to formulas I or II.

In yet another embodiment, the compounds are useful for decreasing cyclooxygenase enzyme activity in a subject, which is typically a human, by administering to the subject an effective amount of a compound according to formulas I or II.

In yet another embodiment, the cyclooxygenase enzyme is COX-2.

Besides being useful for human treatment, these compounds are useful for veterinary treatment of companion animals, exotic animals and farm animals, including mammals, rodents, and the like. For example, animals including horses, dogs, and cats may be treated with compounds provided by the invention.

Formulations and Method of Use

Treatment of diseases and disorders herein is intended to also include therapeutic administration of a compound of the invention, or a pharmaceutical salt thereof, or a pharmaceutical composition of either to a subject (i.e., an animal, preferably a mammal, most preferably a human) which may be in need of preventative treatment, such as, for example, for pain, inflammation and the like. Treatment also encompasses prophylactic administration of a compound of the invention, or a pharmaceutical salt thereof, or a pharmaceutical composition of either to a subject (i.e., an animal, preferably a mammal, most preferably a human). Generally, the subject is initially diagnosed by a licensed physician and/or authorized medical practitioner, and a regimen for prophylactic and/or therapeutic treatment via administration of the compound(s) or compositions of the invention is suggested, recommended or prescribed.

The amount of compound(s) which is/are administered and the dosage regimen for treating TNF-α, IL-1, IL-6, and IL-8 mediated diseases, cancer, and/or hyperglycemia with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg, advantageously between about 0.01 and about 50 mg/kg, more advantageously about 0.01 and about 30 mg/kg, even more advantageously between about 0.1 and about 10 mg/kg, and even more advantageously between about 0.25 and about 1 mg/kg body weight may be appropriate, and should be useful for all methods of use disclosed herein. The daily dose can be administered in one to four doses per day.

While it may be possible to administer a compound of the invention alone, in the methods described, the compound administered normally will be present as an active ingredient in a pharmaceutical composition. Thus, in another embodiment of the invention, there is provided a pharmaceutical composition comprising a compound of this invention in combination with a pharmaceutically acceptable carrier, which includes diluents, excipients, adjuvants and the like (collectively referred to herein as "carrier" materials) as described herein, and, if desired, other active ingredients. A pharmaceutical composition of the invention may comprise an effective amount of a compound of the invention or an effective dosage amount of a compound of the invention. An effective dosage amount of a compound of the invention includes an amount less than, equal to or greater than an effective amount of the compound; for example, a pharmaceutical composition in which two or more unit dosages, such as in tablets, capsules and the like, are required to administer an effective amount of the compound, or alternatively, a multi-dose pharmaceutical composition, such as powders, liquids and the like, in which an effective amount of the compound is administered by administering a portion of the composition.

The compound(s) of the present invention may be administered by any suitable route, preferably in the form of a pharmaceutical composition adapted to such a route, in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. For example, these may contain an amount of active ingredient from about 1 to 2000 mg, advantageously from about 1 to 500 mg, and typically from about 5 to 150 mg. A suitable daily dose for a human or other mammal may vary widely depending on the condition of the patient and other factors, but, once again, can be determined using routine methods and practices.

For therapeutic purposes, the active compounds of this invention are ordinarily combined with one or more adjuvants or "excipients" appropriate to the indicated route of administration. If orally administered on a per dose basis, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, to form the final formulation. For example, the active compound(s) and excipient(s) may be tableted or encapsulated by known and accepted methods for convenient administration. Examples of suitable formulations include, without limitation, pills, tablets, soft and hard-shell gel capsules, troches, orally-dissolvable forms and delayed or controlled-release formulations thereof. Particularly, capsule or tablet formulations may contain one or more controlled-release agents, such as hydroxypropylmethyl cellulose, as a dispersion with the active compound(s).

In the case of psoriasis and other skin conditions, it may be preferable to apply a topical preparation of compounds of this invention to the affected area two to four times a day. Formulations suitable for topical administration include liquid or semi-liquid preparations suitable for penetration through the skin (e.g., liniments, lotions, ointments, creams, pastes, suspensions and the like) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include DMSO and related analogs.

The compounds of this invention can also be administered by transdermal device. Preferably transdermal administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier, which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base, which forms the oily dispersed phase of the cream formulations. Emulsifiers and emulsion stabilizers suitable for use in the formulation of the present invention include, for example, Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (ie. Captisol), cosolvent solubilization (ie. propylene glycol) or micellar solubilization (ie. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

For pulmonary administration, the pharmaceutical composition may be administered in the form of an aerosol or with an inhaler including dry powder aerosol.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

Accordingly, in yet another embodiment of the present invention, there is provided a method of manufacturing a medicament, the method comprising combining an amount of a compound according to Formulas I or II with a pharmaceutically acceptable carrier to manufacture the medicament.

In yet another embodiment, there is provided a method of manufacturing a medicament for the treatment of inflammation, the method comprising combining an amount of a compound according to Formulas I or II with a pharmaceutically acceptable carrier to manufacture the medicament.

Combinations

While the compounds of the invention can be dosed or administered as the sole active pharmaceutical agent, they can also be used in combination with one or more compounds of the invention or in conjunction with other agents. When administered as a combination, the therapeutic agents can be formulated as separate compositions that are administered simultaneously or sequentially at different times, or the therapeutic agents can be given as a single composition.

The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent.

Specifically, the administration of compounds of the present invention may be in conjunction with additional therapies known to those skilled in the art in the prevention or treatment of TNF-α, IL-1, IL-6, and IL-8 mediated diseases, cancer, and/or hyperglycemia.

If formulated as a fixed dose, such combination products employ the compounds of this invention within the accepted dosage ranges. Compounds of Formulas I and II may also be administered sequentially with known anti-inflammatory agents when a combination formulation is inappropriate. The invention is not limited in the sequence of administration; compounds of the invention may be administered either prior to, simultaneous with or after administration of the known anti-inflammatory agent.

The compounds of the invention may also be used in co-therapies with anti-neoplastic agents such as other kinase inhibitors, including CDK inhibitors, TNF inhibitors, metallomatrix proteases inhibitors (MMP), COX-2 inhibitors including celecoxib, rofecoxib, parecoxib, valdecoxib, and etoricoxib, NSAID's, SOD mimics or $\alpha_v\beta_3$ inhibitors.

The foregoing description is merely illustrative of the invention and is not intended to limit the invention to the disclosed compounds, compositions and methods. Variations and changes, which are obvious to one skilled in the art, are intended to be within the scope and nature of the invention, as defined in the appended claims. From the foregoing description, one skilled in the art can easily ascertain the essential characteristics of this invention, and without departing from the spirit and scope thereof, can make various changes and modifications of the invention to adapt it to various usages and conditions. All patents and other publications recited herein are hereby incorporated by reference in their entireties.

What is claimed is:
1. A compound of Formula I:

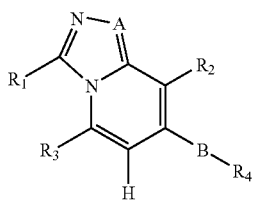

I or a stereoisomer or a pharmaceutically acceptable salt thereof, wherein

A is $CR^5$ or N;

B is a direct bond;

$R^1$ is —$(CR^7R^7)_n X$ or —$(CR^7R^8)_n X$, wherein n is 0, 1 or 2 and X is $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C(O)NR^7R^7$, $NR^7C(S)NR^7R^7$, $NR^7(COOR^7)$, $OC(O)NR^7R^7$, $C(O)NR^7R^8$, $C(S)NR^7R^8$, $NR^7C(O)R^8$, $NR^7C(S)R^8$, $NR^7C(O)NR^7R^8$, $NR^7C(S)NR^7R^8$, $NR^7(COOR^8)$, $OC(O)NR^7R^8$, $S(O)_2R^7$, $S(O)_2NR^7R^7$, $NR^7S(O)_2NR^7R^7$, $NR^7S(O)_2R^7$, $S(O)_2R^8$, $S(O)_2NR^7R^8$, $NR^7S(O)_2NR^7R^8$ or $NR^7S(O)_2R^8$, or X is $C_{1-10}$alkyl optionally substituted with one or more substituents of $R^9$, or X is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of $R^5$, $R^8$ or $R^9$;

each of $R^2$ and $R^3$, independently, is H, halo, haloalkyl, $NO_2$, CN, $OR^7$, $5R^7$, $NR^7R^7$, $NR^7R^8$, $C(O)R^7$, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^8$ or $R^9$;

$R^4$ is a ring selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, dihydrobenzofuranyl, benzothiophenyl, benzisoxazolyl, benzopyrazolyl, benzothiazolyl or benzimidazolyl, wherein said ring is substituted independently with 1-4 substituents of $R^{10}$, $R^{11}$, $R^{16}$, $NR^{10}R^{10}$, $NR^{10}R^{11}$, $OR^{10}$, $SR^{10}$, $OR^{11}$, $SR^{11}$, $C(O)R^{10}$, $C(S)R^{10}$, $C(NCN)R^{10}$, $C(O)R^{11}$, $C(S)R^{11}$, $C(NCN)R^{11}$, $C(O)C(O)R^{10}$, $OC(O)R^{10}$, $COOR^{10}$, $C(O)SR^{10}$, $C(O)C(O)R^{11}$, $OC(O)R^{11}$, $COOR^{11}$, $C(O)SR^{11}$, $C(O)NR^{10}R^{10}$, $C(S)NR^{10}R^{10}$, $C(O)NR^{10}R^{11}$, $C(S)NR^{10}R^{11}$, $OC(O)NR^{10}R^{11}$, $NR^{10}C(O)R^{11}$, $NR^{10}C(O)R^{11}$, $NR^{10}C(S)R^{10}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $NR^{10}(COOR^{10})$, $NR^{10}(COOR^{11})$, $NR^{10}C(O)C(O)R^{10}$, $NR^{10}C(O)C(O)R^{11}$, $NR^{10}C(O)C(O)NR^{10}R^{11}$, $S(O)_2R^{10}$, $S(O)_2R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$, provided that one substituent on $R^4$ is $NR^{10}R^{10}$, $NR^{10}R^{11}$, $C(O)NR^{10}R^{10}$, $C(S)NR^{10}R^{10}$, $C(O)NR^{10}R^{11}$, $C(S)NR^{10}R^{11}$, $NR^{10}C(O)R^{10}$, $NR^{10}C(S)R^{10}$, $NR^{10}C(O)R^{11}$, $NR^{10}C(S)R^{11}$, $NR^{10}C(O)NR^{10}R^{10}$, $NR^{10}C(O)NR^{10}R^{11}$, $NR^{10}C(S)NR^{10}R^{10}$, $NR^{10}C(S)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;

each of $R^5$ and $R^6$, independently, is H, halo, haloalkyl, $NO_2$, CN, $OR^7$, $NR^7R^7$ or $C_{1-10}$-alkyl, the $C_{1-10}$-alkyl optionally substituted with one or more substituents of $R^8$ or $R^9$;

$R^7$ is H, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^9R^9$, $C(O)NR^9R^9$, $NR^9C(O)R^8$, $NR^9C(O)R^9$, $NR^9C(O)NR^8R^9$, $NR^9C(O)NR^9R^9$, $NR^9(COOR^8)$, $NR^9(COOR^9)$, $OC(O)NR^8R^9$, $OC(O)NR^9R^9$, $S(O)_2NR^8R^9$, $S(O)_2NR^9R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-5 substituents of $R^9$;

$R^9$ is H, halo, haloalkyl, CN, OH, $NO_2$, $NH_2$, acetyl, oxo, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and each ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl, $C_{2-10}$-alkynyl, $C_{3-10}$-cycloalkyl or $C_{4-10}$-cycloalkenyl, each of the $C_{1-10}$-alkyl, $C_{2-10}$-alkenyl, $C_{2-10}$-alkynyl, $C_{3-10}$-cycloalkyl and $C_{4-10}$-cycloalkenyl optionally comprising 1-4 heteroatoms selected from N, O and S and optionally substituted with one or more substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{12}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}$, $NR^{12}S(O)_2NR^{11}R^{12}$; $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is a partially or frilly saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{12}$, $R^{13}$, $R^{14}$ or $R^{16}$;

alternatively, $R^{10}$ and $R^{11}$ taken together with the atom to which they are attached form a partially or fully saturated or unsaturated 5-6 membered ring of carbon atoms optionally including 1-3 heteroatoms selected from O, N, or S, and the ring optionally substituted independently with 1-5 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-5 substituents of $R^{13}$, $R^{14}$, $R^{15}$ or $R^{16}$;

$R^{13}$ is $NR^{14}R^{15}$, $NR^{15}R^{15}$, $OR^{14}$, $SR^{14}$, $OR^{15}$; $SR^{15}$, $C(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{14})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$; $NR^{15}S(O)_2NR^{15}R^{15}$, $NR^{14}S(O)_2R^{14}$ or $NR^{15}S(O)_2R^{15}$;

$R^{14}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

2. The compound of claim 1, or a pharmaceutically acceptable salt thereof, wherein A is N.

3. The compound of claim 1, or a pharmaceutically acceptable salt thereof, wherein $R^2$ and $R^3$, independently, is H, halo, haloalkyl, $NO_2$, $OR^7$, $NR^7R^7$ or $C_{1-10}$-alkyl.

4. The compound of claim 1, or a pharmaceutically acceptable salt thereof, wherein $R^1$ is $C_{1-10}$alkyl optionally substituted with one or more substituents of $R^9$, $NR^7R^7$, $NR^7R^8$, $OR^7$, $SR^7$, $OR^8$, $SR^8$, $C(O)R^7$, $C(O)R^8$, $C(O)NR^7R^7$, $NR^7C(O)R^7$, $NR^7C(O)NR^7R^7$, $NR^7(COOR^7)$, $C(O)NR^7R^8$, $NR^7C(O)R^8$, $NR^7C(O)NR^7R^8$, $NR^7(COOR^8)$, $S(O)_2NR^7R^7$, $NR^7S(O)_2NR^7R^7$, $NR^7S(O)_2R^7$, $S(O)_2NR^7R^8$, $NR^7S(O)_2NR^7R^8$, $NR^7S(O)_2R^8$ or a ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring system is optionally substituted independently with 1-3 substituents of $R^7$, $R^8$, $R^9$, oxo, $OR^7$, $SR^7$, $C(O)R^7$, $NR^7R^7$, $NR^7R^8$, $OR^8$, $SR^8$, $C(O)R^8$, $COOR^7$, $OC(O)R^7$, $COOR^8$, $OC(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $S(O)_2NR^7R^7$, $S(O)_2NR^7R^8$, $NR^7S(O_2)NR^7R^7$ or $NR^7S(O)_2NR^7R^8$.

5. The compound of claim 1, or a pharmaceutically acceptable salt thereof, wherein $R^1$ is $C_{1-10}$alkyl optionally substituted with one or more substituents of $R^9$, $NR^7R^7$, $NR^7R^8$, $OR^7$, $OR^8$, $C(O)R^7$, $C(O)R^8$, $C(O)NR^7R^7$, $NR^7C(O)R^7$, $NR^7C(O)NR^7R^7$, $C(O)NR^7R^8$, $NR^7C(O)R^8$, $NR^7C(O)NR^7R^8$, $S(O)_2NR^7R^7$, $NR^7S(O)_2NR^7R^7$, $NR^7S(O)_2R^7$, $S(O)_2NR^7R^8$, $NR^7S(O)_2NR^7R^8$, $NR^7S(O)_2R^8$ or $R^1$ is a ring system selected from phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, benzothiophenyl, benzimidazolyl, benzoxazolyl, benzisoxazolyl, benzopyrazolyl, benzothiazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, wherein said ring system is optionally substituted independently with 1-3 substituents of $R^7$, $R^8$, $R^9$, oxo, $OR^7$, $SR^7$, $C(O)R^7$, $NR^7R^7$, $NR^7R^8$, $OR^8$, $5R^8$, $C(O)R^8$, $COOR^7$, $OC(O)R^7$, $COOR^8$, $OC(O)R^8$, $C(O)NR^7R^7$, $C(O)NR^7R^8$, $NR^7C(O)R^7$, $NR^7C(O)R^8$, $NR^7C(O)NR^7R^7$, $NR^7C(O)NR^7R^8$, $S(O)_2NR^7R^7$, $S(O)_2NR^7R^8$, $NR^7S(O_2)NR^7R^7$ or $NR^7S(O)_2NR^7R^8$;

each of $R^2$ and $R^3$, independently, is H or $C_{1-10}$-alkyl;

$R^4$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, dihydrobenzofuranyl, benzothiophenyl, benzoxazolyl, benzopyrazolyl, benzisoxazolyl, benzothiazolyl or benzimidazolyl, said $R^4$ substituted with one substituent of $NR^{10}R^{10}$, $NR^{10}R^{11}$, $C(O)NR^{10}R^{10}$, $C(O)NR^{10}R^{11}$, $NR^{10}C(O)R^{10}$, $NR^{10}C(O)R^{11}$, $NR^{10}C(O)NR^{10}R^{10}$, $NR^{10}C(O)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$ and 0-3 substituents of $R^{16}$;

$R^7$ is H, $C_{1-10}$-alkyl, $C_{2-10}$-alkenyl, $C_{2-10}$-alkynyl or $C_{3-10}$-cycloalkyl, each of the $C_{1-10}$-alkyl, $C_{2-10}$-alkenyl, $C_{2-10}$-alkynyl and $C_{3-10}$-cycloalkyl optionally comprising 1-4 heteroatoms selected from N, O and S and optionally substituted with 1-3 substituents of $NR^8R^9$, $NR^9R^9$, $OR^8$, $SR^8$, $OR^9$, $SR^9$, $C(O)R^8$, $OC(O)R^8$, $COOR^8$, $C(O)R^9$, $OC(O)R^9$, $COOR^9$, $C(O)NR^8R^9$, $C(O)NR^9R^9$, $NR^9C(O)R^8$, $NR^9C(O)R^9$, $NR^9C(O)NR^8R^9$, $NR^9C(O)NR^9R^9$, $NR^9R^9$, $NR^9(COOR^8)$, $NR^9(COOR^9)$, $OC(O)NR^8R^9$, $OC(O)NR^9R^9$, $S(O)_2R^8$, $S(O)_2NR^8R^9$, $S(O)_2R^9$, $S(O)_2NR^9R^9$, $NR^9S(O)_2NR^8R^9$, $NR^9S(O)_2NR^9R^9$, $NR^9S(O)_2R^8$, $NR^9S(O)_2R^9$, $R^8$ or $R^9$;

$R^8$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^9$, oxo, $NR^9R^9$, $OR^9$, $SR^9$, $C(O)R^9$, $COOR^9$, $C(O)NR^9R^9$, $NR^9C(O)R^9$, $NR^9C(O)NR^9R^9$, $OC(O)NR^9R^9$, $S(O)_2R^9$, $S(O)_2NR^9R^9$, $NR^9S(O)_2R^9$, or a partially or fully saturated or unsaturated 5-6 membered ring of carbon atoms optionally including 1-3 heteroatoms selected from O, N, or S, and optionally substituted independently with 1-3 substituents of $R^9$;

alternatively, $R^7$ and $R^8$ taken together with the atom to which they are attached form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-3 substituents of $R^9$;

$R^9$ is H, halo, haloalkyl, CN, OH, $NO_2$, $NH_2$, acetyl, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl, $C_{1-10}$-thioalkoxyl and ring of said ring system is optionally substituted independently with 1-3 substituents of halo, haloalkyl, CN, $NO_2$, $NH_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

$R^{10}$ is H, halo, haloalkyl, CN, $NO_2$, $C_{1-10}$-alkyl, $C_{2-10}$-alkenyl or $C_{3-10}$-cycloalkyl, each of the $C_{1-10}$-alkyl, $C_{2-10}$-alkenyl, and $C_{3-10}$-cycloalkyl optionally comprising 1-4 heteroatoms selected from N, O and S and optionally substituted with 1-3 substituents of $R^{11}$, $R^{12}$ or $R^{16}$, $NR^{11}R^{12}$, $NR^{12}R^{12}$, $OR^{11}$, $SR^{11}$, $OR^{12}$, $SR^{12}$, $C(O)R^{11}$, $OC(O)R^{11}$, $COOR^{11}$, $C(O)R^{12}$, $OC(O)R^{12}$, $COOR^{12}$, $C(O)NR^{11}R^{12}$, $NR^{12}C(O)R^{11}$, $C(O)NR^{12}R^{12}$, $NR^{12}C(O)R^{12}$, $NR^{12}C(O)NR^{11}R^{12}$, $NR^{12}C(O)NR^{11}R^{12}$, $NR^{12}(COOR^{11})$, $NR^{12}(COOR^{12})$, $OC(O)NR^{11}R^{12}$, $OC(O)NR^{12}R^{12}$, $S(O)_2R^{11}$, $S(O)_2R^{12}$, $S(O)_2NR^{11}R^{12}$, $S(O)_2NR^{12}R^{12}NR^{12}S(O)_2NR^{11}R^{12}$, $NR^{12}S(O)_2NR^{12}R^{12}$, $NR^{12}S(O)_2R^{11}$, $NR^{12}S(O)_2R^{12}$, $NR^{12}S(O)_2R^{11}$ or $NR^{12}S(O)_2R^{12}$;

$R^{11}$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^{12}$, $R^{13}$, $R^{14}$ or $R^{16}$;

alternatively, $R^{10}$ and $R^{11}$ taken together form a partially or fully saturated or unsaturated 5-6 membered ring of carbon atoms optionally including 1-3 heteroatoms selected from O, N, or S, and the ring optionally substituted independently with 1-3 substituents of $R^{12}$, $R^{13}$, $R^{14}$ or $R^{16}$;

$R^{12}$ is H, $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkyl, each of which is optionally substituted independently with 1-3 substituents of $R^{13}$, $R^{14}$, $R^{15}$ or $R^{16}$;

$R^{13}$ is $NR^{14}R^{15}$, $NR^{15}R^{15}$, $OR^{14}$; $SR^{14}$, $OR^{15}$; $SR^{15}$, $C(O)R^{14}$, $OC(O)R^{14}$, $COOR^{14}$, $C(O)R^{15}$, $OC(O)R^{15}$, $COOR^{15}$, $C(O)NR^{14}R^{15}$, $C(O)NR^{15}R^{15}$, $NR^{14}C(O)R^{14}$, $NR^{15}C(O)R^{14}$, $NR^{14}C(O)R^{15}$, $NR^{15}C(O)R^{15}$, $NR^{15}C(O)NR^{14}R^{15}$, $NR^{15}C(O)NR^{15}R^{15}$, $NR^{15}(COOR^{15})$, $NR^{15}(COOR^{15})$, $OC(O)NR^{14}R^{15}$, $OC(O)NR^{15}R^{15}$, $S(O)_2R^{14}$, $S(O)_2R^{15}$, $S(O)_2NR^{14}R^{15}$, $S(O)_2NR^{15}R^{15}$, $NR^{14}S(O)_2NR^{14}R^{15}$, $NR^{15}S(O)_2NR^{15}R^{15}$, $NR^{14}S(O)_2R^{14}$ or $NR^{15}S(O)_2R^{15}$;

$R^{14}$ is phenyl, naphthyl, pyridyl, pyrimidyl, triazinyl, quinolinyl, isoquinolinyl, quinazolinyl, isoquinazolinyl, thiophenyl, furyl, pyrrolyl, imidazolyl, triazolyl, thiazolyl, oxazolyl, isoxazolyl, isothiazolyl, indolyl, isoindolyl, benzofuranyl, benzothiophenyl, benzimidazolyl, tetrahydrofuranyl, pyrrolidinyl, oxazolinyl, isoxazolinyl, thiazolinyl, pyrazolinyl, morpholinyl, piperidinyl, piperazinyl, pyranyl, dioxozinyl, cyclopropyl, cyclobutyl, cyclopentyl, cyclohexyl and cycloheptyl, each of which is optionally substituted independently with 1-3 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-3 substituents of $R^{16}$; and $R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 5-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl.

6. The compound of claim 1, or a pharmaceutically acceptable salt thereof, wherein $R^4$ is

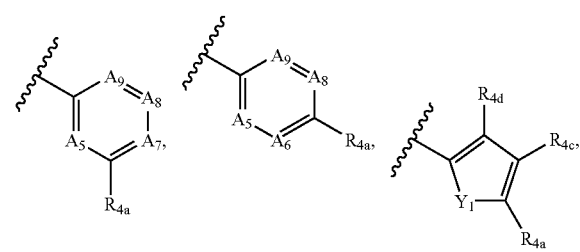

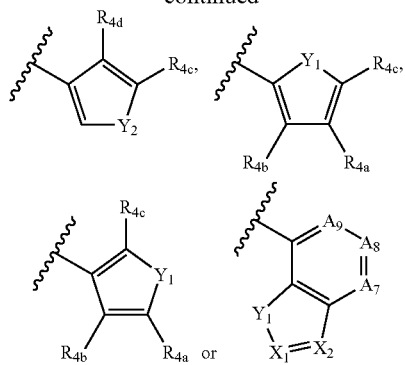

wherein
each of $A^5$, $A^6$, and $A^7$ is, independently, $CR^{4b}$ or N;
$A^8$ is $CR^{4c}$ or N; and
$A^9$ is $CR^{4d}$ or N;
$X^1$ is, independently, $CR^{4b}$ or N;
$X^2$ is $CR^{4a}$;
$Y^1$ is NH, O or S;
$Y^2$ is $NR^{4a}$;
$R^{4a}$ is $NR^{10}R^{10}$, $NR^{10}R^{11}$, $C(O)NR^{10}R^{10}$, $C(O)NR^{10}R^{10}$, $NR^{10}C(O)R^{10}$, $NR^{10}C(O)R^{11}$, $NR^{10}C(O)NR^{10}R^{10}$, $NR^{10}C(O)NR^{10}R^{11}$, $S(O)_2NR^{10}R^{10}$, $S(O)_2NR^{10}R^{11}$, $NR^{10}S(O)_2NR^{10}R^{11}$, $NR^{10}S(O)_2R^{10}$ or $NR^{10}S(O)_2R^{11}$;
$R^{4b}$ is H, halo, haloalkyl, CN, $NO_2$, $NH_2$, $C_{1-10}$-alkyl, $C_{1-10}$-alkoxyl, $C_{2-10}$-alkenyl, $C_{2-10}$-alkynyl or $C_{3-10}$-cycloalkyl;
$R^{4c}$ is H, halo, haloalkyl, CN, $NO_2$, $NH_2$, $C_{1-10}$-alkyl, $C_{1-10}$-alkoxyl, $C_{2-10}$-alkenyl, $C_{2-10}$-alkynyl or $C_{3-10}$-cycloalkyl;
$R^{4d}$ is H, halo, haloalkyl, CN, $NO_2$, $NH_2$, $C_{1-10}$-alkyl, $C_{1-10}$-alkoxyl, $C_{2-10}$-alkenyl, $C_{2-10}$-alkynyl or $C_{3-10}$-cycloalkyl; and
alternatively, $R^{4c}$ and $R^{4d}$ taken together with the atoms to which they are attached form a phenyl, pyridine or pyrimidine ring, wherein the ring optionally substituted with 1-3 substituents of halo, haloalkyl, CN, $NO_2$, $NH_2$, $C_{1-10}$-alkyl, $C_{2-10}$-alkenyl, $C_{2-10}$-alkynyl or $C_{3-10}$-cycloalkyl.

7. A compound of Formula II

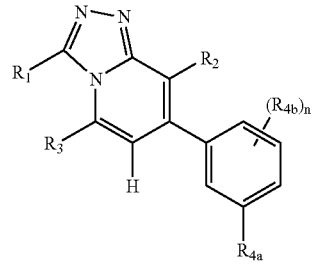

II or a stereoisomer or a pharmaceutically acceptable salt thereof, wherein
$R^1$ is —$(CR^7R^7)_nX$ or —$(CR^7R^8)_nX$, wherein n is 0, 1 or 2 and X is $NR^7R^7$, $NR^7R^8$, $OR^7$, $SR^7$, $OR^8$, $SR^8$, $C(O)R^7$, $OC(O)R^7$, $COOR^7$, $C(O)R^8$, $OC(O)R^8$, $COOR^8$, $C(O)NR^7R^7$, $C(S)NR^7R^7$, $NR^7C(O)R^7$, $NR^7C(S)R^7$, $NR^7C$ (O)NR$^7$R$^7$, NR$^7$C(S)NR$^7$R$^7$, NR$^7$(COOR$^7$), OC(O) NR$^7$R$^7$, C(O)NR$^7$R$^8$, C(S)NR$^7$R$^8$, NR$^7$C(O)R$^8$, NR$^7$C (S)R$^8$, NR$^7$C(O)NR$^7$R$^8$, NR$^7$C(S)NR$^7$R$^8$, NR$^7$ (COOR$^8$), OC(O)NR$^7$R$^8$, S(O)$_2$R$^7$, S(O)$_2$NR$^7$R$^7$, NR$^7$S (O)$_2$NR$^7$R$^7$, NR$^7$S(O)$_2$R$^7$, S(O)$_2$R$^8$, S(O)$_2$NR$^7$R$^8$, NR$^7$S(O)$_2$NR$^7$R$^8$ or NR$^7$S(O)$_2$R$^8$, or X is C$_{1-10}$alkyl optionally substituted with one or more substituents of R$^9$, or X is a 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, wherein said ring system is optionally substituted independently with one or more substituents of R$^5$, R$^8$ or R$^9$;

R$^2$ is H, halo, haloalkyl, NO$_2$, OR$^7$, NR$^7$R$^7$ or C$_{1-10}$-alkyl;

R$^3$ is H, halo, haloalkyl, NO$_2$, CN, OR$^7$, NR$^7$R$^7$ or C$_{1-10}$-alkyl;

R$^{4a}$ is NR$^{10}$R$^{10}$, NR$^{10}$R$^{11}$, C(O)NR$^{10}$R$^{10}$, C(O)NR$^{10}$R$^{11}$, NR$^{10}$C(O)R$^{10}$, NR$^{10}$C(O)R$^{11}$, NR$^{10}$C(O)NR$^{10}$R$^{10}$, NR$^{10}$C(O)NR$^{10}$R$^{11}$, S(O)$_2$NR$^{10}$R$^{10}$, S(O)$_2$NR$^{10}$R$^{11}$, NR$^{10}$S(O)$_2$NR$^{10}$R$^{11}$, NR$^{10}$S(O)$_2$R$^{10}$ or NR$^{10}$S(O)$_2$R$^{11}$;

each R$^{4b}$, independently, is halo, haloalkyl, CN, NO$_2$, NH$_2$, C$_{1-10}$-alkyl, C$_{1-10}$-alkoxyl, C$_{2-10}$-alkenyl, C$_{2-10}$-alkynyl or C$_{3-10}$-cycloalkyl;

R$^7$ is H, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with one or more substituents of NR$^8$R$^9$, NR$^9$R$^9$, OR$^8$, 5R$^8$, OR$^9$, 5R$^9$, C(O)R$^8$, OC(O)R$^8$, COOR$^8$, C(O) R$^9$, OC(O)R$^9$, COOR$^9$, C(O)NR$^8$R$^9$, C(O)NR$^9$R$^9$, NR$^9$C(O)R$^8$, NR$^9$C(O)R$^9$, NR$^9$C(O)NR$^8$R$^9$, NR$^9$C(O) NR$^9$R$^9$, NR$^9$(COOR$^8$), NR$^9$(COOR$^9$), OC(O)NR$^8$R$^9$, OC(O)NR$^9$R$^9$, S(O)$_2$R$^8$, S(O)$_2$NR$^8$R$^9$, S(O)$_2$R$^9$, S(O)$_2$NR$^9$R$^9$, NR$^9$S(O)$_2$NR$^8$R$^9$, NR$^9$S(O)$_2$NR$^9$R$^9$, NR$^9$S(O)$_2$R$^8$, NR$^9$S(O)$_2$R$^9$, R$^8$ or R$^9$;

R$^8$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^9$, oxo, NR$^9$R$^9$, OR$^9$, SR$^9$, C(O)R$^9$, COOR$^9$, C(O)NR$^9$R$^9$, NR$^9$C(O)R$^9$, NR$^9$C(O)NR$^9$R$^9$, OC(O)NR$^9$R$^9$, S(O)$_2$R$^9$, S(O)$_2$NR$^9$R$^9$, NR$^9$S(O)$_2$R$^9$, or a partially or fully saturated or unsaturated 5-6 membered ring of carbon atoms optionally including 1-3 heteroatoms selected from O, N, or S, and optionally substituted independently with 1-3 substituents of R$^9$;

alternatively, R$^7$ and R$^8$ taken together with the atom to which they are attached form a saturated or partially or fully unsaturated 5-6 membered monocyclic or 7-10 membered bicyclic ring of carbon atoms optionally including 1-3 heteroatoms selected from O, N, or S, and the ring optionally substituted independently with 1-5 substituents of R$^9$;

R$^9$ is H, halo, haloalkyl, CN, OH, NO$_2$, NH$_2$, acetyl, oxo, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl or a saturated or partially or fully unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, wherein each of the C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl, C$_{1-10}$-thioalkoxyl and each ring of said ring system is optionally substituted independently with 1-3 substituents of halo, haloalkyl, CN, NO$_2$, NH$_2$, OH, oxo, methyl, methoxyl, ethyl, ethoxyl, propyl, propoxyl, isopropyl, cyclopropyl, butyl, isobutyl, tert-butyl, methylamine, dimethylamine, ethylamine, diethylamine, propylamine, isopropylamine, dipropylamine, diisopropylamine, benzyl or phenyl;

R$^{10}$ is H, halo, haloalkyl, CN, NO$_2$, C$_{1-10}$-alkyl, C$_{2-10}$-alkenyl, C$_{2-10}$-alkynyl, C$_{3-10}$-cycloalkyl or C$_{4-10}$-cycloalkenyl, each of the C$_{1-10}$-alkyl, C$_{2-10}$-alkenyl, C$_{2-10}$-alkynyl, C$_{3-10}$-cycloalkyl and C$_{4-10}$-cycloalkenyl optionally comprising 1-4 heteroatoms selected from N, O and S and optionally substituted with one or more substituents of R$^{11}$, R$^{12}$ or R$^{16}$, NR$^{11}$R$^{12}$, NR$^{12}$R$^{12}$, OR$^{11}$, SR$^{11}$, OR$^{12}$, SR$^{12}$, C(O)R$^{11}$, OC(O)R$^{11}$, COOR$^{11}$, C(O)R$^{12}$, OC(O)R$^{12}$, COOR$^{12}$, C(O) NR$^{11}$R$^{12}$, NR$^{12}$C(O)R$^{11}$C(O)NR$^{12}$R$^{12}$, NR$^{12}$C(O)R$^{12}$, NR$^{12}$C(O)NR$^{11}$R$^{12}$, NR$^{12}$C(O)NR$^{12}$R$^{12}$, NR$^{12}$ (COOR$^{11}$), NR$^{12}$(COOR$^{12}$), OC(O)NR$^{11}$R$^{12}$, OC(O) NR$^{12}$R$^{12}$, S(O)$_2$R$^{11}$, S(O)$_2$R$^{12}$, S(O)$_2$NR$^{11}$R$^{12}$, S(O)$_2$ NR$^{12}$R$^{12}$, NR$^{12}$S(O)$_2$NR$^{11}$R$^{12}$ NR$^{12}$S(O)$_2$NR$^{12}$R$^{12}$, NR$^{12}$S(O)$_2$R$^{11}$, NR$^{12}$S(O)$_2$R$^{12}$, NR$^{12}$S(O)$_2$R$^{11}$ or NR$^{12}$S(O)$_2$R$^{12}$;

R$^{11}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of R$^{12}$, R$^{13}$, R$^{14}$ or R$^{16}$;

alternatively, R$^{10}$ and R$^{11}$ taken together form a partially or fully saturated or unsaturated 5-6 membered ring of carbon atoms optionally including 1-3 heteroatoms selected from O, N, or S, and the ring optionally substituted independently with 1-5 substituents of R$^{12}$, R$^{13}$, R$^{14}$ or R$^{16}$;

R$^{12}$ is H, C$_{1-10}$-alkyl, C$_{2-10}$-alkenyl, C$_{2-10}$-alkynyl, C$_{3-10}$-cycloalkyl, C$_{4-10}$-cycloalkenyl, C$_{1-10}$-alkylamino-, C$_{1-10}$-dialkylamino-, C$_{1-10}$-alkoxyl or C$_{1-10}$-thioalkyl, each of which is optionally substituted independently with 1-5 substituents of R$^{13}$, R$^{14}$, R$^{15}$ or R$^{16}$;

R$^{13}$ is NR$^{14}$R$^{15}$, NR$^{15}$R$^{15}$, OR$^{14}$, SR$^{14}$, OR$^{15}$; SR$^{15}$, C(O) R$^{14}$, OC(O)R$^{14}$, COOR$^{14}$, OC(O)R$^{15}$, COOR$^{15}$, C(O) NR$^{14}$R$^{15}$, C(O)NR$^{15}$R$^{15}$, NR$^{14}$C(O)R$^{14}$, NR$^{15}$C(O) R$^{14}$, NR$^{14}$C(O)R$^{15}$, NR$^{15}$C(O)R$^{15}$, NR$^{15}$C(O) NR$^{14}$R$^{15}$, NR$^{15}$C(O)NR$^{15}$R$^{15}$, NR$^{15}$(COOR$^{14}$), NR$^{15}$ (COOR$^{15}$), OC(O)NR$^{14}$R$^{15}$, OC(O)NR$^{15}$R$^{15}$, S(O)$_2$ R$^{14}$, S(O)$_2$R$^{15}$, S(O)$_2$NR$^{14}$R$^{15}$, S(O)$_2$NR$^{15}$R$^{15}$, NR$^{14}$S (O)$_2$NR$^{14}$R$^{15}$, NR$^{15}$S(O)$_2$NR$^{15}$R$^{15}$, NR$^{14}$S(O)$_2$R$^{14}$ or NR$^{15}$S(O)$_2$R$^{15}$;

R$^{14}$ is a partially or fully saturated or unsaturated 5-8 membered monocyclic, 6-12 membered bicyclic, or 7-14 membered tricyclic ring system, said ring system formed of carbon atoms optionally including 1-3 heteroatoms if monocyclic, 1-6 heteroatoms if bicyclic, or 1-9 heteroatoms if tricyclic, said heteroatoms selected from O, N, or S, and wherein each ring of said ring system is optionally substituted independently with 1-5 substituents of $R^{15}$ or $R^{16}$;

$R^{15}$ is H or $C_{1-10}$-alkyl, $C_{2-10}$-alkenyl, $C_{2-10}$-alkynyl, $C_{3-10}$-cycloalkyl, $C_{4-10}$-cycloalkenyl, $C_{1-10}$-alkylamino-, $C_{1-10}$-dialkylamino-, $C_{1-10}$-alkoxyl or $C_{1-10}$-thioalkoxyl, each of which is optionally substituted independently with 1-5 substituents of $R^{16}$;

$R^{16}$ is H, halo, haloalkyl, CN, OH, $NO_2$, $NH_2$, OH, methyl, methoxyl, ethyl, ethoxyl, propyl, propoxyl, isopropyl, butyl, isobutyl, tert-butyl, methylamino, dimethylamino, ethylamino, diethylamino, isopropylamino, oxo, acetyl, benzyl, cyclopropyl, cyclobutyl or a partially or fully saturated or unsaturated 3-8 membered monocyclic or 6-12 membered bicyclic ring system, said ring system formed of carbon atoms optionally including 1-3 heteroatoms if monocyclic or 1-6 heteroatoms if bicyclic, said heteroatoms selected from O, N, or S, and optionally substituted independently with 1-5 substituents of halo, haloalkyl, CN, $NO_2$, $NH_2$, OH, methyl, methoxyl, ethyl, ethoxyl, propyl, propoxyl, isopropyl, cyclopropyl, butyl, isobutyl, tert-butyl, methylamino, dimethylamino, ethylamino, diethylamino, isopropylamino, benzyl or phenyl; and n is 1, 2 or 3.

8. The compound of claim 7, or a pharmaceutically acceptable salt thereof, wherein $R^1$ is $C_{1-10}$alkyl optionally substituted with one or more substituents of $R^9$, or $R^1$ is phenyl, naphthyl, pyridyl, pyrimidyl, triazinyl, quinolinyl, isoquinolinyl, quinazolinyl, isoquinazolinyl, thiophenyl, furyl, pyrrolyl, pyrazolyl, imidazolyl, triazolyl, thiazolyl, oxazolyl, isoxazolyl, isothiazolyl, indolyl, isoindolyl, benzofuranyl, dihydrobenzofuranyl, benzothiophenyl, benzisoxazolyl, benzopyrazolyl, benzothiazolyl or benzimidazolyl, each of which is optionally substituted as defined in claim 7;

each of $R^2$ and $R^3$, independently, is H or $C_{1-10}$-alkyl;

$R^{4a}$ is $C(O)NR^{10}R^{10}$, $C(O)NR^{10}R^{11}$, $NR^{10}C(O)R^{10}$, $NR^{10}C(O)R^{11}$, $S(O)_2NR^{10}R^{10}$, $S(O)_2NR^{10}R^{11}$, $NR^{10}S(O)_2R^{10}$ or $NR^{10}S(O)_2R^{11}$;

each $R^{4b}$, independently, is halo, haloalkyl, CN, $NO_2$, $NH_2$, $C_{1-10}$-alkyl or $C_{1-10}$-alkoxyl; and n is 1 or 2.

9. The compound of claim 1, or a pharmaceutically acceptable salt thereof, selected from:

4-methyl-N-(1-methyl-1H-pyrazol-5-yl)-3-(3-(4-(trifluoromethyl)-3-pyridinyl)imidazo[1,5-a]pyridin-7-yl)benzamide;

3-(3-(3,5-difluorophenyl)imidazo[1,5-a]pyridin-7-yl)-4-methyl-N-(1-methyl-1H-pyrazol-5-yl)benzamide;

3-(3-(2-chlorophenyl)imidazo[1,5-a]pyridin-7-yl)-4-methyl-N-(1-methyl-1H-pyrazol-5-yl)benzamide;

3-(3-(2-chlorophenyl)[1,2,4]triazolo[4,3-a]pyridin-7-yl)-N-cyclopropyl-4-methylbenzamide;

N-cyclopropyl-4-methyl-3-(3-(4-(methylsulfonyl)phenyl) [1,2,4]triazolo[4,3-a]pyridin-7-yl)benzamide;

4-methyl-N-(1-methyl-1H-pyrazol-5-yl)-3-(3-(4-(methylsulfonyl)phenyl)[1,2,4]triazolo[4,3-a]pyridin-7-yl) benzamide;

N-cyclopropyl-3-(3-(4-fluoro-2-methylphenyl)[1,2,4] triazolo[4,3-a]pyridin-7-yl)-4-methylbenzamide;

3-(3-(4-fluoro-2-methylphenyl)[1,2,4]triazolo[4,3-a]pyridin-7-yl)-4-methyl-N-(1-methylcyclopropyl)benzamide;

3-(3-(4-fluoro-2-methylphenyl)[1,2,4]triazolo[4,3-a]pyridin-7-yl)-4-methyl-N-(1-methyl-1H-pyrazol-5-yl)benzamide;

N-cyclopropyl-4-methyl-3-(3-phenyl)[1,2,4]triazolo[4,3-a]pyridin-7-yl)benzamide;

4-methyl-N-(1-methyl-1H-pyrazol-5-yl)-3-(3-(1-(trifluoromethyl)cyclopropyl)[1,2,4]triazolo[4,3-a]pyridin-7-yl)benzamide;

N-cyclopropyl-4-methyl-3-(3-(1-(trifluoromethyl)cyclopropyl)[1,2,4]triazolo[4,3-a]pyridin-7-yl)benzamide;

N-cyclopropyl-3-(3-(4-fluoro-2-methylphenyl)imidazo [1,5-a]pyridin-7-yl)-4-methylbenzamide;

3-(3-(4-fluoro-2-methylphenyl)imidazo[1,5-a]pyridin-7-yl)-4-methyl-N-(1-methyl-1H-pyrazol-5-yl)benzamide;

3-(3-amino[1,2,4]triazolo[4,3-a]pyridin-7-yl)-N-cyclopropyl-4-methylbenzamide;

N-cyclopropyl-3-(3-(2,2-dimethylpropyl)[1,2,4]triazolo [4,3-a]pyridin-7-yl)-4-methylbenzamide;

N-cyclopropyl-4-methyl-3-(3-(1-methylethyl)[1,2,4]triazolo[4,3-a]pyridin-7-yl)benzamide;

4-methyl-3-(3-(1-methylethyl)[1,2,4]triazolo[4,3-a]pyridin-7-yl)-N-(1-methyl-1H-pyrazol-5-yl)benzamide;

N-cyclopropyl-4-methyl-3-(3-(3-pyridinyl)[1,2,4]triazolo [4,3-a]pyridin-7-yl)benzamide;

N-cyclopropyl-3-(3-(2-fluorophenyl)[1,2,4]triazolo[4,3-a]pyridin-7-yl)-4-methylbenzamide;

N-cyclopropyl-4-methyl-3-(3-(2-methyl-3-pyridinyl)[1,2,4]triazolo[4,3-a]pyridin-7-yl)benzamide;

3-(3-(2-chlorophenyl)[1,2,4]triazolo[4,3-a]pyridin-7-yl)-N,4-dimethylbenzamide;

3-(3-(2-chlorophenyl)[1,2,4]triazolo[4,3-a]pyridin-7-yl)-4-methyl-N-(1-methylethyl)benzamide;

3-(3-(2-chloro-5-fluorophenyl)[1,2,4]triazolo[4,3-a]pyridin-7-yl)-N-cyclopropyl-4-methylbenzamide;

N-cyclopropyl-3-(3-(1,1-dimethylethyl)[1,2,4]triazolo[4,3-a]pyridin-7-yl)-5-fluoro-4-methylbenzamide;

3-(3-(2-chlorophenyl)[1,2,4]triazolo[4,3-a]pyridin-7-yl)-N-cyclopropyl-5-fluoro-4-methylbenzamide;

N-cyclopropyl-4-methyl-3-(3-(3-methyl-2-thienyl)[1,2,4] triazolo[4,3-a]pyridin-7-yl)benzamide;

3-(3-(2-chloro-6-fluorophenyl)[1,2,4]triazolo[4,3-a]pyridin-7-yl)-N-cyclopropyl-5-fluoro-4-methylbenzamide;

N-cyclopropyl-4-methyl-3-(3-(4-methyl-1,3-oxazol-5-yl) [1,2,4]triazolo[4,3-a]pyridin-7-yl)benzamide;

3-(3-(2-chloro-6-fluorophenyl)[1,2,4]triazolo[4,3-a]pyridin-7-yl)-5-fluoro-4-methyl-N-(1-methyl-1H-pyrazol-5-yl)benzamide;

N-cyclopropyl-3-(3-(2,6-difluorophenyl)[1,2,4]triazolo [4,3-a]pyridin-7-yl)-5-fluoro-4-methylbenzamide;

N-cyclopropyl-4-methyl-3-(3-(phenylamino)[1,2,4]triazolo[4,3-a]pyridin-7-yl)benzamide;

N-cyclopropyl-3-(3-(1,1-dimethylethyl)-8-methyl[1,2,4] triazolo[4,3-a]pyridin-7-yl)-5-fluoro-4-methylbenzamide;

3-(3-(3-chloro-4-pyridinyl)[1,2,4]triazolo[4,3-a]pyridin-7-yl)-N-cyclopropyl-4-methylbenzamide;

N-cyclopropyl-4-methyl-3-(3-((1R)-2,2,2-trifluoro-1-methylethyl)[1,2,4]triazolo[4,3-a]pyridin-7-yl)benzamide;

3-(3-cyclopentyl[1,2,4]triazolo[4,3-a]pyridin-7-yl)-N-cyclopropyl-4-methylbenzamide;

3-(3-(2,6-difluorophenyl)[1,2,4]triazolo[4,3-a]pyridin-7-yl)-N-3-isoxazolyl-4-methylbenzamide;

3-(3-(2-fluorophenyl)[1,2,4]triazolo[4,3-a]pyridin-7-yl)-4-methyl-N-(1-methyl-1H-pyrazol-5-yl)benzamide;

N-cyclopropyl-4-methyl-3-(3-(2,2,2-trifluoroethyl)[1,2,4]triazolo[4,3-a]pyridin-7-yl)benzamide;

N-cyclopropyl-4-methyl-3-(3-(2-methylphenyl)[1,2,4]triazolo[4,3-a]pyridin-7-yl)benzamide;

4-methyl-N-(1-methyl-1H-pyrazol-5-yl)-3-(3-(2-methyl-3-pyridinyl)[1,2,4]triazolo[4,3-a]pyridin-7-yl)benzamide;

N-cyclopropyl-4-methyl-3-(3-(2-methyl-3-pyridinyl)[1,2,4]triazolo[4,3-a]pyridin-7-yl)benzamide;

3-(3-(2-chlorophenyl)-6-methyl[1,2,4]triazolo[4,3-a]pyridin-7-yl)-N-cyclopropyl-4-methylbenzamide; and 3-(3-(2-chlorophenyl)-6-methyl[1,2,4]triazolo[4,3-a]pyridin-7-yl)-4-methyl-N-(1-methyl-1H-pyrazol-5-yl)benzamide.

10. A pharmaceutical composition comprising a compound according to claim 1 and a pharmaceutically acceptable excipient.

11. A method of treating rheumatoid arthritis, plaque psoriasis, psoriatic arthritis, ankylosing spondylitis or a combination thereof in a subject, the method comprising administering to the subject an effective dosage amount of a compound according to claim 1.

12. A method of lowering plasma concentrations of TNF-a in a subject, the method comprising administering to the subject a therapeutically effective amount of a compound according to claim 1.

13. A method of making a compound according to claim 7, the method comprising the step of reacting a compound 7,

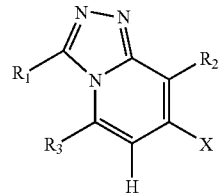

wherein A, $R^1$, $R^2$ and $R^3$ are as defined in claim 1 and X is a halogen, with a boronic acid having a general formula

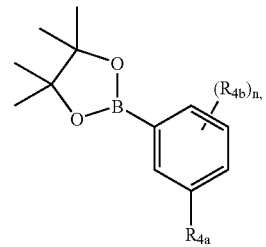

wherein $R^{4a}$, $R^{4b}$ and in are as defined in claim 7, to make a compound of claim 7.

* * * * *